United States Patent
Gubatayao et al.

(10) Patent No.: US 9,765,389 B2
(45) Date of Patent: Sep. 19, 2017

(54) SCANNING REAL-TIME MICROFLUIDIC THERMOCYCLER AND METHODS FOR SYNCHRONIZED THERMOCYCLING AND SCANNING OPTICAL DETECTION

(71) Applicant: BECTON, DICKINSON & COMPANY, Franklin Drive, NJ (US)

(72) Inventors: Thomas Catalino Gubatayao, Westland, MI (US); Kalyan Handique, Ypsilanti, MI (US); Karthik Ganesan, Ann Arbor, MI (US); Daniel M. Drummond, Livonia, MI (US)

(73) Assignee: Becton, Dickinson and Company, Franklin Lakes, NJ (US)

(*) Notice: Subject to any disclaimer, the term of this patent is extended or adjusted under 35 U.S.C. 154(b) by 0 days.

(21) Appl. No.: 14/054,397

(22) Filed: Oct. 15, 2013

(65) Prior Publication Data
US 2014/0045186 A1 Feb. 13, 2014

Related U.S. Application Data

(63) Continuation of application No. PCT/US2012/033667, filed on Apr. 13, 2012.
(Continued)

(51) Int. Cl.
*C12P 19/34* (2006.01)
*C12Q 1/68* (2006.01)
(Continued)

(52) U.S. Cl.
CPC ............. *C12Q 1/686* (2013.01); *B01L 7/52* (2013.01); *B01L 9/527* (2013.01);
(Continued)

(58) Field of Classification Search
None
See application file for complete search history.

(56) References Cited

U.S. PATENT DOCUMENTS 1,434,314 A 10/1922 Raich
1,616,419 A 2/1927 Wilson
(Continued)

FOREIGN PATENT DOCUMENTS

CA 2294819 1/1999
CN 1968754 A 5/2007
(Continued)

OTHER PUBLICATIONS

Meyers, R.A., Molecular Biology and Biotechnology: A Comprehensive Desk Reference; VCH Publishers, Inc. New York, NY; (1995) pp. 418-419.
(Continued)

*Primary Examiner* — Betty Forman
(74) *Attorney, Agent, or Firm* — Knobbe Martens Olson & Bear LLP

(57) ABSTRACT

Systems and methods for performing simultaneous nucleic acid amplification and detection. The systems and methods comprise methods for managing a plurality of protocols in conjunction with directing a sensor array across each of a plurality of reaction chambers. In certain embodiments, the protocols comprise thermocycling profiles and the methods may introduce offsets and duration extensions into the thermocycling profiles to achieve more efficient detection behavior.

10 Claims, 29 Drawing Sheets

Related U.S. Application Data

(60) Provisional application No. 61/476,167, filed on Apr. 15, 2011, provisional application No. 61/476,175, filed on Apr. 15, 2011.

(51) Int. Cl.
*B01L 7/00* (2006.01)
*B01L 9/00* (2006.01)
*G01N 35/02* (2006.01)
*G01N 21/64* (2006.01)
*G01N 35/00* (2006.01)
*G01N 21/27* (2006.01)

(52) U.S. Cl.
CPC ..... *G01N 21/6428* (2013.01); *G01N 21/6452* (2013.01); *G01N 35/00693* (2013.01); *G01N 35/026* (2013.01); *B01L 2300/1822* (2013.01); *B01L 2300/1827* (2013.01); *B01L 2300/1838* (2013.01); *G01N 21/274* (2013.01); *G01N 21/278* (2013.01); *G01N 2021/6419* (2013.01); *G01N 2021/6421* (2013.01); *G01N 2021/6441* (2013.01); *G01N 2035/00366* (2013.01)

(56) References Cited

U.S. PATENT DOCUMENTS

| | | |
|---|---|---|
| 1,733,401 A | 8/1930 | Lovekin |
| D189,404 S | 12/1960 | Nicolle |
| 3,528,449 A | 9/1970 | Witte et al. |
| 3,813,316 A | 5/1974 | Chakrabarty et al. |
| 3,985,649 A | 10/1976 | Eddelman |
| 4,018,089 A | 4/1977 | Dzula et al. |
| 4,018,652 A | 4/1977 | Lanham et al. |
| 4,038,192 A | 7/1977 | Serur |
| 4,055,395 A | 10/1977 | Honkawa et al. |
| D249,706 S | 9/1978 | Adamski |
| 4,139,005 A | 2/1979 | Dickey |
| D252,157 S | 6/1979 | Kronish et al. |
| D252,341 S | 7/1979 | Thomas |
| D254,687 S | 4/1980 | Fadler et al. |
| 4,212,744 A | 7/1980 | Oota |
| D261,033 S | 9/1981 | Armbruster |
| D261,173 S | 10/1981 | Armbruster |
| 4,301,412 A | 11/1981 | Hill et al. |
| 4,439,526 A | 3/1984 | Columbus |
| 4,457,329 A | 7/1984 | Werley et al. |
| 4,466,740 A | 8/1984 | Kano et al. |
| 4,504,582 A | 3/1985 | Swann |
| 4,522,786 A | 6/1985 | Ebersole |
| D279,817 S | 7/1985 | Chen et al. |
| D282,208 S | 1/1986 | Lowry |
| 4,599,315 A | 7/1986 | Terasaki et al. |
| 4,612,873 A | 9/1986 | Eberle |
| 4,612,959 A | 9/1986 | Costello |
| D288,478 S | 2/1987 | Carlson et al. |
| 4,647,432 A | 3/1987 | Wakatake |
| 4,654,127 A | 3/1987 | Baker et al. |
| 4,673,657 A | 6/1987 | Christian |
| 4,678,752 A | 7/1987 | Thorne et al. |
| 4,683,195 A | 7/1987 | Mullis et al. |
| 4,683,202 A | 7/1987 | Mullis |
| D292,735 S | 11/1987 | Lovborg |
| 4,720,374 A | 1/1988 | Ramachandran |
| 4,724,207 A | 2/1988 | Hou et al. |
| 4,798,693 A | 1/1989 | Mase et al. |
| 4,800,022 A | 1/1989 | Leonard |
| 4,841,786 A | 6/1989 | Schulz |
| D302,294 S | 7/1989 | Hillman |
| 4,871,779 A | 10/1989 | Killat et al. |
| 4,895,650 A | 1/1990 | Wang |
| 4,919,829 A | 4/1990 | Gates et al. |
| 4,921,809 A | 5/1990 | Schiff et al. |
| 4,935,342 A | 6/1990 | Seligson et al. |
| 4,946,562 A | 8/1990 | Guruswamy |
| 4,949,742 A | 8/1990 | Rando et al. |
| D310,413 S | 9/1990 | Bigler et al. |
| 4,963,498 A | 10/1990 | Hillman et al. |
| 4,967,950 A | 11/1990 | Legg et al. |
| D312,692 S | 12/1990 | Bradley |
| 4,978,502 A | 12/1990 | Dole et al. |
| 4,978,622 A | 12/1990 | Mishell et al. |
| 4,989,626 A | 2/1991 | Takagi et al. |
| 5,001,417 A | 3/1991 | Pumphrey et al. |
| 5,004,583 A | 4/1991 | Guruswamy et al. |
| 5,048,554 A | 9/1991 | Kremer |
| 5,053,199 A | 10/1991 | Keiser et al. |
| 5,060,823 A | 10/1991 | Perlman |
| 5,061,336 A | 10/1991 | Soane |
| 5,064,618 A | 11/1991 | Baker et al. |
| 5,071,531 A | 12/1991 | Soane |
| 5,091,328 A | 2/1992 | Miller |
| D324,426 S | 3/1992 | Fan et al. |
| 5,096,669 A | 3/1992 | Lauks et al. |
| D325,638 S | 4/1992 | Sloat et al. |
| 5,126,002 A | 6/1992 | Iwata et al. |
| 5,126,022 A | 6/1992 | Soane et al. |
| D328,135 S | 7/1992 | Fan et al. |
| D328,794 S | 8/1992 | Frenkel et al. |
| 5,135,627 A | 8/1992 | Soane |
| 5,135,872 A | 8/1992 | Pouletty et al. |
| 5,147,606 A | 9/1992 | Charlton et al. |
| 5,169,512 A | 12/1992 | Wiedenmann et al. |
| D333,522 S | 2/1993 | Gianino |
| 5,186,339 A | 2/1993 | Heissler |
| 5,192,507 A | 3/1993 | Taylor et al. |
| 5,208,163 A | 5/1993 | Charlton et al. |
| 5,217,694 A | 6/1993 | Gibler et al. |
| 5,223,226 A | 6/1993 | Wittmer et al. |
| 5,229,297 A | 7/1993 | Schnipelsky et al. |
| D338,275 S | 8/1993 | Fischer et al. |
| 5,250,263 A | 10/1993 | Manz |
| 5,252,743 A | 10/1993 | Barrett et al. |
| 5,256,376 A | 10/1993 | Callan et al. |
| 5,275,787 A | 1/1994 | Yuguchi et al. |
| 5,282,950 A | 2/1994 | Dietze et al. |
| 5,296,375 A | 3/1994 | Kricka et al. |
| 5,304,477 A | 4/1994 | Nagoh et al. |
| 5,304,487 A | 4/1994 | Wilding et al. |
| D347,478 S | 5/1994 | Pinkney |
| 5,311,896 A | 5/1994 | Kaartinen |
| 5,311,996 A | 5/1994 | Duffy et al. |
| 5,316,727 A | 5/1994 | Suzuki et al. |
| 5,327,038 A | 7/1994 | Culp |
| 5,339,486 A | 8/1994 | Persic |
| D351,475 S | 10/1994 | Gerber |
| D351,913 S | 10/1994 | Hieb et al. |
| 5,364,591 A | 11/1994 | Green et al. |
| 5,372,946 A | 12/1994 | Cusak et al. |
| 5,374,395 A | 12/1994 | Robinson |
| 5,389,339 A | 2/1995 | Petschek et al. |
| D356,232 S | 3/1995 | Armstrong et al. |
| 5,397,709 A | 3/1995 | Berndt |
| 5,401,465 A | 3/1995 | Smethers et al. |
| 5,411,708 A | 5/1995 | Moscetta et al. |
| 5,414,245 A | 5/1995 | Hackleman |
| 5,415,839 A | 5/1995 | Zaun et al. |
| 5,416,000 A | 5/1995 | Allen et al. |
| 5,422,271 A | 6/1995 | Chen et al. |
| 5,422,284 A | 6/1995 | Lau |
| 5,427,946 A | 6/1995 | Kricka et al. |
| 5,443,791 A | 8/1995 | Cathcart et al. |
| 5,474,796 A | 12/1995 | Brennan |
| D366,116 S | 1/1996 | Biskupski |
| 5,486,335 A | 1/1996 | Wilding et al. |
| 5,494,639 A | 2/1996 | Grzegorzewski |
| 5,498,392 A | 3/1996 | Wilding et al. |
| 5,503,803 A | 4/1996 | Brown |
| 5,516,410 A | 5/1996 | Schneider et al. |
| 5,519,635 A | 5/1996 | Miyake et al. |
| 5,529,677 A | 6/1996 | Schneider et al. |
| 5,559,432 A | 9/1996 | Logue |
| 5,565,171 A | 10/1996 | Dovichi et al. |
| 5,569,364 A | 10/1996 | Hooper et al. |

(56) References Cited

U.S. PATENT DOCUMENTS

| | | | |
|---|---|---|---|
| 5,578,270 | A | 11/1996 | Reichler et al. |
| 5,578,818 | A | 11/1996 | Kain et al. |
| 5,579,928 | A | 12/1996 | Anukwuem |
| 5,580,523 | A | 12/1996 | Bard |
| 5,582,884 | A | 12/1996 | Ball et al. |
| 5,585,069 | A | 12/1996 | Zanzucchi et al. |
| 5,585,089 | A | 12/1996 | Queen et al. |
| 5,585,242 | A | 12/1996 | Bouma et al. |
| 5,587,128 | A | 12/1996 | Wilding et al. |
| 5,589,136 | A * | 12/1996 | Northrup ............. B01J 19/0046 422/129 |
| 5,593,838 | A | 1/1997 | Zanzucchi et al. |
| 5,595,708 | A | 1/1997 | Berndt |
| 5,599,432 | A | 2/1997 | Manz et al. |
| 5,599,503 | A | 2/1997 | Manz et al. |
| 5,599,667 | A | 2/1997 | Arnold, Jr. et al. |
| 5,601,727 | A | 2/1997 | Bormann et al. |
| 5,603,351 | A | 2/1997 | Cherukuri et al. |
| 5,605,662 | A | 2/1997 | Heller et al. |
| 5,609,910 | A | 3/1997 | Hackleman |
| D378,782 | S | 4/1997 | LaBarbera et al. |
| 5,628,890 | A | 5/1997 | Carter et al. |
| 5,630,920 | A | 5/1997 | Friese et al. |
| 5,631,337 | A | 5/1997 | Sassi et al. |
| 5,632,876 | A | 5/1997 | Zanzucchi et al. |
| 5,632,957 | A | 5/1997 | Heller et al. |
| 5,635,358 | A | 6/1997 | Wilding et al. |
| 5,637,469 | A | 6/1997 | Wilding et al. |
| 5,639,423 | A | 6/1997 | Northrup et al. |
| 5,639,428 | A | 6/1997 | Cottingham |
| 5,643,738 | A | 7/1997 | Zanzucchi et al. |
| 5,645,801 | A | 7/1997 | Bouma et al. |
| 5,646,039 | A | 7/1997 | Northrup et al. |
| 5,646,049 | A | 7/1997 | Tayi |
| 5,647,994 | A | 7/1997 | Tuunanen et al. |
| 5,651,839 | A | 7/1997 | Rauf |
| 5,652,141 | A | 7/1997 | Henco et al. |
| 5,652,149 | A | 7/1997 | Mileaf et al. |
| D382,346 | S | 8/1997 | Buhler et al. |
| D382,647 | S | 8/1997 | Staples et al. |
| 5,667,976 | A | 9/1997 | Van Ness et al. |
| 5,671,303 | A | 9/1997 | Shieh et al. |
| 5,674,394 | A | 10/1997 | Whitmore |
| 5,674,742 | A | 10/1997 | Northrup et al. |
| 5,681,484 | A | 10/1997 | Zanzucchi et al. |
| 5,681,529 | A | 10/1997 | Taguchi et al. |
| 5,683,657 | A | 11/1997 | Mian |
| 5,699,157 | A | 12/1997 | Parce |
| 5,700,637 | A | 12/1997 | Southern |
| 5,705,813 | A | 1/1998 | Apffel et al. |
| 5,721,136 | A | 2/1998 | Finney et al. |
| 5,725,831 | A | 3/1998 | Reichler et al. |
| 5,726,026 | A | 3/1998 | Wilding et al. |
| 5,726,404 | A | 3/1998 | Brody |
| 5,726,944 | A | 3/1998 | Pelley et al. |
| 5,731,212 | A | 3/1998 | Gavin et al. |
| 5,744,366 | A | 4/1998 | Kricka et al. |
| 5,746,978 | A | 5/1998 | Bienhaus et al. |
| 5,747,666 | A | 5/1998 | Willis |
| 5,750,015 | A | 5/1998 | Soane et al. |
| 5,755,942 | A | 5/1998 | Zanzucchi et al. |
| 5,762,874 | A | 6/1998 | Seaton et al. |
| 5,763,262 | A | 6/1998 | Wong et al. |
| 5,770,029 | A | 6/1998 | Nelson et al. |
| 5,770,388 | A | 6/1998 | Vorpahl |
| 5,772,966 | A | 6/1998 | Maracas et al. |
| 5,779,868 | A | 7/1998 | Parce et al. |
| 5,783,148 | A | 7/1998 | Cottingham et al. |
| 5,787,032 | A | 7/1998 | Heller et al. |
| 5,788,814 | A | 8/1998 | Sun et al. |
| 5,800,600 | A | 9/1998 | Lima-Marques et al. |
| 5,800,690 | A | 9/1998 | Chow et al. |
| 5,804,436 | A | 9/1998 | Okun et al. |
| D399,959 | S | 10/1998 | Prokop et al. |
| 5,827,481 | A | 10/1998 | Bente et al. |
| 5,842,106 | A | 11/1998 | Thaler et al. |
| 5,842,787 | A | 12/1998 | Kopf-Sill et al. |
| 5,846,396 | A | 12/1998 | Zanzucchi et al. |
| 5,846,493 | A | 12/1998 | Bankier et al. |
| 5,849,208 | A | 12/1998 | Hayes et al. |
| 5,849,486 | A | 12/1998 | Heller et al. |
| 5,849,489 | A | 12/1998 | Heller |
| 5,849,598 | A | 12/1998 | Wilson et al. |
| 5,852,495 | A | 12/1998 | Parce |
| 5,856,174 | A | 1/1999 | Lipshutz et al. |
| 5,858,187 | A | 1/1999 | Ramsey et al. |
| 5,858,188 | A | 1/1999 | Soane et al. |
| 5,863,502 | A | 1/1999 | Southgate et al. |
| 5,863,708 | A | 1/1999 | Zanzucchi et al. |
| 5,863,801 | A | 1/1999 | Southgate et al. |
| 5,866,345 | A | 2/1999 | Wilding et al. |
| 5,869,004 | A | 2/1999 | Parce et al. |
| 5,869,244 | A | 2/1999 | Martin et al. |
| 5,872,010 | A | 2/1999 | Karger et al. |
| 5,872,623 | A | 2/1999 | Stabile et al. |
| 5,874,046 | A | 2/1999 | Megerle |
| 5,876,675 | A | 3/1999 | Kennedy |
| 5,880,071 | A | 3/1999 | Parce et al. |
| 5,882,465 | A | 3/1999 | McReynolds |
| 5,883,211 | A | 3/1999 | Sassi et al. |
| 5,885,432 | A | 3/1999 | Hooper et al. |
| 5,885,470 | A | 3/1999 | Parce et al. |
| 5,895,762 | A | 4/1999 | Greenfield et al. |
| 5,900,130 | A | 5/1999 | Benregnu et al. |
| 5,912,124 | A | 6/1999 | Kumar |
| 5,912,134 | A | 6/1999 | Shartle |
| 5,914,229 | A | 6/1999 | Loewy |
| 5,916,522 | A | 6/1999 | Boyd et al. |
| 5,916,776 | A | 6/1999 | Kumar |
| 5,919,646 | A | 7/1999 | Okun et al. |
| 5,919,711 | A | 7/1999 | Boyd et al. |
| 5,922,591 | A | 7/1999 | Anderson et al. |
| 5,927,547 | A | 7/1999 | Papen et al. |
| 5,928,880 | A | 7/1999 | Wilding et al. |
| 5,929,208 | A | 7/1999 | Heller et al. |
| D413,391 | S | 8/1999 | Lapeus et al. |
| 5,932,799 | A | 8/1999 | Moles |
| 5,935,401 | A | 8/1999 | Amigo |
| 5,939,291 | A | 8/1999 | Loewy et al. |
| 5,942,443 | A | 8/1999 | Parce et al. |
| D413,677 | S | 9/1999 | Dumitrescu et al. |
| D414,271 | S | 9/1999 | Mendoza |
| 5,948,227 | A | 9/1999 | Dubrow |
| 5,948,363 | A | 9/1999 | Gaillard |
| 5,948,673 | A | 9/1999 | Cottingham |
| 5,955,028 | A | 9/1999 | Chow |
| 5,955,029 | A | 9/1999 | Wilding et al. |
| 5,957,579 | A | 9/1999 | Kopf-Sill et al. |
| 5,958,203 | A | 9/1999 | Parce et al. |
| 5,958,694 | A | 9/1999 | Nikiforov |
| 5,959,221 | A | 9/1999 | Boyd et al. |
| 5,959,291 | A | 9/1999 | Jensen |
| 5,964,995 | A | 10/1999 | Nikiforov et al. |
| 5,964,997 | A | 10/1999 | McBride |
| 5,965,001 | A | 10/1999 | Chow et al. |
| 5,965,410 | A | 10/1999 | Chow et al. |
| 5,965,886 | A | 10/1999 | Sauer et al. |
| 5,968,745 | A | 10/1999 | Thorp et al. |
| 5,972,187 | A | 10/1999 | Parce et al. |
| 5,973,138 | A | 10/1999 | Collis |
| D417,009 | S | 11/1999 | Boyd |
| 5,976,336 | A | 11/1999 | Dubrow et al. |
| 5,980,704 | A | 11/1999 | Cherukuri et al. |
| 5,980,719 | A | 11/1999 | Cherukuri et al. |
| 5,981,735 | A | 11/1999 | Thatcher et al. |
| 5,989,402 | A | 11/1999 | Chow et al. |
| 5,992,820 | A | 11/1999 | Fare et al. |
| 5,993,611 | A | 11/1999 | Moroney, III et al. |
| 5,993,750 | A | 11/1999 | Ghosh et al. |
| 5,997,708 | A | 12/1999 | Craig |
| 6,001,229 | A | 12/1999 | Ramsey |
| 6,001,231 | A | 12/1999 | Kopf-Sill |
| 6,001,307 | A | 12/1999 | Naka et al. |
| 6,004,515 | A | 12/1999 | Parce et al. |

(56) References Cited

U.S. PATENT DOCUMENTS

| | | |
|---|---|---|
| 6,007,690 A | 12/1999 | Nelson et al. |
| 6,010,607 A | 1/2000 | Ramsey |
| 6,010,608 A | 1/2000 | Ramsey |
| 6,010,627 A | 1/2000 | Hood, III |
| 6,012,902 A | 1/2000 | Parce |
| D420,747 S | 2/2000 | Dumitrescu et al. |
| D421,130 S | 2/2000 | Cohen et al. |
| 6,024,920 A | 2/2000 | Cunanan |
| D421,653 S | 3/2000 | Purcell |
| 6,033,546 A | 3/2000 | Ramsey |
| 6,033,880 A * | 3/2000 | Haff .................. B01J 19/0046 422/50 |
| 6,043,080 A | 3/2000 | Lipshutz et al. |
| 6,046,056 A | 4/2000 | Parce et al. |
| 6,048,734 A | 4/2000 | Burns et al. |
| 6,054,034 A | 4/2000 | Soane et al. |
| 6,054,277 A | 4/2000 | Furcht et al. |
| 6,056,860 A | 5/2000 | Amigo et al. |
| 6,057,149 A | 5/2000 | Burns et al. |
| 6,062,261 A | 5/2000 | Jacobson et al. |
| 6,063,341 A | 5/2000 | Fassbind et al. |
| 6,063,589 A | 5/2000 | Kellogg et al. |
| 6,068,752 A | 5/2000 | Dubrow et al. |
| 6,071,478 A | 6/2000 | Chow |
| 6,074,725 A | 6/2000 | Kennedy |
| 6,074,827 A | 6/2000 | Nelson et al. |
| D428,497 S | 7/2000 | Lapeus et al. |
| 6,086,740 A | 7/2000 | Kennedy |
| 6,096,509 A | 8/2000 | Okun et al. |
| 6,100,541 A | 8/2000 | Nagle et al. |
| 6,102,897 A | 8/2000 | Lang |
| 6,103,537 A | 8/2000 | Ullman et al. |
| 6,106,685 A | 8/2000 | McBride et al. |
| 6,110,343 A | 8/2000 | Ramsey et al. |
| 6,117,398 A | 9/2000 | Bienhaus et al. |
| 6,123,205 A | 9/2000 | Dumitrescu et al. |
| 6,123,798 A | 9/2000 | Gandhi et al. |
| 6,130,098 A | 10/2000 | Handique et al. |
| 6,132,580 A | 10/2000 | Mathies et al. |
| 6,132,684 A | 10/2000 | Marino |
| 6,133,436 A | 10/2000 | Koster et al. |
| D433,759 S | 11/2000 | Mathis et al. |
| 6,143,250 A | 11/2000 | Tajima |
| 6,149,787 A | 11/2000 | Chow et al. |
| 6,149,872 A | 11/2000 | Mack et al. |
| 6,156,199 A | 12/2000 | Zuk, Jr. |
| 6,158,269 A | 12/2000 | Dorenkott et al. |
| 6,167,910 B1 | 1/2001 | Chow |
| 6,168,948 B1 | 1/2001 | Anderson et al. |
| 6,171,850 B1 | 1/2001 | Nagle et al. |
| 6,174,675 B1 | 1/2001 | Chow |
| 6,180,950 B1 | 1/2001 | Olsen |
| D438,311 S | 2/2001 | Yamanishi et al. |
| 6,190,619 B1 | 2/2001 | Kilcoin et al. |
| D438,632 S | 3/2001 | Miller |
| D438,633 S | 3/2001 | Miller |
| D439,673 S | 3/2001 | Brophy et al. |
| 6,197,595 B1 | 3/2001 | Anderson et al. |
| 6,211,989 B1 | 4/2001 | Wulf et al. |
| 6,213,151 B1 | 4/2001 | Jacobson et al. |
| 6,221,600 B1 | 4/2001 | MacLeod et al. |
| 6,228,635 B1 | 5/2001 | Armstrong et al. |
| 6,232,072 B1 | 5/2001 | Fisher |
| 6,235,175 B1 | 5/2001 | Dubrow et al. |
| 6,235,313 B1 | 5/2001 | Mathiowitz et al. |
| 6,235,471 B1 | 5/2001 | Knapp et al. |
| 6,236,456 B1 | 5/2001 | Giebeler et al. |
| 6,236,581 B1 | 5/2001 | Foss et al. |
| 6,238,626 B1 | 5/2001 | Higuchi et al. |
| 6,251,343 B1 | 6/2001 | Dubrow et al. |
| 6,254,826 B1 | 7/2001 | Acosta et al. |
| 6,259,635 B1 | 7/2001 | Khouri et al. |
| 6,261,431 B1 | 7/2001 | Mathies et al. |
| 6,267,858 B1 | 7/2001 | Parce et al. |
| D446,306 S | 8/2001 | Ochi et al. |
| 6,271,021 B1 | 8/2001 | Burns et al. |
| 6,274,089 B1 | 8/2001 | Chow et al. |
| 6,280,967 B1 | 8/2001 | Ransom et al. |
| 6,281,008 B1 | 8/2001 | Komai et al. |
| 6,284,113 B1 | 9/2001 | Bjornson et al. |
| 6,284,470 B1 | 9/2001 | Bitner et al. |
| 6,287,254 B1 | 9/2001 | Dodds |
| 6,287,774 B1 | 9/2001 | Nikiforov |
| 6,291,248 B1 | 9/2001 | Haj-Ahmad |
| 6,294,063 B1 | 9/2001 | Becker et al. |
| 6,302,134 B1 | 10/2001 | Kellogg et al. |
| 6,302,304 B1 | 10/2001 | Spencer |
| 6,303,343 B1 | 10/2001 | Kopf-sill |
| 6,306,273 B1 | 10/2001 | Wainright et al. |
| 6,306,590 B1 | 10/2001 | Mehta et al. |
| 6,316,774 B1 | 11/2001 | Giebeler et al. |
| 6,319,469 B1 | 11/2001 | Mian et al. |
| 6,322,683 B1 | 11/2001 | Wolk et al. |
| 6,326,083 B1 | 12/2001 | Yang et al. |
| 6,326,147 B1 | 12/2001 | Oldham et al. |
| 6,326,211 B1 | 12/2001 | Anderson et al. |
| 6,334,980 B1 | 1/2002 | Hayes et al. |
| 6,337,435 B1 | 1/2002 | Chu et al. |
| 6,353,475 B1 | 3/2002 | Jensen et al. |
| 6,358,387 B1 | 3/2002 | Kopf-sill et al. |
| 6,366,924 B1 | 4/2002 | Parce |
| 6,368,561 B1 | 4/2002 | Rutishauser et al. |
| 6,368,871 B1 | 4/2002 | Christel et al. |
| 6,370,206 B1 | 4/2002 | Schenk |
| 6,375,185 B1 | 4/2002 | Lin |
| 6,375,901 B1 | 4/2002 | Robotti et al. |
| 6,379,884 B2 | 4/2002 | Wada et al. |
| 6,379,929 B1 | 4/2002 | Burns et al. |
| 6,379,974 B1 | 4/2002 | Parce et al. |
| 6,382,254 B1 | 5/2002 | Yang et al. |
| 6,391,541 B1 | 5/2002 | Petersen et al. |
| 6,391,623 B1 | 5/2002 | Besemer et al. |
| 6,395,161 B1 | 5/2002 | Schneider et al. |
| 6,398,956 B1 | 6/2002 | Coville et al. |
| 6,399,025 B1 | 6/2002 | Chow |
| 6,399,389 B1 | 6/2002 | Parce et al. |
| 6,399,952 B1 | 6/2002 | Maher et al. |
| 6,401,552 B1 | 6/2002 | Elkins |
| 6,403,338 B1 | 6/2002 | Knapp et al. |
| 6,408,878 B2 | 6/2002 | Unger et al. |
| 6,413,401 B1 | 7/2002 | Chow et al. |
| 6,416,642 B1 | 7/2002 | Alajoki et al. |
| 6,420,143 B1 | 7/2002 | Kopf-sill |
| 6,425,972 B1 | 7/2002 | McReynolds |
| D461,906 S | 8/2002 | Pham |
| 6,428,987 B2 | 8/2002 | Franzen |
| 6,430,512 B1 | 8/2002 | Gallagher |
| 6,432,366 B2 | 8/2002 | Ruediger et al. |
| 6,440,725 B1 | 8/2002 | Pourahmadi et al. |
| D463,031 S | 9/2002 | Slomski et al. |
| 6,444,461 B1 | 9/2002 | Knapp et al. |
| 6,447,661 B1 | 9/2002 | Chow et al. |
| 6,447,727 B1 | 9/2002 | Parce et al. |
| 6,448,064 B1 | 9/2002 | Vo-Dinh et al. |
| 6,453,928 B1 | 9/2002 | Kaplan et al. |
| 6,465,257 B1 | 10/2002 | Parce et al. |
| 6,468,761 B2 | 10/2002 | Yang et al. |
| 6,472,141 B2 | 10/2002 | Nikiforov |
| D466,219 S | 11/2002 | Wynschenk et al. |
| 6,475,364 B1 | 11/2002 | Dubrow et al. |
| D467,348 S | 12/2002 | McMichael et al. |
| D467,349 S | 12/2002 | Niedbala et al. |
| 6,488,897 B2 | 12/2002 | Dubrow et al. |
| 6,495,104 B1 | 12/2002 | Unno et al. |
| 6,498,497 B1 | 12/2002 | Chow et al. |
| 6,500,323 B1 | 12/2002 | Chow et al. |
| 6,500,390 B1 | 12/2002 | Boulton et al. |
| D468,437 S | 1/2003 | McMenamy et al. |
| 6,506,609 B1 | 1/2003 | Wada et al. |
| 6,509,193 B1 | 1/2003 | Tajima |
| 6,511,853 B1 | 1/2003 | Kopf-sill et al. |
| D470,595 S | 2/2003 | Crisanti et al. |
| 6,515,753 B2 | 2/2003 | Maher |
| 6,517,783 B2 | 2/2003 | Horner et al. |

(56) References Cited

U.S. PATENT DOCUMENTS

| | | |
|---|---|---|
| 6,520,197 B2 | 2/2003 | Deshmukh et al. |
| 6,521,188 B1 | 2/2003 | Webster |
| 6,524,456 B1 | 2/2003 | Ramsey et al. |
| 6,524,790 B1 | 2/2003 | Kopf-sill et al. |
| D472,324 S | 3/2003 | Rumore et al. |
| 6,534,295 B2 | 3/2003 | Tai et al. |
| 6,537,771 B1 | 3/2003 | Farinas et al. |
| 6,540,896 B1 | 4/2003 | Manz et al. |
| 6,544,734 B1 | 4/2003 | Briscoe et al. |
| 6,547,942 B1 | 4/2003 | Parce et al. |
| 6,555,389 B1 | 4/2003 | Ullman et al. |
| 6,556,923 B2 | 4/2003 | Gallagher et al. |
| D474,279 S | 5/2003 | Mayer et al. |
| D474,280 S | 5/2003 | Niedbala et al. |
| 6,558,916 B2 | 5/2003 | Veerapandian et al. |
| 6,558,945 B1 | 5/2003 | Kao |
| 6,569,607 B2 | 5/2003 | McReynolds |
| 6,572,830 B1 | 6/2003 | Burdon et al. |
| 6,575,188 B2 | 6/2003 | Parunak |
| 6,576,459 B2 | 6/2003 | Miles et al. |
| 6,579,453 B1 | 6/2003 | Bächler et al. |
| 6,589,729 B2 | 7/2003 | Chan et al. |
| 6,592,821 B1 | 7/2003 | Wada et al. |
| 6,597,450 B1 | 7/2003 | Andrews et al. |
| 6,602,474 B1 | 8/2003 | Tajima |
| 6,613,211 B1 | 9/2003 | McCormick et al. |
| 6,613,512 B1 | 9/2003 | Kopf-sill et al. |
| 6,613,580 B1 | 9/2003 | Chow et al. |
| 6,613,581 B1 | 9/2003 | Wada et al. |
| 6,614,030 B2 | 9/2003 | Maher et al. |
| 6,620,625 B2 | 9/2003 | Wolk et al. |
| 6,623,860 B2 | 9/2003 | Hu et al. |
| 6,627,406 B1 | 9/2003 | Singh et al. |
| D480,814 S | 10/2003 | Lafferty et al. |
| 6,632,655 B1 | 10/2003 | Mehta et al. |
| 6,633,785 B1 | 10/2003 | Kasahara et al. |
| D482,796 S | 11/2003 | Oyama et al. |
| 6,640,981 B2 | 11/2003 | Lafond et al. |
| 6,649,358 B1 | 11/2003 | Parce et al. |
| 6,664,104 B2 | 12/2003 | Pourahmadi et al. |
| 6,669,831 B2 | 12/2003 | Chow et al. |
| 6,670,153 B2 | 12/2003 | Stern |
| D484,989 S | 1/2004 | Gebrian |
| 6,672,458 B2 | 1/2004 | Hansen et al. |
| 6,681,616 B2 | 1/2004 | Spaid et al. |
| 6,681,788 B2 | 1/2004 | Parce et al. |
| 6,685,813 B2 | 2/2004 | Williams et al. |
| 6,692,700 B2 | 2/2004 | Handique |
| 6,695,009 B2 | 2/2004 | Chien et al. |
| 6,706,519 B1 | 3/2004 | Kellogg et al. |
| 6,720,148 B1 | 4/2004 | Nikiforov |
| 6,730,206 B2 | 5/2004 | Ricco et al. |
| 6,733,645 B1 | 5/2004 | Chow |
| 6,734,401 B2 | 5/2004 | Bedingham et al. |
| 6,737,026 B1 | 5/2004 | Bergh et al. |
| 6,740,518 B1 | 5/2004 | Duong et al. |
| D491,272 S | 6/2004 | Alden et al. |
| D491,273 S | 6/2004 | Biegler et al. |
| D491,276 S | 6/2004 | Langille |
| 6,750,661 B2 | 6/2004 | Brooks et al. |
| 6,752,966 B1 | 6/2004 | Chazan |
| 6,756,019 B1 | 6/2004 | Dubrow et al. |
| 6,764,859 B1 | 7/2004 | Kreuwel et al. |
| 6,766,817 B2 | 7/2004 | da Silva |
| 6,773,567 B1 | 8/2004 | Wolk |
| 6,777,184 B2 | 8/2004 | Nikiforov et al. |
| 6,783,962 B1 | 8/2004 | Olander et al. |
| D495,805 S | 9/2004 | Lea et al. |
| 6,787,015 B2 | 9/2004 | Lackritz et al. |
| 6,787,016 B2 | 9/2004 | Tan et al. |
| 6,787,111 B2 | 9/2004 | Roach et al. |
| 6,790,328 B2 | 9/2004 | Jacobson et al. |
| 6,790,330 B2 | 9/2004 | Gascoyne et al. |
| 6,811,668 B1 | 11/2004 | Berndt et al. |
| 6,818,113 B2 | 11/2004 | Williams et al. |
| 6,819,027 B2 | 11/2004 | Saraf |
| 6,824,663 B1 | 11/2004 | Boone |
| D499,813 S | 12/2004 | Wu |
| D500,142 S | 12/2004 | Crisanti et al. |
| D500,363 S | 12/2004 | Fanning et al. |
| 6,827,831 B1 | 12/2004 | Chow et al. |
| 6,827,906 B1 | 12/2004 | Bjornson et al. |
| 6,838,156 B1 | 1/2005 | Neyer et al. |
| 6,838,680 B2 | 1/2005 | Maher et al. |
| 6,852,287 B2 | 2/2005 | Ganesan |
| 6,858,185 B1 | 2/2005 | Kopf-sill et al. |
| 6,859,698 B2 | 2/2005 | Schmeisser |
| 6,861,035 B2 | 3/2005 | Pham et al. |
| 6,878,540 B2 | 4/2005 | Pourahmadi et al. |
| 6,878,755 B2 | 4/2005 | Singh et al. |
| 6,884,628 B2 | 4/2005 | Hubbell et al. |
| 6,887,693 B2 | 5/2005 | McMillan et al. |
| 6,893,879 B2 | 5/2005 | Petersen et al. |
| 6,900,889 B2 | 5/2005 | Bjornson et al. |
| 6,905,583 B2 | 6/2005 | Wainright et al. |
| 6,905,612 B2 | 6/2005 | Dorian et al. |
| 6,906,797 B1 | 6/2005 | Kao et al. |
| 6,908,594 B1 | 6/2005 | Schaevitz et al. |
| 6,911,183 B1 | 6/2005 | Handique et al. |
| 6,914,137 B2 | 7/2005 | Baker |
| 6,915,679 B2 | 7/2005 | Chien et al. |
| 6,918,404 B2 | 7/2005 | Dias da Silva |
| D508,999 S | 8/2005 | Fanning et al. |
| 6,939,451 B2 | 9/2005 | Zhao et al. |
| 6,942,771 B1 | 9/2005 | Kayyem |
| 6,958,392 B2 | 10/2005 | Fomovskaia et al. |
| D512,155 S | 11/2005 | Matsumoto |
| 6,964,747 B2 | 11/2005 | Banerjee et al. |
| 6,977,163 B1 | 12/2005 | Mehta |
| 6,984,516 B2 | 1/2006 | Briscoe et al. |
| D515,707 S | 2/2006 | Sinohara et al. |
| D516,221 S | 2/2006 | Wohlstadter et al. |
| 7,001,853 B1 | 2/2006 | Brown et al. |
| 7,004,184 B2 | 2/2006 | Handique et al. |
| D517,554 S | 3/2006 | Yanagisawa et al. |
| 7,010,391 B2 | 3/2006 | Handique et al. |
| 7,023,007 B2 | 4/2006 | Gallagher |
| 7,024,281 B1 | 4/2006 | Unno |
| 7,036,667 B2 | 5/2006 | Greenstein et al. |
| 7,037,416 B2 | 5/2006 | Parce et al. |
| 7,038,472 B1 | 5/2006 | Chien |
| 7,039,527 B2 | 5/2006 | Tripathi et al. |
| 7,040,144 B2 | 5/2006 | Spaid et al. |
| 7,049,558 B2 | 5/2006 | Baer et al. |
| D523,153 S | 6/2006 | Akashi et al. |
| 7,055,695 B2 | 6/2006 | Greenstein et al. |
| 7,060,171 B1 | 6/2006 | Nikiforov et al. |
| 7,066,586 B2 | 6/2006 | da Silva |
| 7,069,952 B1 | 7/2006 | McReynolds et al. |
| 7,099,778 B2 | 8/2006 | Chien |
| D528,215 S | 9/2006 | Malmsater |
| 7,101,467 B2 | 9/2006 | Spaid |
| 7,105,304 B1 | 9/2006 | Nikiforov et al. |
| D531,321 S | 10/2006 | Godfrey et al. |
| 7,118,910 B2 | 10/2006 | Unger et al. |
| 7,138,032 B2 | 11/2006 | Gandhi et al. |
| D534,280 S | 12/2006 | Gomm et al. |
| 7,148,043 B2 | 12/2006 | Kordunsky et al. |
| 7,150,814 B1 | 12/2006 | Parce et al. |
| 7,150,999 B1 | 12/2006 | Shuck |
| D535,403 S | 1/2007 | Isozaki et al. |
| 7,160,423 B2 | 1/2007 | Chien et al. |
| 7,161,356 B1 | 1/2007 | Chien |
| 7,169,277 B2 | 1/2007 | Ausserer et al. |
| 7,169,618 B2 | 1/2007 | Skould |
| D537,951 S | 3/2007 | Okamoto et al. |
| D538,436 S | 3/2007 | Patadia et al. |
| 7,192,557 B2 | 3/2007 | Wu et al. |
| 7,195,986 B1 | 3/2007 | Bousse et al. |
| 7,205,154 B2 | 4/2007 | Corson |
| 7,208,125 B1 | 4/2007 | Dong |
| 7,235,406 B1 | 6/2007 | Woudenberg et al. |
| 7,247,274 B1 | 7/2007 | Chow |
| D548,841 S | 8/2007 | Brownell et al. |

(56) References Cited

U.S. PATENT DOCUMENTS

| | | |
|---|---|---|
| D549,827 S | 8/2007 | Maeno et al. |
| 7,252,928 B1 | 8/2007 | Hafeman et al. |
| 7,270,786 B2 | 9/2007 | Parunak et al. |
| D554,069 S | 10/2007 | Bolotin et al. |
| D554,070 S | 10/2007 | Bolotin et al. |
| 7,276,208 B2 | 10/2007 | Sevigny et al. |
| 7,276,330 B2 | 10/2007 | Chow et al. |
| 7,288,228 B2 | 10/2007 | Lefebvre |
| D556,914 S | 12/2007 | Okamoto et al. |
| 7,303,727 B1 | 12/2007 | Dubrow et al. |
| D559,995 S | 1/2008 | Handique et al. |
| 7,323,140 B2 | 1/2008 | Handique et al. |
| 7,332,130 B2 | 2/2008 | Handique |
| 7,338,760 B2 | 3/2008 | Gong et al. |
| D566,291 S | 4/2008 | Parunak et al. |
| 7,351,377 B2 | 4/2008 | Chazan et al. |
| D569,526 S | 5/2008 | Duffy et al. |
| 7,374,949 B2 | 5/2008 | Kuriger |
| 7,390,460 B2 | 6/2008 | Osawa et al. |
| 7,419,784 B2 | 9/2008 | Dubrow et al. |
| 7,422,669 B2 | 9/2008 | Jacobson et al. |
| 7,440,684 B2 | 10/2008 | Spaid et al. |
| 7,476,313 B2 | 1/2009 | Siddiqi |
| 7,480,042 B1 | 1/2009 | Phillips et al. |
| 7,494,577 B2 | 2/2009 | Williams et al. |
| 7,494,770 B2 | 2/2009 | Wilding et al. |
| 7,514,046 B2 | 4/2009 | Kechagia et al. |
| 7,518,726 B2 | 4/2009 | Rulison et al. |
| 7,521,186 B2 | 4/2009 | Burd Mehta |
| 7,527,769 B2 | 5/2009 | Bunch et al. |
| D595,423 S | 6/2009 | Johansson et al. |
| 7,553,671 B2 | 6/2009 | Sinclair et al. |
| D596,312 S | 7/2009 | Giraud et al. |
| D598,566 S | 8/2009 | Allaer |
| D599,234 S | 9/2009 | Ito |
| 7,595,197 B2 | 9/2009 | Brasseur |
| 7,604,938 B2 | 10/2009 | Takahashi et al. |
| 7,635,588 B2 | 12/2009 | King et al. |
| 7,645,581 B2 | 1/2010 | Knapp et al. |
| 7,670,559 B2 | 3/2010 | Chien et al. |
| 7,674,431 B2 | 3/2010 | Ganesan |
| 7,704,735 B2 | 4/2010 | Facer et al. |
| 7,723,123 B1 | 5/2010 | Murphy et al. |
| D618,820 S | 6/2010 | Wilson et al. |
| 7,727,371 B2 | 6/2010 | Kennedy et al. |
| 7,727,477 B2 | 6/2010 | Boronkay et al. |
| 7,744,817 B2 | 6/2010 | Bui |
| D621,060 S | 8/2010 | Handique |
| D628,305 S | 11/2010 | Gorrec et al. |
| 7,867,776 B2 | 1/2011 | Kennedy et al. |
| D632,799 S | 2/2011 | Canner et al. |
| 7,892,819 B2 | 2/2011 | Wilding et al. |
| D637,737 S | 5/2011 | Wilson et al. |
| 7,955,864 B2 | 6/2011 | Cox et al. |
| 7,998,708 B2 | 8/2011 | Handique et al. |
| 8,071,056 B2 | 12/2011 | Burns et al. |
| 8,088,616 B2 | 1/2012 | Handique |
| 8,105,783 B2 | 1/2012 | Handique |
| 8,110,158 B2 | 2/2012 | Handique |
| 8,133,671 B2 | 3/2012 | Williams et al. |
| 8,182,763 B2 | 5/2012 | Duffy et al. |
| 8,246,919 B2 | 8/2012 | Herchenbach et al. |
| 8,273,308 B2 | 9/2012 | Handique et al. |
| D669,597 S | 10/2012 | Cavada et al. |
| 8,287,820 B2 | 10/2012 | Williams et al. |
| 8,323,584 B2 | 12/2012 | Ganesan |
| 8,323,900 B2 | 12/2012 | Handique et al. |
| 8,324,372 B2 | 12/2012 | Brahmasandra et al. |
| 8,415,103 B2 | 4/2013 | Handique |
| 8,420,015 B2 | 4/2013 | Ganesan et al. |
| 8,440,149 B2 | 5/2013 | Handique |
| 8,470,586 B2 | 6/2013 | Wu et al. |
| 8,473,104 B2 | 6/2013 | Handique et al. |
| D686,749 S | 7/2013 | Trump |
| D692,162 S | 10/2013 | Lentz et al. |
| 8,679,831 B2 | 3/2014 | Handique et al. |
| D702,854 S | 4/2014 | Nakahana et al. |
| 8,685,341 B2 | 4/2014 | Ganesan |
| 8,703,069 B2 | 4/2014 | Handique et al. |
| 8,709,787 B2 | 4/2014 | Handique |
| 8,710,211 B2 | 4/2014 | Brahmasandra et al. |
| 8,734,733 B2 | 5/2014 | Handique |
| D710,024 S | 7/2014 | Guo |
| 8,765,076 B2 | 7/2014 | Handique et al. |
| 8,852,862 B2 | 10/2014 | Wu et al. |
| 8,883,490 B2 | 11/2014 | Handique et al. |
| 8,894,947 B2 | 11/2014 | Ganesan et al. |
| 8,895,311 B1 | 11/2014 | Handique et al. |
| D729,404 S | 5/2015 | Teich et al. |
| 9,028,773 B2 | 5/2015 | Ganesan |
| 9,040,288 B2 | 5/2015 | Handique et al. |
| 9,051,604 B2 | 6/2015 | Handique |
| 9,080,207 B2 | 7/2015 | Handique et al. |
| D742,027 S | 10/2015 | Lentz et al. |
| 9,186,677 B2 | 11/2015 | Williams et al. |
| 9,217,143 B2 | 12/2015 | Brahmasandra et al. |
| 9,222,954 B2 | 12/2015 | Lentz et al. |
| 9,238,223 B2 | 1/2016 | Handique |
| 9,259,734 B2 | 2/2016 | Williams et al. |
| 9,259,735 B2 | 2/2016 | Handique et al. |
| 9,347,586 B2 | 5/2016 | Williams et al. |
| 9,480,983 B2 | 11/2016 | Lentz et al. |
| 9,528,142 B2 | 12/2016 | Handique |
| 2001/0005489 A1 | 6/2001 | Roach et al. |
| 2001/0012492 A1 | 8/2001 | Acosta et al. |
| 2001/0016358 A1 | 8/2001 | Osawa et al. |
| 2001/0021355 A1 | 9/2001 | Baugh et al. |
| 2001/0023848 A1 | 9/2001 | Gjerde et al. |
| 2001/0038450 A1 | 11/2001 | McCaffrey et al. |
| 2001/0046702 A1 | 11/2001 | Schembri |
| 2001/0048899 A1 | 12/2001 | Marouiss et al. |
| 2001/0055765 A1 | 12/2001 | O'Keefe et al. |
| 2002/0001848 A1 | 1/2002 | Bedingham et al. |
| 2002/0008053 A1 | 1/2002 | Hansen et al. |
| 2002/0009015 A1 | 1/2002 | Laugharn, Jr. et al. |
| 2002/0014443 A1 | 2/2002 | Hansen et al. |
| 2002/0015667 A1 | 2/2002 | Chow |
| 2002/0021983 A1 | 2/2002 | Comte et al. |
| 2002/0037499 A1 | 3/2002 | Quake et al. |
| 2002/0039783 A1 | 4/2002 | McMillan et al. |
| 2002/0053399 A1 | 5/2002 | Soane et al. |
| 2002/0054835 A1 | 5/2002 | Robotti et al. |
| 2002/0055167 A1 | 5/2002 | Pourahmadi et al. |
| 2002/0058332 A1 | 5/2002 | Quake et al. |
| 2002/0060156 A1 | 5/2002 | Mathies et al. |
| 2002/0068357 A1 | 6/2002 | Mathies et al. |
| 2002/0068821 A1 | 6/2002 | Gundling |
| 2002/0131903 A1 | 9/2002 | Ingenhoven et al. |
| 2002/0141903 A1 | 10/2002 | Parunak et al. |
| 2002/0142471 A1 | 10/2002 | Handique et al. |
| 2002/0143297 A1 | 10/2002 | Francavilla et al. |
| 2002/0143437 A1 | 10/2002 | Handique et al. |
| 2002/0155010 A1 | 10/2002 | Karp et al. |
| 2002/0155477 A1 | 10/2002 | Ito |
| 2002/0169518 A1 | 11/2002 | Luoma et al. |
| 2002/0187557 A1 | 12/2002 | Hobbs et al. |
| 2002/0192808 A1* | 12/2002 | Gambini et al. ............ 435/287.2 |
| 2003/0008308 A1 | 1/2003 | Enzelberger et al. |
| 2003/0019522 A1 | 1/2003 | Parunak |
| 2003/0022392 A1 | 1/2003 | Hudak |
| 2003/0049174 A1 | 3/2003 | Ganesan |
| 2003/0049833 A1 | 3/2003 | Chen et al. |
| 2003/0059823 A1 | 3/2003 | Matsunaga et al. |
| 2003/0064507 A1 | 4/2003 | Gallagher et al. |
| 2003/0070677 A1 | 4/2003 | Handique et al. |
| 2003/0072683 A1 | 4/2003 | Stewart et al. |
| 2003/0073106 A1 | 4/2003 | Johansen et al. |
| 2003/0083686 A1 | 5/2003 | Freeman et al. |
| 2003/0087300 A1 | 5/2003 | Knapp et al. |
| 2003/0096310 A1 | 5/2003 | Hansen et al. |
| 2003/0099954 A1 | 5/2003 | Miltenyi et al. |
| 2003/0127327 A1 | 7/2003 | Kurnik |
| 2003/0136679 A1 | 7/2003 | Bohn et al. |
| 2003/0156991 A1 | 8/2003 | Halas et al. |

(56) References Cited

U.S. PATENT DOCUMENTS

| | | |
|---|---|---|
| 2003/0186295 A1 | 10/2003 | Colin et al. |
| 2003/0190608 A1 | 10/2003 | Blackburn et al. |
| 2003/0199081 A1 | 10/2003 | Wilding et al. |
| 2003/0211517 A1 | 11/2003 | Carulli et al. |
| 2004/0014202 A1 | 1/2004 | King et al. |
| 2004/0014238 A1 | 1/2004 | Krug et al. |
| 2004/0018116 A1 | 1/2004 | Desmond et al. |
| 2004/0018119 A1 | 1/2004 | Massaro |
| 2004/0022689 A1 | 2/2004 | Wulf et al. |
| 2004/0029258 A1 | 2/2004 | Heaney et al. |
| 2004/0029260 A1 | 2/2004 | Hansen et al. |
| 2004/0037739 A1 | 2/2004 | McNeely et al. |
| 2004/0053290 A1 | 3/2004 | Terbrueggen et al. |
| 2004/0063217 A1 | 4/2004 | Webster et al. |
| 2004/0065655 A1 | 4/2004 | Brown |
| 2004/0072278 A1 | 4/2004 | Chou et al. |
| 2004/0072375 A1 | 4/2004 | Gjerde et al. |
| 2004/0086427 A1 | 5/2004 | Childers et al. |
| 2004/0086956 A1 | 5/2004 | Bachur |
| 2004/0141887 A1 | 7/2004 | Mainquist et al. |
| 2004/0151629 A1 | 8/2004 | Pease et al. |
| 2004/0157220 A1 | 8/2004 | Kurnool et al. |
| 2004/0161788 A1 | 8/2004 | Chen et al. |
| 2004/0189311 A1 | 9/2004 | Glezer et al. |
| 2004/0200909 A1 | 10/2004 | McMillan et al. |
| 2004/0209331 A1 | 10/2004 | Ririe |
| 2004/0209354 A1 | 10/2004 | Mathies et al. |
| 2004/0219070 A1 | 11/2004 | Handique |
| 2004/0224317 A1 | 11/2004 | Kordunsky et al. |
| 2004/0235154 A1 | 11/2004 | Oh et al. |
| 2004/0240097 A1 | 12/2004 | Evans |
| 2005/0009174 A1 | 1/2005 | Nikiforov et al. |
| 2005/0013737 A1 | 1/2005 | Chow et al. |
| 2005/0037471 A1 | 2/2005 | Liu et al. |
| 2005/0041525 A1 | 2/2005 | Pugia et al. |
| 2005/0042639 A1 | 2/2005 | Knapp et al. |
| 2005/0048540 A1 | 3/2005 | Inami et al. |
| 2005/0058574 A1 | 3/2005 | Bysouth et al. |
| 2005/0058577 A1 | 3/2005 | Micklash et al. |
| 2005/0064535 A1 | 3/2005 | Favuzzi et al. |
| 2005/0069898 A1 | 3/2005 | Moon et al. |
| 2005/0084424 A1 | 4/2005 | Ganesan et al. |
| 2005/0106066 A1 | 5/2005 | Saltsman et al. |
| 2005/0121324 A1 | 6/2005 | Park et al. |
| 2005/0129580 A1 | 6/2005 | Swinehart et al. |
| 2005/0133370 A1 | 6/2005 | Park et al. |
| 2005/0135655 A1 | 6/2005 | Kopf-sill et al. |
| 2005/0142036 A1 | 6/2005 | Kim et al. |
| 2005/0152808 A1 | 7/2005 | Ganesan |
| 2005/0158781 A1 | 7/2005 | Woudenberg et al. |
| 2005/0170362 A1 | 8/2005 | Wada et al. |
| 2005/0186585 A1 | 8/2005 | Juncosa et al. |
| 2005/0196321 A1 | 9/2005 | Huang |
| 2005/0202470 A1 | 9/2005 | Sundberg et al. |
| 2005/0202504 A1 | 9/2005 | Anderson et al. |
| 2005/0208676 A1 | 9/2005 | Kahatt |
| 2005/0214172 A1 | 9/2005 | Burgisser |
| 2005/0220675 A1 | 10/2005 | Reed et al. |
| 2005/0227269 A1 | 10/2005 | Lloyd et al. |
| 2005/0233370 A1 | 10/2005 | Ammann et al. |
| 2005/0238545 A1 | 10/2005 | Parce et al. |
| 2005/0272079 A1 | 12/2005 | Burns et al. |
| 2006/0041058 A1 | 2/2006 | Yin et al. |
| 2006/0057039 A1 | 3/2006 | Morse et al. |
| 2006/0057629 A1 | 3/2006 | Kim |
| 2006/0062696 A1 | 3/2006 | Chow et al. |
| 2006/0094108 A1 | 5/2006 | Yoder et al. |
| 2006/0113190 A1 | 6/2006 | Kurnik |
| 2006/0133965 A1 | 6/2006 | Tajima et al. |
| 2006/0134790 A1 | 6/2006 | Tanaka et al. |
| 2006/0148063 A1 | 7/2006 | Fauzzi et al. |
| 2006/0165558 A1 | 7/2006 | Witty et al. |
| 2006/0165559 A1 | 7/2006 | Greenstein et al. |
| 2006/0166233 A1 | 7/2006 | Wu et al. |
| 2006/0177376 A1 | 8/2006 | Tomalia et al. |
| 2006/0177855 A1 | 8/2006 | Utermohlen et al. |
| 2006/0183216 A1 | 8/2006 | Handique |
| 2006/0201887 A1 | 9/2006 | Siddiqi |
| 2006/0205085 A1 | 9/2006 | Handique |
| 2006/0207944 A1 | 9/2006 | Siddiqi |
| 2006/0210435 A1 | 9/2006 | Alavie et al. |
| 2006/0223169 A1* | 10/2006 | Bedingham .......... G01N 21/645 435/287.2 |
| 2006/0246493 A1 | 11/2006 | Jensen et al. |
| 2006/0246533 A1 | 11/2006 | Fathollahi et al. |
| 2006/0269641 A1 | 11/2006 | Atwood et al. |
| 2006/0269961 A1 | 11/2006 | Fukushima et al. |
| 2007/0004028 A1 | 1/2007 | Lair et al. |
| 2007/0009386 A1 | 1/2007 | Padmanabhan et al. |
| 2007/0020699 A1 | 1/2007 | Carpenter et al. |
| 2007/0020764 A1 | 1/2007 | Miller |
| 2007/0026421 A1 | 2/2007 | Sundberg et al. |
| 2007/0042441 A1 | 2/2007 | Masters et al. |
| 2007/0054413 A1 | 3/2007 | Aviles et al. |
| 2007/0077648 A1 | 4/2007 | Okamoto et al. |
| 2007/0092901 A1 | 4/2007 | Ligler et al. |
| 2007/0098600 A1 | 5/2007 | Kayyem et al. |
| 2007/0099200 A1 | 5/2007 | Chow et al. |
| 2007/0104617 A1 | 5/2007 | Coulling et al. |
| 2007/0116613 A1 | 5/2007 | Elsener |
| 2007/0154895 A1 | 7/2007 | Spaid et al. |
| 2007/0177147 A1 | 8/2007 | Parce |
| 2007/0178607 A1 | 8/2007 | Prober et al. |
| 2007/0184463 A1 | 8/2007 | Molho et al. |
| 2007/0184547 A1 | 8/2007 | Handique et al. |
| 2007/0196237 A1 | 8/2007 | Neuzil et al. |
| 2007/0196238 A1 | 8/2007 | Kennedy et al. |
| 2007/0199821 A1 | 8/2007 | Chow |
| 2007/0215554 A1 | 9/2007 | Kreuwel et al. |
| 2007/0218459 A1 | 9/2007 | Miller et al. |
| 2007/0231213 A1 | 10/2007 | Prabhu et al. |
| 2007/0243626 A1 | 10/2007 | Windeyer et al. |
| 2007/0261479 A1 | 11/2007 | Spaid et al. |
| 2007/0269861 A1 | 11/2007 | Williams et al. |
| 2007/0292941 A1 | 12/2007 | Handique et al. |
| 2008/0000774 A1 | 1/2008 | Park et al. |
| 2008/0003649 A1* | 1/2008 | Maltezos et al. ............ 435/91.2 |
| 2008/0017306 A1 | 1/2008 | Liu et al. |
| 2008/0050804 A1 | 2/2008 | Handique et al. |
| 2008/0056948 A1 | 3/2008 | Dale et al. |
| 2008/0069729 A1 | 3/2008 | McNeely |
| 2008/0075634 A1 | 3/2008 | Herchenbach et al. |
| 2008/0090244 A1 | 4/2008 | Knapp et al. |
| 2008/0095673 A1 | 4/2008 | Xu |
| 2008/0118987 A1 | 5/2008 | Eastwood et al. |
| 2008/0124723 A1 | 5/2008 | Dale et al. |
| 2008/0149840 A1 | 6/2008 | Handique et al. |
| 2008/0160601 A1 | 7/2008 | Handique |
| 2008/0176230 A1 | 7/2008 | Owen et al. |
| 2008/0182301 A1 | 7/2008 | Handique et al. |
| 2008/0192254 A1 | 8/2008 | Kim et al. |
| 2008/0226502 A1 | 9/2008 | Jonsmann et al. |
| 2008/0247914 A1 | 10/2008 | Edens et al. |
| 2008/0262213 A1 | 10/2008 | Wu et al. |
| 2008/0308500 A1 | 12/2008 | Brassard |
| 2009/0047180 A1 | 2/2009 | Kawahara |
| 2009/0047713 A1 | 2/2009 | Handique |
| 2009/0066339 A1 | 3/2009 | Glezer et al. |
| 2009/0129978 A1 | 5/2009 | Wilson et al. |
| 2009/0130719 A1 | 5/2009 | Handique |
| 2009/0130745 A1 | 5/2009 | Williams et al. |
| 2009/0131650 A1 | 5/2009 | Brahmasandra et al. |
| 2009/0134069 A1 | 5/2009 | Handique |
| 2009/0136385 A1 | 5/2009 | Handique et al. |
| 2009/0136386 A1 | 5/2009 | Duffy et al. |
| 2009/0155123 A1 | 6/2009 | Williams et al. |
| 2009/0189089 A1 | 7/2009 | Bedingham et al. |
| 2009/0221059 A1 | 9/2009 | Williams et al. |
| 2009/0223925 A1 | 9/2009 | Morse et al. |
| 2010/0009351 A1 | 1/2010 | Brahmasandra et al. |
| 2010/0173393 A1 | 7/2010 | Handique et al. |
| 2010/0284864 A1 | 11/2010 | Holenstein et al. |
| 2011/0008825 A1 | 1/2011 | Ingber et al. |
| 2011/0027151 A1 | 2/2011 | Handique et al. |

(56) References Cited

U.S. PATENT DOCUMENTS

| | | | |
|---|---|---|---|
| 2011/0158865 A1 | 6/2011 | Miller et al. |
| 2011/0207140 A1 | 8/2011 | Handique et al. |
| 2011/0210257 A9 | 9/2011 | Handique et al. |
| 2012/0022695 A1 | 1/2012 | Handique et al. |
| 2012/0085416 A1 | 4/2012 | Ganesan |
| 2012/0122108 A1 | 5/2012 | Handique |
| 2012/0122231 A1 | 5/2012 | Tajima |
| 2012/0160826 A1 | 6/2012 | Handique |
| 2012/0171759 A1 | 7/2012 | Williams et al. |
| 2012/0183454 A1 | 7/2012 | Handique |
| 2012/0258463 A1 | 10/2012 | Duffy et al. |
| 2013/0037564 A1 | 2/2013 | Williams et al. |
| 2013/0071851 A1 | 3/2013 | Handique et al. |
| 2013/0101990 A1 | 4/2013 | Handique et al. |
| 2013/0164832 A1 | 6/2013 | Ganesan et al. |
| 2013/0183769 A1 | 7/2013 | Tajima |
| 2013/0217013 A1 | 8/2013 | Steel et al. |
| 2013/0217102 A1 | 8/2013 | Ganesan et al. |
| 2013/0251602 A1 | 9/2013 | Handique et al. |
| 2013/0280131 A1 | 10/2013 | Handique et al. |
| 2013/0288358 A1 | 10/2013 | Handique et al. |
| 2013/0315800 A1 | 11/2013 | Yin et al. |
| 2014/0030798 A1 | 1/2014 | Wu et al. |
| 2014/0045186 A1 | 2/2014 | Gubatayao et al. |
| 2014/0206088 A1 | 7/2014 | Lentz et al. |
| 2014/0212882 A1 | 7/2014 | Handique et al. |
| 2014/0227710 A1 | 8/2014 | Handique et al. |
| 2014/0297047 A1 | 10/2014 | Ganesan et al. |
| 2014/0323357 A1 | 10/2014 | Handique et al. |
| 2014/0323711 A1 | 10/2014 | Brahmasandra et al. |
| 2014/0329301 A1 | 11/2014 | Handique et al. |
| 2014/0342352 A1 | 11/2014 | Handique et al. |
| 2014/0377850 A1 | 12/2014 | Handique et al. |
| 2015/0064702 A1 | 3/2015 | Handique et al. |
| 2015/0118684 A1 | 4/2015 | Wu et al. |
| 2015/0133345 A1 | 5/2015 | Handique et al. |
| 2015/0142186 A1 | 5/2015 | Handique et al. |
| 2015/0152477 A1 | 6/2015 | Ganesan et al. |
| 2015/0174579 A1 | 6/2015 | Iten et al. |
| 2015/0315631 A1 | 11/2015 | Handique et al. |
| 2015/0328638 A1 | 11/2015 | Handique et al. |
| 2015/0376682 A1 | 12/2015 | Handique |
| 2016/0102305 A1 | 4/2016 | Brahmasandra et al. |
| 2016/0107161 A1 | 4/2016 | Lentz et al. |
| 2016/0250635 A1 | 9/2016 | Handique |
| 2016/0250640 A1 | 9/2016 | Williams et al. |
| 2016/0333337 A1 | 11/2016 | Duffy et al. |

FOREIGN PATENT DOCUMENTS

| | | |
|---|---|---|
| CN | 103540518 | 1/2014 |
| DE | 19929734 | 12/1999 |
| DE | 19833293 C1 | 1/2000 |
| EP | 0365828 A2 | 5/1990 |
| EP | 0483620 A2 | 5/1992 |
| EP | 0688602 A2 | 12/1995 |
| EP | 0766256 | 4/1997 |
| EP | 1077086 A2 | 2/2001 |
| EP | 1346772 A2 | 9/2003 |
| EP | 1541237 A2 | 6/2005 |
| EP | 1574586 A2 | 9/2005 |
| EP | 1792656 A1 | 6/2007 |
| EP | 2372367 A1 | 10/2011 |
| FR | 2672301 | 8/1992 |
| FR | 2795426 | 12/2000 |
| GB | 2453432 A | 4/2009 |
| JP | 58212921 A | 12/1983 |
| JP | S62-119460 | 5/1987 |
| JP | H01-502319 | 8/1989 |
| JP | 03-054470 | 3/1991 |
| JP | H 03181853 | 8/1991 |
| JP | 04-053555 U | 5/1992 |
| JP | 06-064156 U | 9/1994 |
| JP | 07-020010 | 1/1995 |
| JP | H07-290706 | 11/1995 |
| JP | H08-122336 | 5/1996 |
| JP | H08-211071 | 8/1996 |
| JP | H08-285859 | 11/1996 |
| JP | H09-325151 | 12/1997 |
| JP | 2001-502790 | 1/1998 |
| JP | H11-501504 | 2/1999 |
| JP | H 11503315 | 3/1999 |
| JP | 2000-514928 | 4/1999 |
| JP | H 11316226 | 11/1999 |
| JP | H11-515106 | 12/1999 |
| JP | 2000-180455 | 6/2000 |
| JP | 2000-275255 | 10/2000 |
| JP | 2001-502319 | 2/2001 |
| JP | 2001-204462 | 7/2001 |
| JP | 2001-509437 | 7/2001 |
| JP | 3191150 B2 | 7/2001 |
| JP | 2001-515216 | 9/2001 |
| JP | 2001-523813 | 11/2001 |
| JP | 2001-527220 | 12/2001 |
| JP | 2002-085961 | 3/2002 |
| JP | 2002-517735 | 6/2002 |
| JP | 2002-215241 | 7/2002 |
| JP | 2002-540382 | 11/2002 |
| JP | 2002-544476 | 12/2002 |
| JP | 2003-500674 | 1/2003 |
| JP | 2003-047839 A | 2/2003 |
| JP | 2003-047840 A | 2/2003 |
| JP | 2003-516125 | 5/2003 |
| JP | 2003-164279 | 6/2003 |
| JP | 2003-185584 | 7/2003 |
| JP | 2003-299485 | 10/2003 |
| JP | 2003-329693 | 11/2003 |
| JP | 2003-329696 | 11/2003 |
| JP | 2004-506179 A | 2/2004 |
| JP | 2004-150797 A | 5/2004 |
| JP | 2004-531360 A | 10/2004 |
| JP | 2004-533838 | 11/2004 |
| JP | 2004-361421 | 12/2004 |
| JP | 2004-536291 | 12/2004 |
| JP | 2005-009870 | 1/2005 |
| JP | 2005-010179 | 1/2005 |
| JP | 2005-511264 | 4/2005 |
| JP | 2005-514718 | 5/2005 |
| JP | 2005-176613 A | 7/2005 |
| JP | 2005-192439 | 7/2005 |
| JP | 2005-192554 | 7/2005 |
| JP | 2005-204661 | 8/2005 |
| JP | 2005-525816 | 9/2005 |
| JP | 2005-291954 A | 10/2005 |
| JP | 2005-323519 | 11/2005 |
| JP | 2006-021156 A | 1/2006 |
| JP | 2006-094866 A | 4/2006 |
| JP | 2006-145458 | 6/2006 |
| JP | 2006-167569 | 6/2006 |
| JP | 2007-074960 | 3/2007 |
| JP | 2007-097477 | 4/2007 |
| JP | 2007-101364 | 4/2007 |
| JP | 2007-510518 | 4/2007 |
| JP | 2007-514405 A | 6/2007 |
| JP | 2007-178328 | 7/2007 |
| WO | WO 88/06633 | 9/1988 |
| WO | WO 90/12350 | 10/1990 |
| WO | WO 92/05443 | 4/1992 |
| WO | WO 94/11103 | 5/1994 |
| WO | WO 97/05492 | 2/1997 |
| WO | WO 98/00231 | 1/1998 |
| WO | WO 98/22625 | 5/1998 |
| WO | WO 98/35013 A1 | 8/1998 |
| WO | WO 98/53311 | 11/1998 |
| WO | WO 99/01688 | 1/1999 |
| WO | WO 99/09042 | 2/1999 |
| WO | WO 99/12016 | 3/1999 |
| WO | WO 99/33559 | 7/1999 |
| WO | WO 01/05510 | 1/2001 |
| WO | WO 01/14931 | 3/2001 |
| WO | WO 01/27614 | 4/2001 |
| WO | WO 01/28684 | 4/2001 |
| WO | WO 01/41931 | 6/2001 |
| WO | WO 01/54813 | 8/2001 |

(56) References Cited

FOREIGN PATENT DOCUMENTS

| WO | WO 01/89681 | 11/2001 |
|---|---|---|
| WO | WO 02/072264 | 9/2002 |
| WO | WO 02/078845 | 10/2002 |
| WO | WO 03/007677 | 1/2003 |
| WO | WO 03/012325 | 2/2003 |
| WO | WO 03/012406 | 2/2003 |
| WO | WO 03/048295 | 6/2003 |
| WO | WO 03/055605 | 7/2003 |
| WO | WO 03/087410 | 10/2003 |
| WO | WO 2004/007081 | 1/2004 |
| WO | WO 2004/048545 | 6/2004 |
| WO | WO 2004/055522 | 7/2004 |
| WO | WO 2004/056485 A1 | 7/2004 |
| WO | WO 2004/074848 | 9/2004 |
| WO | WO 2004/094986 | 11/2004 |
| WO | WO 2005/008255 | 1/2005 |
| WO | WO 2005/011867 | 2/2005 |
| WO | WO 2005/030984 | 4/2005 |
| WO | WO 2005/107947 | 11/2005 |
| WO | WO 2005/108571 | 11/2005 |
| WO | WO 2005/108620 | 11/2005 |
| WO | WO 2005/116202 | 12/2005 |
| WO | WO 2005/118867 | 12/2005 |
| WO | WO 2005/120710 | 12/2005 |
| WO | WO 2006/010584 | 2/2006 |
| WO | WO 2006/032044 | 3/2006 |
| WO | WO 2006/035800 | 4/2006 |
| WO | WO 2006/043642 | 4/2006 |
| WO | WO 2006/066001 | 6/2006 |
| WO | WO 2006/079082 | 7/2006 |
| WO | WO 2006/081995 | 8/2006 |
| WO | WO 2006/113198 | 10/2006 |
| WO | WO 2006/119280 | 11/2006 |
| WO | WO 2007/044917 | 4/2007 |
| WO | WO 2007/050327 | 5/2007 |
| WO | WO 2007/064117 | 6/2007 |
| WO | WO 2007/091530 | 8/2007 |
| WO | WO 2007/112114 | 10/2007 |
| WO | WO 2008/030914 | 3/2008 |
| WO | WO 2008/060604 | 5/2008 |
| WO | WO 2009/012185 | 1/2009 |
| WO | WO 2009/054870 A2 | 4/2009 |
| WO | WO 2010/118541 | 10/2010 |
| WO | WO 2010/140680 | 12/2010 |
| WO | WO 2011/101467 | 8/2011 |

OTHER PUBLICATIONS

Kuo et al., "Remnant cationic dendrimers block RNA migration in electrophoresis after monophasic lysis", J Biotech. (2007) 129: 383-390.
Tanaka et al., "Modification of DNA extraction from maize using polyamidoamine-dendrimer modified magnetic particles", Proceedings of the 74th Annual Meeting of the Electrochemical Society of Japan, Mar. 29, 2007; Faculty of Engineering, Science University of Tokyo; 2 pages.
Wu et al., "Polycationic dendrimers interact with RNA molecules: polyamine dendrimers inhibit the catalytic activity of Candida ribozymes", Chem Commun. (2005) 3: 313-315.
Zhou et al., "Cooperative binding and self-assembling behavior of cationic low molecular-weight dendrons with RNA molecules", Org Biomol Chem. (2006) 4(3): 581-585.
Zhou et al., "PANAM dendrimers for efficient siRNA delivery and potent gene silencing", Chem Comm.(Camb.) (2006) 22: 2362-2364.
Bollet, C. et al., "A simple method for the isolation of chromosomal DNA from Gram positive or acid-fast bacteria", Nucleic Acids Research, vol. 19, No. 8 (1991), p. 1955.
Brahmasandra et al., On-chip DNA detection in microfabricated separation systems, SPIE Conference on Microfluidic Devices and Systems, 1998, vol. 3515, pp. 242-251, Santa Clara, CA.
Breadmore, M.C. et al., "Microchip-Based Purification of DNA from Biological Samples", Anal. Chem., vol. 75 (2003), pp. 1880-1886.
Brody, et al., Diffusion-Based Extraction in a Microfabricated Device, Sensors and Actuators Elsevier, 1997, vol. A58, No. 1, pp. 13-18.
Burns et al., "An Integrated Nanoliter DNA Analysis Device", Science 282:484-487 (1998).
Carlen et al., "Paraffin Actuated Surface Micromachined Valve," in IEEE MEMS 2000 Conference, Miyazaki, Japan, (Jan. 2000) pp. 381-385.
Chung, Y. et al., "Microfluidic chip for high efficiency DNA extraction", Miniaturisation for Chemistry, Biology & Bioengineering, vol. 4, No. 2 (Apr. 2004), pp. 141-147.
Goldmeyer et al., "Identification of *Staphylococcus aureus* and Determination of Methicillin Resistance Directly from Positive Blood Cultures by Isothermal Amplification and a Disposable Detection Device", J Clin Microbiol. (Apr. 2008) 46(4): 1534-1536.
Handique et al, "Microfluidic flow control using selective hydrophobic patterning", SPIE, (1997) 3224: 185-194.
Handique et al., On-Chip Thermopneumatic Pressure for Discrete Drop Pumping, Analytical Chemistry, American Chemical Society, Apr. 15, 2001, vol. 73, No. 8, 1831-1838.
Handique, K. et al., "Nanoliter-volume discrete drop injection and pumping in microfabricated chemical analysis systems", Solid-State Sensor and Actuator Workshop (Hilton Head, South Carolina, Jun. 8-11, 1998) pp. 346-349.
Handique, K. et al., "Mathematical Modeling of Drop Mixing in a Slit-Type Microchannel", J. Micromech. Microeng., 11:548-554 (2001).
Handique, K. et al., "Nanoliter Liquid Metering in Microchannels Using Hydrophobic Patterns", Anal. Chem., 72:4100-4109 (2000).
He, et al., Microfabricated Filters for Microfluidic Analytical Systems, Analytical Chemistry, American Chemical Society, 1999, vol. 71, No. 7, pp. 1464-1468.
Ibrahim, et al., Real-Time Microchip PCR for Detecting Single-Base Differences in Viral and Human DNA, Analytical Chemistry, American Chemical Society, 1998, 70(9): 2013-2017.
Khandurina et al., Microfabricated Porous Membrane Structure for Sample Concentration and Electrophoretic Analysis, Analytical Chemistry American Chemical Society, 1999, 71(9): 1815-1819.
Kopp et al., Chemical Amplification: Continuous-Flow PCR on a Chip, www.sciencemag.org, 1998, vol. 280, pp. 1046-1048.
Kutter et al., Solid Phase Extraction on Microfluidic Devices, J. Microcolumn Separations, John Wiley & Sons, Inc., 2000, 12(2): 93-97.
Lagally et al., Single-Molecule DNA Amplification and Analysis in an Integrated Microfluidic Device, Analytical Chemistry, American Chemical Society, 2001, 73(3): 565-570.
Livache et al., "Polypyrrole DNA chip on a Silicon Device: Example of Hepatitis C Virus Genotyping", Analytical Biochemistry, (1998) 255: 188-194.
Mascini et al., "DNA electrochemical biosensors", Fresenius J. Anal. Chem., 369: 15-22, (2001).
Nakagawa et al., Fabrication of amino silane-coated microchip for DNA extraction from whole blood, J of Biotechnology, Mar. 2, 2005, vol. 116, pp. 105-111.
Northrup et al., A Miniature Analytical Instrument for Nucleic Acids Based on Micromachined Silicon Reaction Chambers, Analytical Chemistry, American Chemical Society, 1998, 70(5): 918-922.
Oleschuk et al., Trapping of Bead-Based Reagents within Microfluidic Systems,: On-Chip Solid-Phase Extraction and Electrochromatography, Analytical Chemistry, American Chemical Society, 2000, 72(3): 585-590.
Plambeck et al., "Electrochemical Studies of Antitumor Antibiotics", J. Electrochem Soc.: Electrochemical Science and Technology (1984), 131(11): 2556-2563.
Roche et al. "Ectodermal commitment of insulin-producing cells derived from mouse embryonic stem cells" Faseb J (2005) 19: 1341-1343.
Ross et al., Analysis of DNA Fragments from Conventional and Microfabricated PCR Devices Using Delayed Extraction MALDI-

(56) References Cited

OTHER PUBLICATIONS

TOF Mass Spectrometry, Analytical Chemistry, American Chemical Society, 1998, 70(10): 2067-2073.

Shoffner et al., Chip PCR.I. Surface Passivation of Microfabricated Silicon-Glass Chips for PCR, Nucleic Acids Research, Oxford University Press, (1996) 24(2): 375-379.

Smith, K. et al., "Comparison of Commercial DNA Extraction Kits for Extraction of Bacterial Genomic DNA from Whole-Blood Samples", Journal of Clinical Microbiology, vol. 41, No. 6 (Jun. 2003), pp. 2440-2443.

Wang, "Survey and Summary, from DNA Biosensors to Gene Chips", Nucleic Acids Research, 28(16):3011-3016, (2000).

Waters et al., Microchip Device for Cell Lysis, Multiplex PCR Amplification, and Electrophoretic Sizing, Analytical Chemistry, American Chemical Society, 1998, 70(1): 158-162.

Weigl et al., Microfluidic Diffusion-Based Separation and Detection, www.sciencemag.org, 1999, vol. 283, pp. 346-347.

Yoza et al., "Fully Automated DNA Extraction from Blood Using Magnetic Particles Modified with a Hyperbranched Polyamidomine Dendrimer", Journal of Bioscience and Bioengineering, 2003, 95(1): 21-26.

Yoza et al., DNA extraction using bacterial magnetic particles modified with hyperbranched polyamidoamine dendrimer, Mar. 20, 2003, 101(3): 219-228.

International Search Report and Written Opinion dated Jul. 12, 2013 for Application No. PCT/US2012/033667, filed Apr. 13, 2012.

Allemand et al., "pH-Dependent Specific Binding and Combing of DNA", Biophys J. (1997) 73(4): 2064-2070.

Harding et al., "DNA isolation using Methidium-Spermine-Sepharose", Meth Enzymol. (1992) 216: 29-39.

Harding et al., "Rapid isolation of DNA from complex biological samples using a novel capture reagent—methidium-spermine-sepharose", Nucl Acids Res. (1989) 17(17): 6947-6958.

Labchem; Sodium Hydroxide, 0,5N (0.5M); Safety Data Sheet, 2015; 8 pages.

Extended European Search Report dated Mar. 8, 2017 for European Patent Application No. 16199078.3.

\* cited by examiner

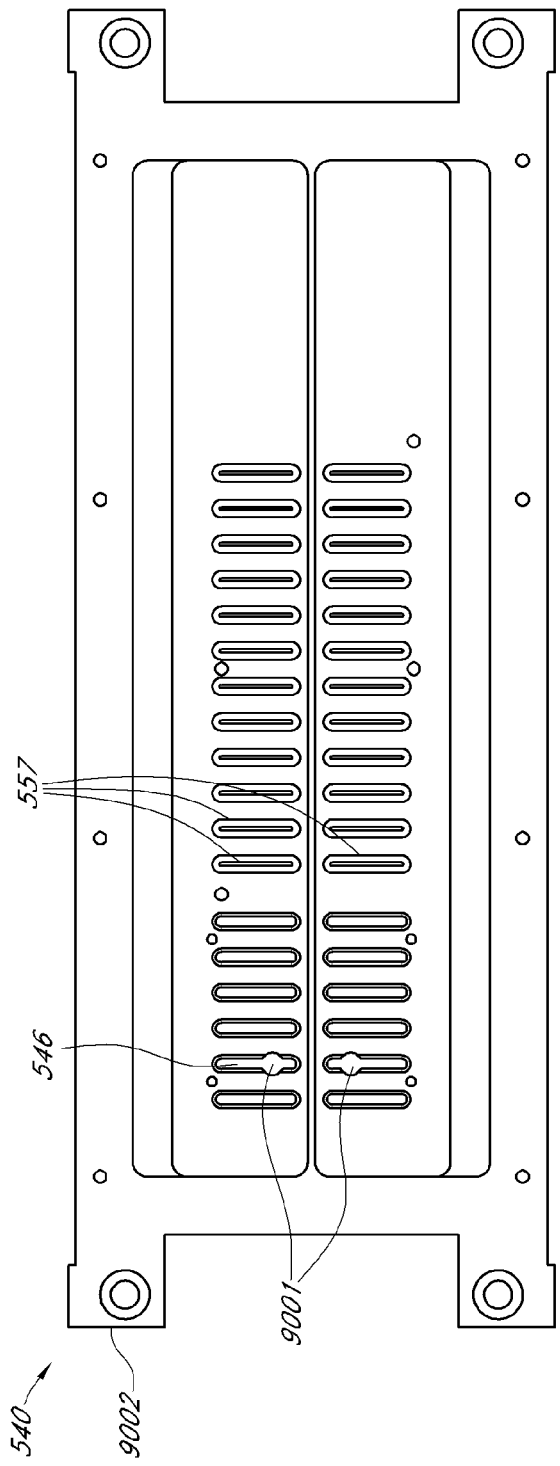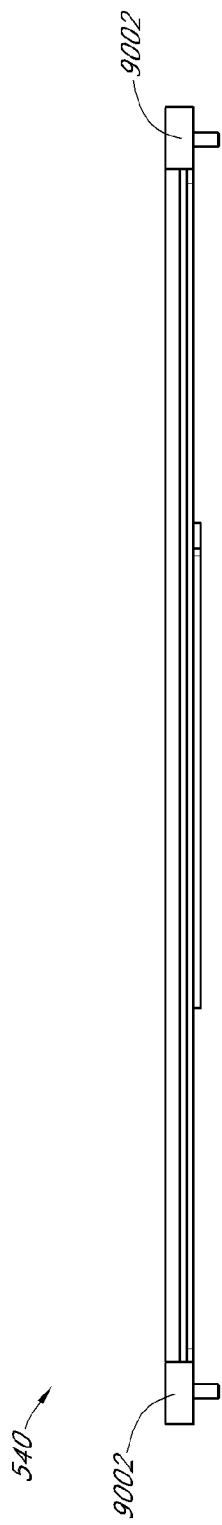
FIG. 9A
FIG. 9B

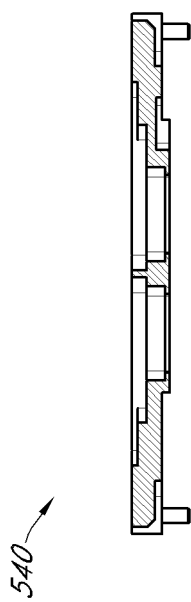
FIG. 9F
FIG. 9G
FIG. 9H

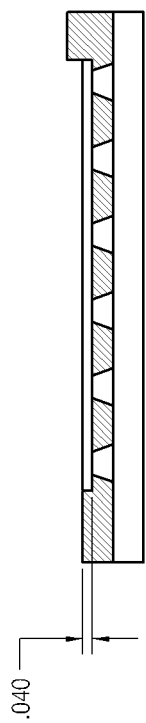
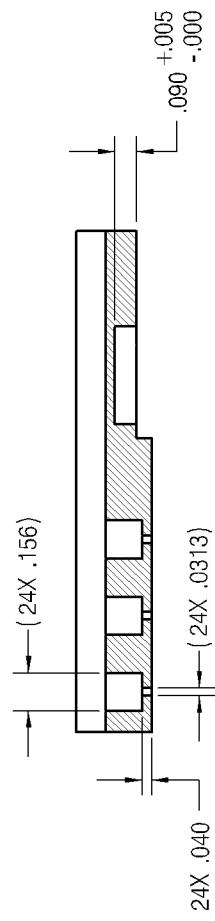
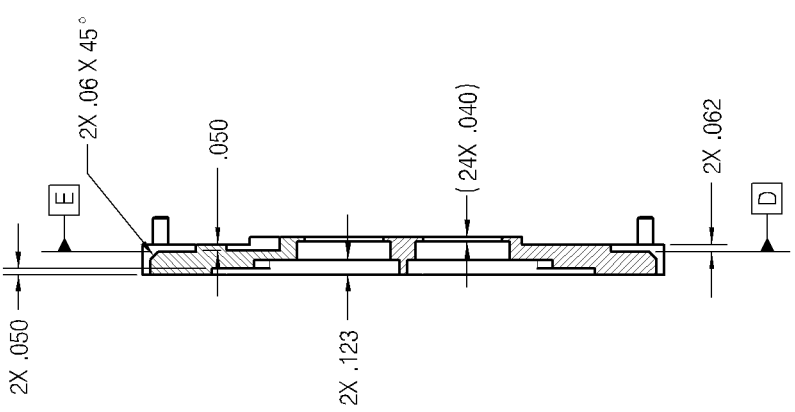
FIG. 10G
FIG. 10H
FIG. 10F

SCANNING REAL-TIME MICROFLUIDIC THERMOCYCLER AND METHODS FOR SYNCHRONIZED THERMOCYCLING AND SCANNING OPTICAL DETECTION

CROSS-REFERENCE TO RELATED APPLICATIONS

This application is a continuation of and claims the benefit of priority to co-pending International Patent Application No. PCT/US2012/033667, filed Apr. 13, 2012, entitled "SYNCHRONIZED THERMOCYCLING AND SCANNING OPTICAL DETECTION," which claims the benefit of priority to U.S. Provisional Patent Application Ser. No. 61/476,175, filed on Apr. 15, 2011, entitled "SOFTWARE CONTROL PROCESS TO SYNCHRONIZE THERMOCYCLING AND SCANNING OPTICAL DETECTION" and U.S. Provisional Patent Application Ser. No. 61/476,167, filed on Apr. 15, 2011, entitled "6-COLOR SCANNING REAL-TIME MICROFLUIDIC THERMOCYCLER." Each of the aforementioned applications is incorporated by reference herein in its entirety.

TECHNICAL FIELD

The systems and methods disclosed herein relate generally to the automated execution of nucleic acid amplification assays, such as Polymerase Chain Reaction (PCR), and in some instances real-time PCR, in a plurality of micro-fluidic reaction chambers in a microfluidic cartridge. The system may subsequently detect target nucleic acids, e.g., target amplicons, within each of the reaction chambers.

BACKGROUND OF THE INVENTION

The medical diagnostics industry is a critical element of today's healthcare infrastructure. At present, however, in vitro diagnostic analyses, no matter how routine, have become a bottleneck in patient care. There are several reasons for this. First, many diagnostic analyses can only be done with highly specialized equipment that is both expensive and only operable by trained clinicians. Such equipment may be found in only a few locations—often just one in any given urban area. This requires hospitals to send out samples for analyses to these locations, thereby incurring shipping costs and transportation delays, and possibly even sample loss or mishandling. Second, the equipment in question is typically not available "on-demand" but instead runs in batches, thereby delaying the processing time for many samples as they must wait for a machine to reach capacity before they can be run.

Understanding that diagnostic assays on biological samples may break down into several key steps, it is often desirable to automate one or more steps. For example, a biological sample, such as those obtained from a patient, can be used in nucleic acid amplification assays, in order to amplify a target nucleic acid (e.g., DNA, RNA, or the like) of interest. Once amplified, the presence of a target nucleic acid, or amplification product of a target nucleic acid (e.g., a target amplicon) reactor can be detected, wherein the presence of a target nucleic acid and/or target amplicon is used to identify and/or quantify the presence of a target (e.g., a target microorganism or the like). Often, nucleic acid amplification assays involve multiple steps, which can include nucleic acid extraction, nucleic acid amplification, and detection. It is desirable to automate certain steps of these processes.

There is a need for a method and apparatus for carrying out molecular diagnostic assays on multiple samples in parallel, with or without amplification of target nucleic acids, and detection on a prepared biological samples. The system may be configured for high throughput, and operation in a commercial reference laboratory or at the point of care, thereby eliminating the need to send the sample out to a specialized facility.

SUMMARY OF THE INVENTION

The embodiments disclosed herein relate to methods and devices for the simultaneous testing of multiple samples. Certain embodiments contemplate an apparatus for performing real-time nucleic acid amplification and detection. The apparatus can include a detector head comprising a plurality of photodetector and light source pairs. The detector head can be mounted on a rail, wherein the detector and light source pairs are aligned in a first row and a second row. The apparatus can include a receptacle for a microfluidic cartridge that has a plurality of independent reaction chambers aligned in adjacent columns of a first row and a second row. The apparatus can also include an aperture plate that is configured to be positioned over the microfluidic cartridge when the cartridge is present in the receptacle. The aperture plate can include a plurality of apertures that are each aligned over each of the plurality of reaction chambers when the receptacle is holding the microfluidic cartridge. The detector head can be located over the aperture plate, and be moveable along the rail, such that each of the plurality of photodetector and light source pairs in the first row can be positioned over each aperture in the first row of the aperture plate, and each of the plurality of photodetector and light source pairs in the second row can be positioned over each aperture in the second row of the aperture plate.

In some embodiments, the apparatus also includes a second detector head that has a plurality of photodetector and light source pairs aligned into a first row and a second row. The second detector head can be mounted on the rail. The apparatus can also include a second receptacle for a microfluidic cartridge including a plurality of independent reaction chambers aligned in adjacent columns of a first row and a second row. The apparatus can also include a second aperture plate configured to be positioned over the second microfluidic cartridge when the second cartridge is present in the second receptacle, and which can include a plurality of apertures that are each aligned over each of the plurality of reaction chambers of the second microfluidic cartridge when the second receptacle is holding the second microfluidic cartridge. The second detector head can be located over the aperture plate, and can be moveable along the rail such that each of the plurality of photodetector and light source pairs in the first row of the second detector head can be positioned over each aperture in the first row of the second aperture plate, and each of the plurality of photodetector and light source pairs in the second row of the second detector head can be positioned over each aperture in the second row of the second aperture plate.

In some embodiments, the photodetector and light source pairs can include at least six different photodetector and light source pairs operating in six different wavelengths. In some embodiments, the six different wavelengths comprise a light source emitting a green colored light, a light source emitting a yellow colored light, a light source emitting an orange colored light, a light source emitting a red colored light, and a light source emitting a crimson colored light. In some embodiments, the detector head includes at least N rows of photodetector and light source pairs, and the detector is configured to move to at least M+N−1 positions over an aperture plate comprising M rows of apertures.

In some embodiments, the aperture plate comprises steel, aluminum, nickel, or a combination thereof. In some embodiments, the aperture plate can have a thickness of approximately 0.25 inches. In some embodiments, at least part of the aperture plate is electrochemically oxidized to be darker than when the aperture plate is not electrochemically oxidized. In some embodiments, the aperture plate provides substantially uniform pressure across the area of the microfluidic cartridge, when the cartridge is present within the receptacle. In some embodiments, the aperture plate comprises at least one of aluminum, zinc or nickel, the aperture plate further comprising a colorant.

In some embodiments, the apparatus further comprises a heater plate, wherein the heater plate is positioned underneath the microfluidic cartridge when a cartridge is present in the receptacle. In some embodiments the heater plate comprises at least one of glass or quartz. In some embodiments, the aperture plate provides substantially uniform pressure across the area of the microfluidic cartridge when a cartridge is present within the receptacle. The substantially uniform pressure can facilitate substantially uniform thermal contact between the microfluidic reaction chambers and the heater plate. As such, in some embodiments, the aperture plate provide uniform pressure that can ensure that each of the plurality of reaction chambers or reactors in the microfluidic cartridge are in uniformly thermal contact or communication with a respective a plurality of heating elements located within the heater plate.

In some embodiments, the apparatus further comprises a photodetector, the photodetector located over the aperture plate, wherein the micro-fluidic chamber is configured to receive light at a glancing angle from a light source relative to the photodetector. In some embodiments, the heater plate comprises a plurality of heating elements, wherein each of the plurality of heating elements is positioned such that when the microfluidic cartridge is present in the receptacle, the plurality of heating elements are in thermal connection with each of the plurality of reaction chambers, respectively.

Certain embodiments contemplate a method implemented on one or more computer processors for optimizing protocols, such as polymerase chain reaction (PCR) protocols or the like, for simultaneously performing a plurality of thermal cycling reactions, wherein each thermal cycling reaction comprises one or more detection steps, and wherein the thermal cycling reactions are performed in a plurality of reactors. The method can include the steps of determining or providing or accessing a detection cycle time for each of the plurality of reactors; receiving or accessing a protocol step, the step associated with a step duration, the step comprising a time for detection; and determining a first adjustment to the step such that the step duration is a multiple of the detection cycle time.

In some embodiments the method further comprises determining a second adjustment to the step, wherein the time for detection is a multiple of the detection cycle time when the step is adjusted by the first adjustment and by the second adjustment. In some embodiments the method further comprises determining a starting offset adjustment based on a position of a reaction chamber associated with the protocol. In some embodiments, the detection cycle time comprises the amount of time required for a detector head to perform a predetermined plurality of detections for a reactor. In some embodiments, the detection cycle time includes a time required for movement of the detector head to each of a plurality of reactors and movement of the detector head to the start position. In some embodiments, the method further comprises initiating the protocol.

Certain embodiments contemplate a non-transitory computer-readable medium comprising instructions, the instructions configured to cause one or more processors to perform the following steps: determining or providing or accessing a detection cycle time; receiving or accessing a protocol step, wherein the step is associated with a step duration, and the wherein step includes a time for detection; and determining a first adjustment to the step such that the step duration is a multiple of the detection cycle time.

In some embodiments, the protocol step is associated with a protocol from a plurality of protocols. Each of the plurality of protocols can be associated with at least one of a plurality of thermal cycling reactions, such as polymerase chain reaction (PCR) protocols, wherein each thermal cycling reaction comprises one or more detection steps, and wherein the determining a first adjustment is based at least in part on a timing of one or more detection steps associated with the thermal cycling reactions of at least two or more of the plurality of protocols when the two or more of the plurality of protocols are simultaneously run. In some embodiments, the method also includes the step of determining a second adjustment to the step, wherein the time for detection is a multiple of the detection cycle time when the step is adjusted by the first adjustment and by the second adjustment. In some embodiments, the method also includes the step of determining a starting offset adjustment based on a position of a reaction chamber associated with the protocol. In some embodiments, the detection cycle time includes the amount of time required for a detector head to perform a predetermined plurality of detections for a reaction chamber. In some embodiments, the detection cycle time also includes a time required for movement of the detector head to each of a plurality of reaction chamber detection positions and movement of the detector head to a start position. In some embodiments, the method further comprises initiating the protocol.

Certain embodiments contemplate a system for optimizing protocols for a plurality of reaction chambers. The system can include a processor configured to perform the following: determining or providing or accessing a detection cycle time; receiving or accessing a protocol step, wherein the step can be associated with a step duration, and wherein the step includes a time for detection; and determining a first adjustment to the step such that the step duration is a multiple of the detection cycle time.

In some embodiments, the protocol step is associated with a protocol from a plurality of protocols. Each of the plurality of protocols can be associated with at least one of a plurality of thermal cycling reactions, such as a polymerase chain reaction (PCR) protocol, wherein each thermal cycling reaction comprises one or more detection steps, and wherein the determining a first adjustment is based at least in part on a timing of one or more detection steps associated with the thermal cycling reactions of at least two or more of the plurality of protocols when the two or more of the plurality of protocols are simultaneously run. In some embodiments, the processor is also configured to determine a second adjustment to the step, wherein the time for detection is a multiple of the detection cycle time when the step is adjusted by the first adjustment and by the second adjustment. In some embodiments, the processor is also configured to determine a starting offset adjustment based on a position of a reaction chamber associated with the protocol. In some embodiments, the detection cycle time includes the amount of time required for a detector head to perform a predetermined plurality of detections for a reaction chamber. In some embodiments, the detection cycle time also includes a time required for movement of the detector head to each of a plurality of reaction chamber detection positions and movement of the detector head to the start position. In some embodiments, the processor is further configured to initiate the protocol.

Certain embodiments contemplate a method for simultaneously performing real-time PCR in a plurality of PCR reaction chambers, comprising: (a) providing a scan time sufficient for a detector assembly to perform a scan cycle during which it can scan each of the plurality of PCR reaction chambers for at least one detectable signal and become ready to repeat the scan; (b) providing a reaction protocol for each of the PCR reaction chambers that includes multiple cycles, each cycle comprising a cycle time that includes at least one heating step, at least one cooling step, and at least one temperature plateau that includes a reading cycle period during which the detector assembly is to scan the reaction chamber for at least one detectable signal; (c) determining, using a processor, whether the cycle time for that reaction chamber is the same as or an integer multiple of the scan time, and if not, adjusting the scan time or the cycle time so that the cycle time is the same as or an integer multiple of the scan time; (d) performing at least steps (b) and (c) for the reaction protocol for each of the plurality of PCR reaction chambers so that the cycle time for each reaction protocol is the same as or an integer multiple of the scan time; and (e) under direction of a processor, performing real time PCR on each of the reaction chambers using the reaction protocol for each of the reaction chambers, including performing multiple scan cycles with the detector assembly, wherein each PCR reaction chamber is scanned by the detector assembly during each reading cycle period for that reaction chamber.

In some embodiments the method further comprises phase adjusting the cycle time of the reaction protocol for at least one of the reaction chambers. In some embodiments, at least one said reaction protocol is different from another said reaction protocol. In some embodiments, at least one cycle time in one reaction protocol is different from the cycle time in another reaction protocol.

BRIEF DESCRIPTION OF THE DRAWINGS

FIGS. 9A-H illustrate various perspectives of one embodiment of the aperture plate.

FIGS. 10A-H illustrate various dimensions of the perspectives of the aperture plate of FIGS. 9A-H.

FIGS. 15A and 15B illustrate the character of the protocol profiles prior to the starting offset adjustment. FIG. 15C illustrates the plurality of protocol profiles relative to one another after applying the starting offset adjustments.

DETAILED DESCRIPTION

Figure 1A:
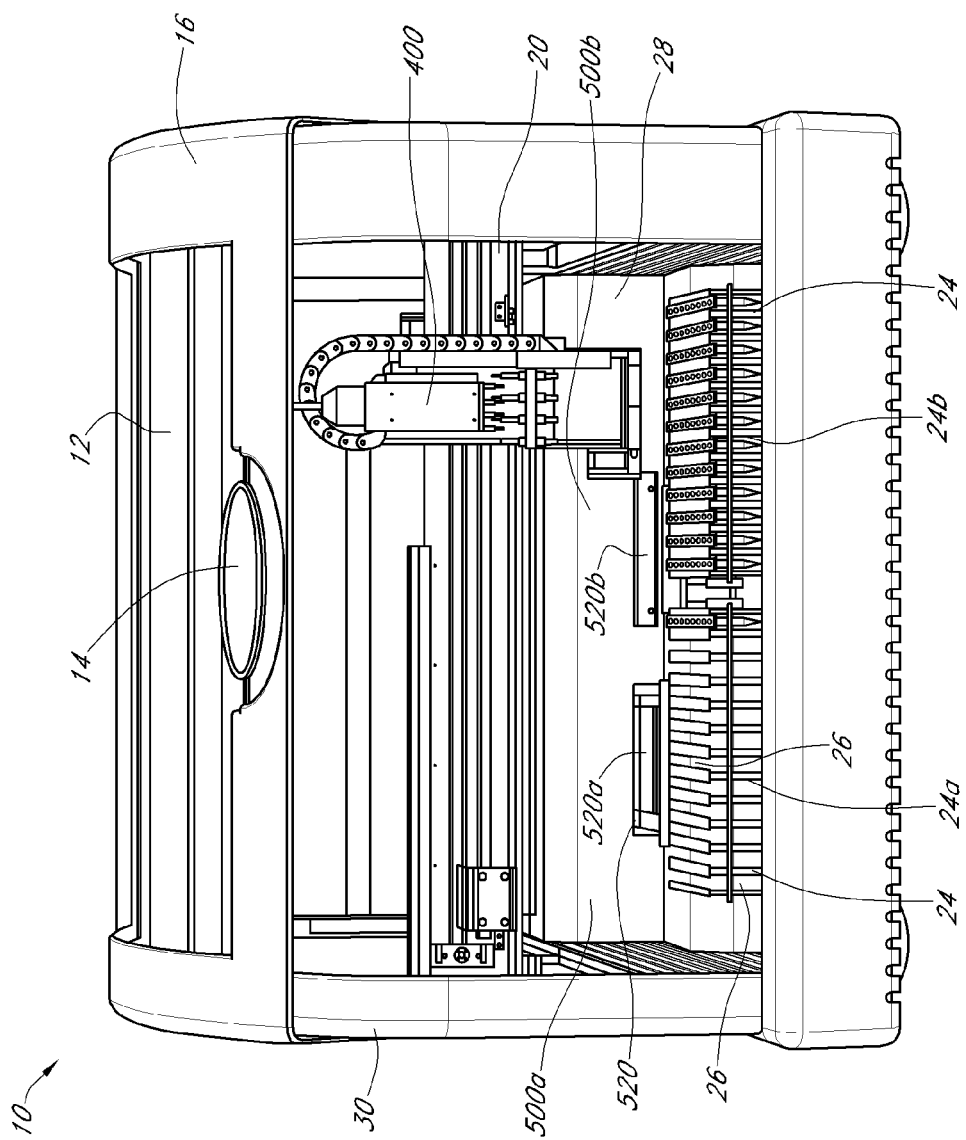
FIG. 1A is a front plan view of a diagnostic apparatus as used in certain of the embodiments.

Certain of the present embodiments contemplate an apparatus, referred to herein as a thermocycler, which may consistently heat and analyze microfluidic chambers. Polynucleotide amplification, such as by real-time PCR, can be performed within the microfluidic chambers. In some embodiments, the thermocycler can be configured to perform individual thermocycling and detection protocols in a plurality of microfluidic reaction chambers within a microfluidic cartridge. The thermocycling can be used to amplify nucleic acids, e.g., DNA, RNA or the like, e.g., by real-time PCR or other nucleic acid amplification protocols described herein, within the microfluidic reaction chambers. The thermocycler may comprise a detector head, comprising a plurality of detector pairs, e.g., six or more detector head pairs, wherein each detector pair comprises a light-emitting source, e.g., an LED or the like, and a cognate photodiode. In some embodiments, each individual detector pair is configured to generate and detect light emitted from a fluorescent moiety, e.g., a fluorescent probe, to indicate the presence of a target polynucleotide.

As used herein, the term "microfluidic" refers to volumes of less than 1 ml, preferably less than 0.9 ml, e.g., 0.8 ml, 0.7 ml, 0.6 ml, 0.5 ml, 0.4 ml, 0.3 ml, 0.2 ml, 0.1 ml, 90 µl, 80 µl, 70 µl, 60 µl, 50 µl, 40 µl, 30 µl, 20 µl, 10 µl, 5 µl, µl, 3 µl, 2 µl, 1 µl, or less, or any amount in between. It is to be understood that, unless specifically made clear to the contrary, where the term PCR is used herein, any variant of PCR including but not limited to real-time and quantitative PCR, and any other form of polynucleotide amplification is intended to be encompassed.

The detection process used in the assay may also be multiplexed to permit multiple concurrent measurements on multiple reactions concurrently. In some embodiments, these measurements may be taken from separate reaction chambers. Certain of these embodiments perform a plurality of PCR reactions simultaneously in a single PCR reaction chamber, e.g., multiplex PCR. A PCR protocol may comprise guidelines for performing the successive annealing and denaturing of the polynucleotides in the reaction chamber prior to detection. Such guidelines, comprising a time profile for heating the chamber, may be referred to as a "protocol". Certain of the disclosed embodiments facilitate consistent heating and/or cooling across a plurality of reaction chambers performing PCR, while facilitating detection using a sensor array. In certain embodiments, the apparatus may comprise an aperture plate which facilitates consistent heating and cooling of the reaction chambers by applying pressure to a cartridge containing a plurality of PCR reaction chambers. Certain details and methods for processing polynucleotides may be found in e.g., U.S. Patent Application Publication 2009-0131650 and U.S. Patent Application Publication 2010-0009351, incorporated herein by reference.

The skilled artisan will appreciate that the embodiments disclosed herein are useful for various types of nucleic acid amplification reactions. For example, methods of nucleic acid amplification in connection with the embodiments disclosed herein can include, but are not limited to: polymerase chain reaction (PCR), strand displacement amplification (SDA), for example multiple displacement amplification (MDA), loop-mediated isothermal amplification (LAMP), ligase chain reaction (LCR), immuno-amplification, and a variety of transcription-based amplification procedures, including transcription-mediated amplification (TMA), nucleic acid sequence based amplification (NASBA), self-sustained sequence replication (3SR), and rolling circle amplification. See, e.g., Mullis, "Process for Amplifying, Detecting, and/or Cloning Nucleic Acid Sequences," U.S. Pat. No. 4,683,195; Walker, "Strand Displacement Amplification," U.S. Pat. No. 5,455,166; Dean et al, "Multiple displacement amplification," U.S. Pat. No. 6,977,148; Notomi et al., "Process for Synthesizing Nucleic Acid," U.S. Pat. No. 6,410,278; Landegren et al. U.S. Pat. No. 4,988,617 "Method of detecting a nucleotide change in nucleic acids"; Birkenmeyer, "Amplification of Target Nucleic Acids Using Gap Filling Ligase Chain Reaction," U.S. Pat. No. 5,427,930; Cashman, "Blocked-Polymerase Polynucleotide Immunoassay Method and Kit," U.S. Pat. No. 5,849,478; Kacian et al., "Nucleic Acid Sequence Amplification Methods," U.S. Pat. No. 5,399,491; Malek et al., "Enhanced Nucleic Acid Amplification Process," U.S. Pat. No. 5,130,238; Lizardi et al., BioTechnology, 6:1197 (1988); Lizardi et al., U.S. Pat. No. 5,854,033 "Rolling circle replication reporter systems."

In some embodiments disclosed herein, the target nucleic acid, e.g., target amplicon, can be detected using an oligonucleotide probe. Preferably, the probes include one or more detectable moieties that can be detected by the systems disclosed herein. The skilled artisan will appreciate that several probe technologies are useful in the embodiments described herein. By way of example, the embodiments disclosed herein can be used with TAQMAN® probes, molecular beacon probes, SCORPION™ probes, and the like.

TaqMan® assays are homogenous assays for detecting polynucleotides (see U.S. Pat. No. 5,723,591). In TAQMAN® assays, two PCR primers flank a central TAQMAN® probe oligonucleotide. The probe oligonucleotide contains a fluorophore and quencher. During the polymerization step of the PCR process, the 5' nuclease activity of the polymerase cleaves the probe oligonucleotide, causing the fluorophore moiety to become physically separated from the quencher, which increases fluorescence emission. As more PCR product is created, the intensity of emission at the novel wavelength increases.

Molecular beacons are an alternative to TAQMAN® probes for the detection of polynucleotides, and are described in, e.g., U.S. Pat. Nos. 6,277,607; 6,150,097; and 6,037,130. Molecular beacons are oligonucleotide hairpins which undergo a conformational change upon binding to a perfectly matched template. The conformational change of the oligonucleotide increases the physical distance between a fluorophore moiety and a quencher moiety present on the oligonucleotide. This increase in physical distance causes the effect of the quencher to be diminished, thus increasing the signal derived from the fluorophore.

The adjacent probes method amplifies the target sequence by polymerase chain reaction in the presence of two nucleic acid probes that hybridize to adjacent regions of the target sequence, one of the probes being labeled with an acceptor fluorophore and the other probe labeled with a donor fluorophore of a fluorescence energy transfer pair. Upon hybridization of the two probes with the target sequence, the donor fluorophore interacts with the acceptor fluorophore to generate a detectable signal. The sample is then excited with light at a wavelength absorbed by the donor fluorophore and the fluorescent emission from the fluorescence energy transfer pair is detected for the determination of that target amount. U.S. Pat. No. 6,174,670 discloses such methods.

Sunrise primers utilize a hairpin structure similar to molecular beacons, but attached to a target binding sequence which serves as a primer. When the primer's complementary strand is synthesized, the hairpin structure is disrupted, thereby eliminating quenching. These primers detect amplified product and do not require the use of a polymerase with a 5' exonuclease activity. Sunrise primers are described by Nazarenko et al. (Nucleic Acids Res. 25:2516-21 (1997) and in U.S. Pat. No. 5,866,336.

SCORPION™ probes combine a primer with an added hairpin structure, similar to Sunrise primers. However, the hairpin structure of SCORPION™ probes is not opened by synthesis of the complementary strand, but by hybridization of part of the hairpin structure with a portion of the target which is downstream from the portion which hybridizes to the primer.

DzyNA-PCR involves a primer containing the antisense sequence of a DNAzyme, an oligonucleotide capable of cleaving specific RNA phosphodiester bonds. The primer binds to a target sequence and drives an amplification reaction producing an amplicon which contains the active DNAzyme. The active DNAzyme then cleaves a generic reporter substrate in the reaction mixture. The reporter substrate contains a fluorophore-quencher pair, and cleavage of the substrate produces a fluorescence signal which increases with the amplification of the target sequence. DNAzy-PCR is described in Todd et al., Clin. Chem. 46:625-30 (2000), and in U.S. Pat. No. 6,140,055.

Fiandaca et al. describes a fluorogenic method for PCR analysis utilizing a quencher-labeled peptide nucleic acid (Q-PNA) probe and a fluorophore-labeled oligonucleotide primer. Fiandaca et al. Genome Research. 11:609-613 (2001). The Q-PNA hybridizes to a tag sequence at the 5' end of the primer.

Li et al. describes a double stranded probe having a quencher and fluorophore on opposite oligonucleotide strands. Li et al. Nucleic Acids Research. 30(2): e5, 1-9 (2002). When not bound to the target, the strands hybridize to each other and the probe is quenched. However, when a target is present at least one strand hybridizes to the target resulting in a fluorescent signal.

Fluorophore labels and moieties useful in the embodiments disclosed herein include, but are not limited to, dyes of the fluorescein family, the carboxyrhodamine family, the cyanine family, and the rhodamine family. Other families of dyes that can be used in the invention include, e.g., polyhalofluorescein-family dyes, hexachlorofluorescein-family dyes, coumarin-family dyes, oxazine-family dyes, thiazine-family dyes, squaraine-family dyes, chelated lanthanide-family dyes, the family of dyes available under the trade designation Alexa Fluor J, from Molecular Probes, and the family of dyes available under the trade designation Bodipy J, from Invitrogen (Carlsbad, Calif.). Dyes of the fluorescein family include, e.g., 6-carboxyfluorescein (FAM), 2',4',1,4,-tetrachlorofluorescein (TET), 2',4',5',7',1,4-hexachlorofluorescein (HEX), 2',7'-dimethoxy-4',5'-dichloro-6-carboxyrhodamine (JOE), 2'-chloro-5'-fluoro-7',8'-fused phenyl-1,4-dichloro-6-carboxyfluorescein (NED), 2'-chloro-7'-phenyl-1,4-dichloro-6-carboxyfluorescein (VIC), 6-carboxy-X-rhodamine (ROX), and 2',4',5',7'-tetrachloro-5-carboxyfluorescein (ZOE). Dyes of the carboxyrhodamine family include tetramethyl-6-carboxyrhodamine (TAMRA), tetrapropano-6-carboxyrhodamine (ROX), Texas Red, R110, and R6G. Dyes of the cyanine family include Cy2, Cy3, Cy3.5, Cy5, Cy5.5, and Cy7. Fluorophores are readily available commercially from, for instance, Perkin-Elmer (Foster City, Calif.), Molecular Probes, Inc. (Eugene, Oreg.), and Amersham GE Healthcare (Piscataway, N.J.).

As discussed above, in some embodiments, the probes useful in the embodiments disclosed herein can comprise a quencher. Quenchers may be fluorescent quenchers or non-fluorescent quenchers. Fluorescent quenchers include, but are not limited to, TAMRA, ROX, DABCYL, DABSYL, cyanine dyes including nitrothiazole blue (NTB), anthraquinone, malachite green, nitrothiazole, and nitroimidazole compounds. Exemplary non-fluorescent quenchers that dissipate energy absorbed from a fluorophore include those available under the trade designation Black Hole™ from Biosearch Technologies, Inc. (Novato, Calif.), those available under the trade designation Eclipse™. Dark, from Epoch Biosciences (Bothell, Wash.), those available under the trade designation Qx1J, from Anaspec, Inc. (San Jose, Calif.), and those available under the trade designation Iowa Black™ from Integrated DNA Technologies (Coralville, Iowa).

In some embodiments discussed above, a fluorophore and a quencher are used together, and may be on the same or different oligonucleotides. When paired together, a fluorophore and fluorescent quencher can be referred to as a donor fluorophore and acceptor fluorophore, respectively. A number of convenient fluorophore/quencher pairs are known in the art (see, for example, Glazer et al, Current Opinion in Biotechnology, 1997; 8:94-102; Tyagi et al., 1998, Nat. Biotechnol., 16:49-53) and are readily available commercially from, for instance, Molecular Probes (Junction City, Oreg.), and Applied Biosystems (Foster City, Calif.). Examples of donor fluorophores that can be used with various acceptor fluorophores include, but are not limited to, fluorescein, Lucifer Yellow, B-phycoerythrin, 9-acridineisothiocyanate, Lucifer Yellow VS, 4-acetamido-4'-isothio-cyanatostilbene-2,2'-disulfonic acid, 7-diethylamino-3-(4'-isothiocyanatophenyl)-4-methylcoumarin, succinimdyl 1-pyrenebutyrate, and 4-acetamido-4'-isothiocyanatostilbene-2-,2'-disulfonic acid derivatives. Acceptor fluorophores typically depend upon the donor fluorophore used. Examples of acceptor fluorophores include, but are not limited to, LC-Red 640, LC-Red 705, Cy5, Cy5.5, Lissamine rhodamine B sulfonyl chloride, tetramethyl rhodamine isothiocyanate, rhodaminexisothiocyanate, erythrosine isothiocyanate, fluorescein, diethylenetriamine pentaacetate or other chelates of Lanthanide ions (e.g., Europium, or Terbium). Donor and acceptor fluorophores are readily available commercially from, for instance, Molecular Probes or Sigma Chemical Co. (St. Louis, Mo.). Fluorophore/quencher pairs useful in the compositions and methods disclosed herein are well-known in the art, and can be found, e.g., described in S. Marras, "Selection of Fluorophore and Quencher Pairs for Fluorescent Nucleic Acid Hybridization Probes" available at the world wide web site molecular-beacons.org/download/marras.mmb06%28335%293.pdf (as of Apr. 11, 2012).

The detection process used in the assays disclosed herein advantageously permits multiple concurrent measurements of multiple detectable moieties, e.g., a plurality of probes containing different detectable moieties, etc. In some embodiments, these measurements may be taken from separate reaction chambers within a microfluidic cartridge, e.g., comprising a chamber layer (the chamber layer referring herein to that portion of the microfluidic cartridge containing the reaction chambers). Certain of these embodiments perform a plurality of amplification reactions simultaneously in a single reaction chamber, e.g., multiplex PCR. A PCR protocol may comprise guidelines for performing the successive annealing and denaturing of the polynucleotides in the reaction chamber prior to detection. In certain embodiments, the apparatus is configured to facilitate consistent heating and/or cooling across a plurality of reaction chambers to perform nucleic acid amplification, and to facilitate detection of target amplicons in individual reaction chambers, e.g., by detecting fluorescent emissions, using a sensor array.

In certain embodiments, the apparatus may comprise an aperture plate which facilitates consistent heating and cooling of the reaction chambers by applying pressure to a cartridge containing a plurality of reaction chambers via multiple, independent optical pairs. The aperture plate is preferably configured to enable and facilitate the generation and detection of fluorescent signals from probes within multiple, independent reaction chambers. In some embodiments, the aperture plate is configured such that there is an individual aperture (or windows), positioned over each of the individual reaction chambers in the microfluidic cartridge.

Diagnostic Apparatus

Figure 1B:
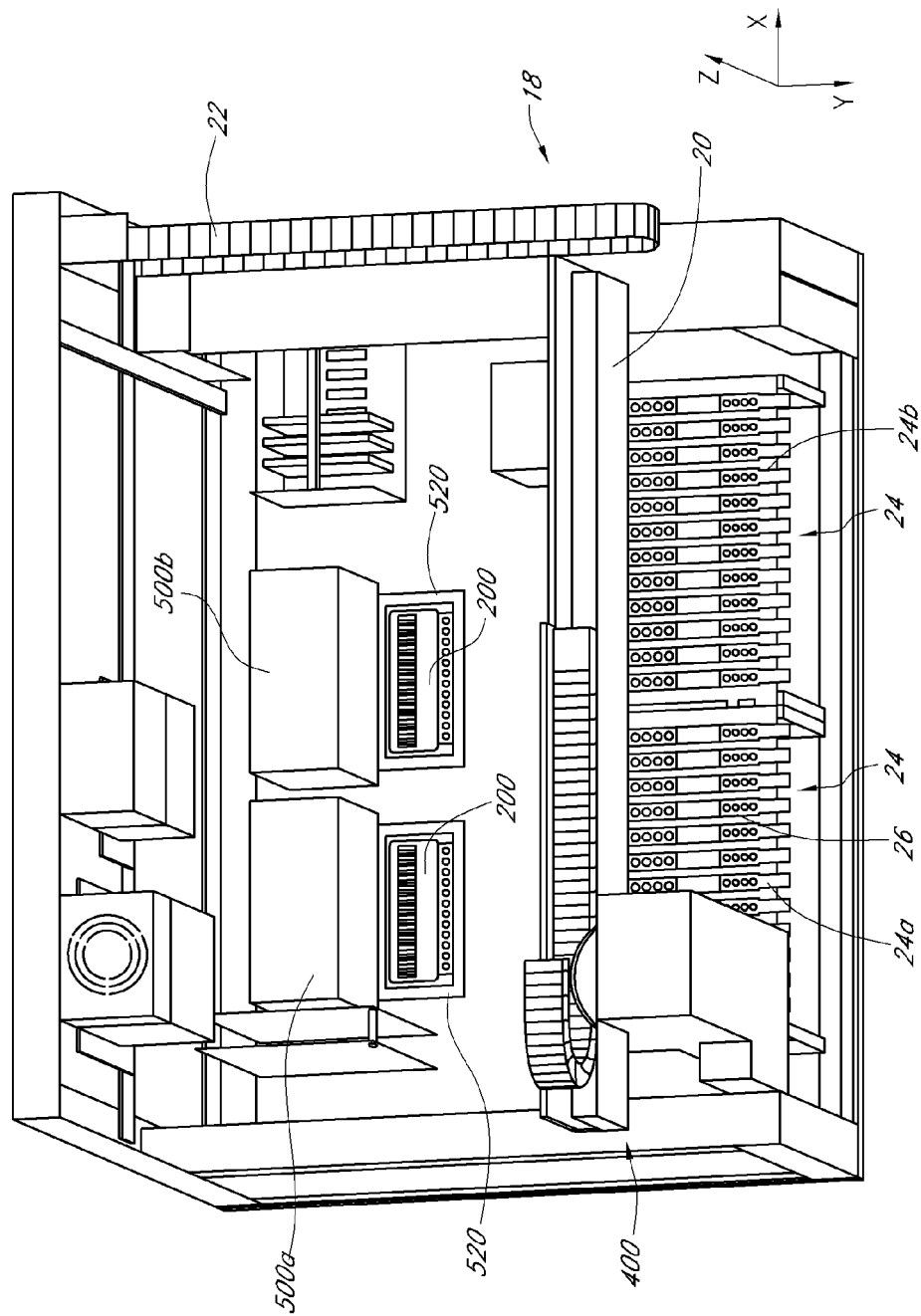
FIG. 1B is a top perspective view of the diagnostic apparatus of FIG. 1A showing certain of the apparatus' internal components.

FIGS. 1A and 1B show a diagnostic apparatus 10 of certain of the present embodiments. In the embodiment illustrated in FIG. 1A, the diagnostic apparatus includes an apparatus housing 30. The housing 30 may ensure a controlled environment for processing of the microfluidic samples and for preventing undesirable light from entering the detection space. The housing 30 may comprise a cover 16 which includes a handle 14 and a translucent window 12. The cover 16 may be brought down to close the opening in the front of the diagnostic apparatus 10 when the diagnostic apparatus 10 is in operation.

As seen in the embodiments of FIGS. 1A and 1B, the diagnostic apparatus 10 may house two specimen racks 24a, 24b in the front portion of the diagnostic apparatus 10. The skilled artisan will appreciate, however, that the depiction of the diagnostic apparatus in FIGS. 1A and 1B is exemplary only, and that in some embodiments, the apparatus can be configured to house more than two specimen racks, e.g., three, four, five, six, seven, eight, nine, ten, or more specimen racks. Preferably, the apparatus is configured to house the same number of specimen racks, .e.g., two, as microfluidic cartridges.

In some embodiments, each specimen rack 24a, 24b may include multiple holders 26. The holders 26 may include receptacles for holding diagnostic reagents, such as reagents for nucleic acid amplification, e.g., PCR reagents or the like. The racks 24 may also include specimen tubes (not shown) and mixing tubes (not shown) for preparing diagnostic-ready samples, such as amplification-ready samples. The apparatus may prepare the desired reagents in the racks 24a, 24b using the dispenser 400. Further description of various fluid dispensers may be found in e.g., U.S. Patent Application Publication 2009-0130719 and U.S. Patent Application Publication 2009-0155123, incorporated herein by reference.

In some embodiments, the reaction chambers within the microfluidic cartridge(s) includes one or more reagents, buffers, etc., used in the nucleic amplification assay. For example, in some embodiments, the reaction chambers of the microfluidic cartridge can include, e.g., amplification primers, probes, nucleotides, enzymes such as polymerase, buffering agents, or the like. By way of example, in some embodiments, the reaction chambers can include lyophilized reagents, to which processed biological sample (e.g., a solution of extracted nucleic acids) is added. The prepared fluids may then be transferred to a microfluidic cartridge and be inserted into heater/optical modules 500a, 500b for processing and analysis.

FIG. 1A is a front plan view of the diagnostic apparatus 10 of certain of the embodiments. As seen in FIG. 1A, the diagnostic apparatus 10 can include a fluid dispenser 400, mounted on a lateral rail 20. The lateral rail 20 may be part of a motor-driven gantry 18, which may also include a fore-aft rail 22 (not shown). The fore-aft rail 22 may be connected to the lateral rail 20 and mounted perpendicularly to the lateral rail 20 in the diagnostic apparatus 10.

FIG. 1A further illustrates the cover 28 over the heater/optical modules 500a, 500b. Receiving trays 520a and 520b may be located beneath or within the housing of the heater/optical modules 500a, 500b. Receiving tray 520a is illustrated in an open position, making it available to receive a microfluidic cartridge 200. Receiving tray 520b is illustrated in a closed position. Closing the tray not only places the reagents in the appropriate position for processing, but also further protects the interior of the heater/optical modules from receiving any unwanted stray light. Were stray light introduced into the detection area, the system may identify erroneous fluorescent levels derived from light which is not emitted from the reaction chamber.

FIG. 1B is a perspective view of the diagnostic apparatus 10 showing certain of the internal components found in certain of the embodiments. To better illustrate certain features, the apparatus housing 30, the cover 16, and the heater/optical cover 28 found in FIG. 1A have been removed from view in FIG. 1B. Shown in FIG. 1B is the gantry 18, including the lateral rail 20 fore-aft rail 22. The fluid dispenser 400 may be mounted on the lateral rail 20 and may slide laterally along the long lateral rail 20. The lateral rail 20 may be connected to the fore-aft rail 22 which may move in the fore-aft direction. In this manner the fluid dispenser 400 is available to move in the X, Y direction throughout the diagnostic device 10. As described below, the fluid dispenser 400 may also able to move up and down in the z-plane on the lateral rail 20, thereby giving the dispenser 400 the ability to move in three directional degrees throughout the diagnostic device 10.

Also shown in FIG. 1B are the heater/optical modules 500a, 500b with the cover 28 of the heater/optical modules of FIG. 1A removed. The receiving trays 520a and 520b are depicted in the open position and are each holding cartridges 200. In some embodiments, the receiving trays may each include a heater substrate 600 (not shown) beneath each of the microfluidic cartridges 200. The heater/optical modules 500a, 500b may also each include a detector head 700 described in greater detail below.

As will be described in more detail below, the diagnostic apparatus 10 may be capable of conducting real-time diagnostics on one or more samples. The sample to be tested may first be placed in a specimen tube (not shown) on the rack 24a or 24b. Diagnostic reagents may be located in the holders 26 on the rack 24a inside the diagnostic apparatus 10. The fluid dispenser 400 may mix and prepare the sample for diagnostic testing and may then deliver the prepared sample to the microfluidic cartridge 200 for thermal cycling and analyte detection in the heater/optical modules 500a, 500b. Alternatively, the fluid dispenser 400 may deliver nucleic acid samples to the reaction chambers of the microfluidic cartridge, wherein the reaction chambers of the microfluidic cartridge already contain reagents for an amplification reaction.

Figure 2:
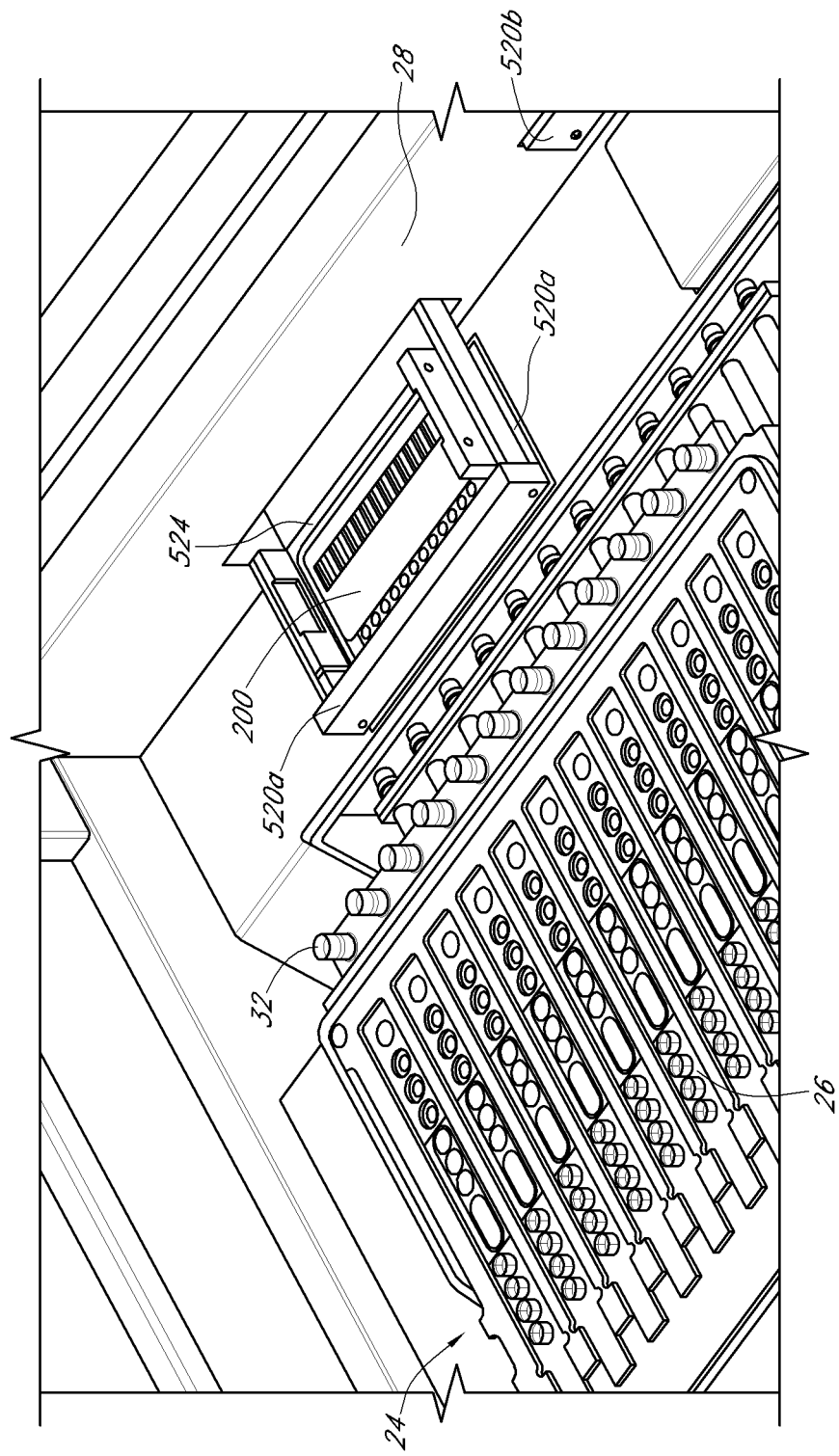
FIG. 2 illustrates an interior view of the diagnostic apparatus of FIGS. 1A and 1B.

FIG. 2 illustrates an interior view of the diagnostic apparatus 10, showing the rack 24a holding a number of sample tubes 32 and reagent holders 26, and a cartridge 200 situated in the receiving tray 520a. The receiving tray 520a is in an open position extending from the heater/optical module 500a which has the cover 28 attached. The receiving tray 520b is in a closed position. Advantageously, in some embodiments the receiving trays 520a, b may allow easy placement of the microfluidic cartridge 200, by a user or by an auto-loading device. Such a design may also accommodate multiplexed pipetting of samples using the robotic fluid dispenser 400.

Receiving Tray

Figure 3A:
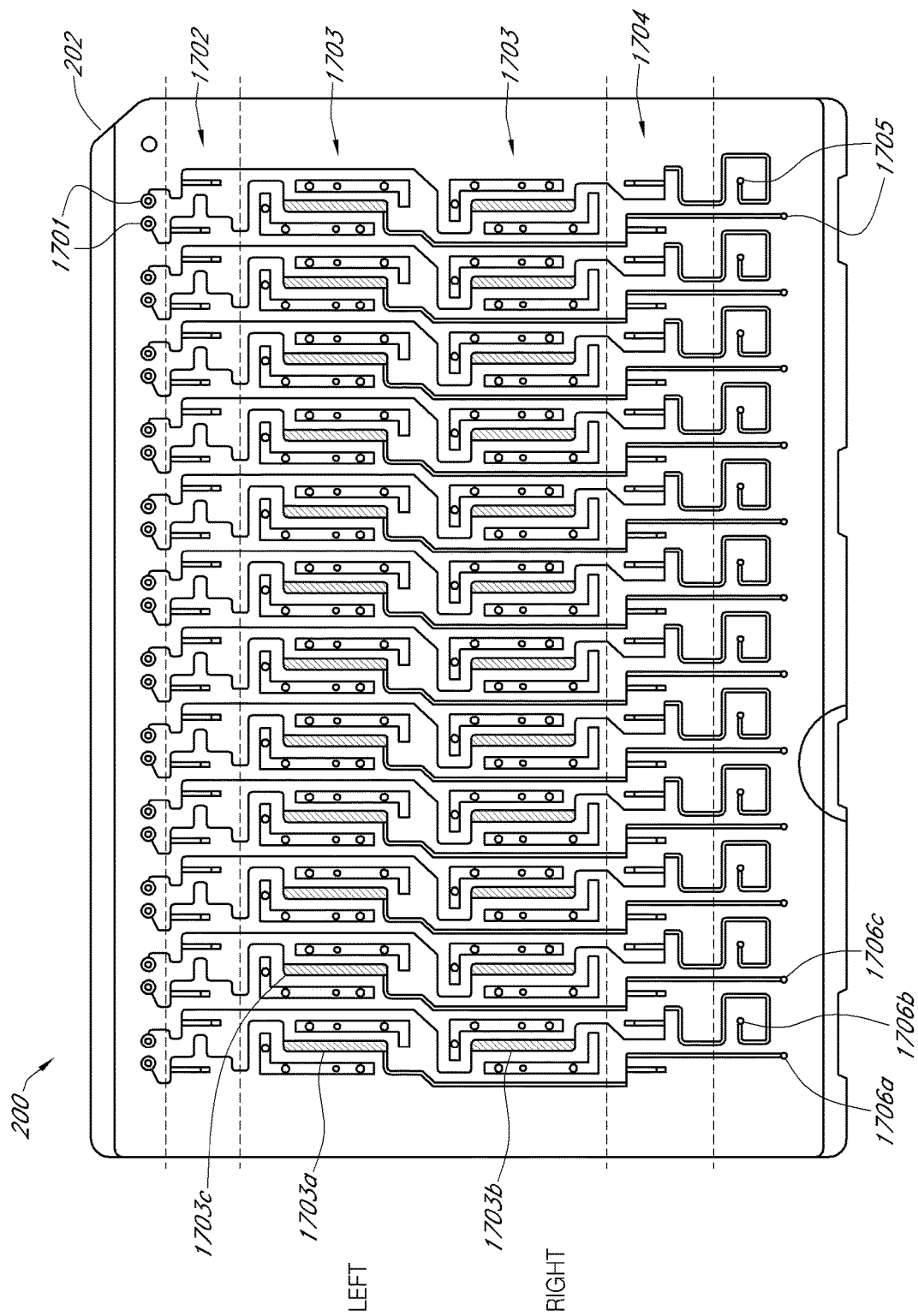
FIG. 3A illustrates a top-plan view of one possible microfluidic arrangement within certain embodiments of a microfluidic cartridge as described herein.

As illustrated in FIG. 2, the recessed bay 524 can be a portion of the receiving tray 520 that is configured to selectively receive the microfluidic cartridge 200. For example, the recessed bay 524 and the microfluidic cartridge 200 can have an edge 526 which is complementary in shape so that the microfluidic cartridge 200 is selectively received in, e.g., a single orientation. For example, the microfluidic cartridge 200 can have a registration member 202 that fits into a complementary feature of the bay. The registration member 202 can be, for example, a cut-out on an edge of the cartridge 200 (as shown in FIG. 3A) or one or more notches that are made on one or more of the sides. The skilled artisan will readily appreciate that complementarity between the cartridge and the receiving bay can be easily achieved using other suitable arrangements, e.g., a post or protrusion that fits within an aperture. By selectively receiving the cartridge 200, the recessed bay 524 can help a user to place the cartridge 200 so that the optical module 502 can properly operate on the cartridge 200. In this way, error-free alignment of the cartridges 200 can be achieved.

The receiving tray 520 may be aligned so that various components of the apparatus that can operate on the microfluidic cartridge 200 (such as, heat sources, detectors, force members, and the like) are positioned to properly operate on the microfluidic cartridge 200 while the cartridge 200 is received in the recessed bay 524 of the receiving tray 520. For example, contact heat sources on the heater substrate 600 may be positioned in the recessed bay 524 such that the heat sources can be thermally coupled to distinct locations on the microfluidic cartridge 200 that is received in the receiving tray 520.

Microfluidic Cartridge

Certain embodiments contemplate a microfluidic cartridge configured to carry out amplification, such as by PCR, of one or more polynucleotides from one or more samples. By cartridge is meant a unit that may be disposable, or reusable in whole or in part, and that may be configured to be used in conjunction with some other apparatus that has been suitably and complementarily configured to receive and operate on (such as deliver energy to) the cartridge.

By microfluidic, as used herein, is meant that volumes of sample, and/or reagent, and/or amplified polynucleotide are from about 0.1 µl to about 999 µl, such as from 1-100 µl, or from 2-25 µl, as defined above. Similarly, as applied to a cartridge, the term microfluidic means that various components and channels of the cartridge, as further described herein, are configured to accept, and/or retain, and/or facilitate passage of microfluidic volumes of sample, reagent, or amplified polynucleotide. Certain embodiments herein can also function with nanoliter volumes (in the range of 10-500 nanoliters, such as 100 nanoliters).

FIG. 3A is a top plan view of a microfluidic cartridge 200. The cartridge 200 may comprise a plurality of sample lanes 1706*a-c*. The lanes may lead to PCR chambers 1703 located on "left" and a "right" sides (i.e., rows) of the cartridge. As indicted in FIG. 3*a*, the lanes may provide inlet ports 1705 in a convenient location near the user. However, the lanes to which the ports are connected may then take independent paths to separate chambers 1703*a-c*. In the embodiment of FIG. 3*a*, for example, the first lane 1706*a* is in communication with the first chamber 1703*a* of the left side, the second lane 1706*b* is in communication with the first chamber of the right side 1703*b*, the third lane 1706*c* is in communication with the second chamber 1703*c* of the left side, etc. Each of the microfluidic lanes may also comprise microfluidic valves 1702, 1704, microfluidic gates, and microfluidic channels. These gates and valves may be configured, e.g., by thermal actuation, to facilitate timed release and controlled diffusion of certain fluids within the lanes 1706 of cartridge 200. The cartridge of this embodiment may comprise venting holes 1701 which prevent air from blocking fluid passage within the cartridge. Further description of various cartridge components, such as valves, may be found in e.g., U.S. Patent Application Publication 2009-0130719, incorporated herein by reference.

The microfluidic cartridge 200 may include a registration member 202, for example, a cutout, which corresponds to a complementary edge in the recessed bay 524 of the receiving tray 520*a,b* of the heater/optical modules 500*a*, 500*b*. The registration member 202 and the complementary edge 526 may allow for secure and correct placement of the microfluidic cartridge 200 in the receiving tray 520*a, b*.

In various embodiments, the components of a microfluidic networks in the sample lanes 1706 of the cartridge 200 may be heated by thermally coupling them with the heaters in a heater substrate 600. The heater substrate 600 may be configured to heat a sample mixture comprising amplification reagents and an amplification-ready polynucleotide sample and cause it to undergo thermal cycling conditions suitable for creating amplicons from the amplification-ready sample. The heater substrate 600 may be located on the cartridge 200 in some embodiments or in the recessed bay 524.

The microfluidic network in each lane may be configured to carry out nucleic acid amplification, such as by PCR, on an amplification-ready sample, such as one containing nucleic acid extracted from a sample. An amplification-ready sample may comprise a mixture of amplification reagents and the extracted polynucleotide sample. The mixture may be suitable for subjecting to thermal cycling conditions to create amplicons from the extracted polynucleotide sample. For example, an amplification-ready sample, such as a PCR-ready sample, may include a PCR reagent mixture comprising a polymerase enzyme, a positive control nucleic acid, a fluorogenic hybridization probe selective for at least a portion of the positive control nucleic acid and a plurality of nucleotides, and at least one probe that is selective for a target polynucleotide sequence. The microfluidic network may be configured to couple heat from an external heat source with the mixture comprising the PCR reagent and the extracted polynucleotide sample under thermal cycling conditions suitable for creating PCR amplicons from the extracted polynucleotide sample.

In various embodiments, the reagent mixture may comprise fluorescent or other optically-detectable labels for the detection of the generation of a desired amplicon. In some embodiments, multiple sets of primers and multiple labels can be used in a multiplex assay format, e.g., multiplexed PCR, where each of a plurality of different amplicons can be detected in a single reaction chamber, if present. For example, one assay chamber could include template nucleic acids from a test sample, positive control template nucleic acids, one or more primer pairs for the amplification of specific target sequences, one or more probes for the detection of target amplicons, and one or more primer pairs and a probe for the detection of positive control amplicons. Additionally, the skilled artisan will appreciate that in some embodiments, the microfluidic cartridge accommodates a negative control polynucleotide that will not produce an amplicon with primer pairs used to amplify target or positive control sequences.

In certain of the illustrated embodiments, the chambers 1703*a-c* respectively associated with each lane 1706*a-c* of a multi-lane cartridge 200 may perform independent amplification reactions. The results of the reactions for the first column of chambers (1703*a*, 1703*b*) for the first two lanes (1706*a*, 1706*b*) may then be simultaneously and independently measured using a detector head which comprises a "left" and a "right" light source-photodetector pair. That is each chamber 1703*a-b* of each lane 1706*a-b* may receive light from a separate light source and be observed by a separate photodetector simultaneously. In this manner, a variety of combinations of reactions may be performed in the cartridge efficiently. For example, in some embodiments, a plurality of amplification assays for the detection of a plurality target nucleic acids can be performed in one lane, a positive control and a negative control in two other lanes; or one or more amplification assays for the detection of one or more target nucleic acids, respectively, in combination with an internal positive control in one lane, with a negative control in a separate lane. In one particular embodiment, 2, 3, 4, 5, 6, or more assays are multiplexed in a single lane, with at least that number of fluorescently distinct fluorophores in the reaction chamber.

A microfluidic cartridge 200 may be constructed from a number of layers. Accordingly, one aspect of the present technology relates to a micro fluidic cartridge that comprises a first, second, third, fourth, and fifth layers wherein one or more layers define a plurality of microfluidic networks, each network having various components configured to carry out PCR on a sample in which the presence or absence of one or more polynucleotides is to be determined. In another embodiment, the microfluidic cartridge 200 can comprise a plurality of lanes, each including a reaction chamber, etched or molded in a single plane, such as in a molded plastic substrate, with each lane being closed by a cover layer, such as an adhesive plastic film layer. Embodiments with 8, 10, 12, 14, 16, 18, 20, 22, 24, 28, 30, or more lanes per cartridge are contemplated. For example, one suitable design is a single cartridge 200 having 24 reaction chambers, arranged in two rows of 12 reaction chambers, optionally having relatively aligned inlet ports. Further description of various cartridges and their components may be found in e.g., U.S. Patent Application Publication 2008-0182301 and U.S. Patent Application Publication 2009-0130719, incorporated herein by reference.

Heater Substrate

Figure 3B:
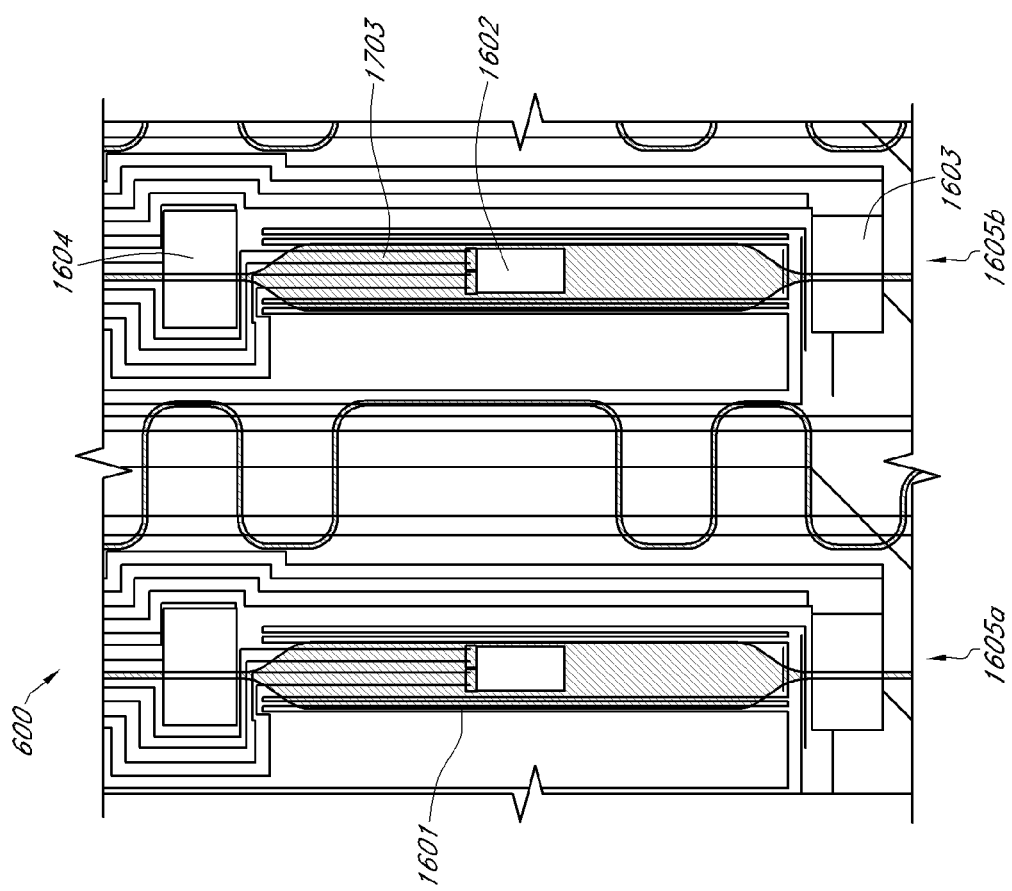
FIG. 3B illustrates the layout of a heater substrate in relation to the reaction chamber of certain of the embodiments.

Shown in FIG. 3B is a top plan view of certain embodiments of the heater substrate 600. Any type of heater can be used, including resistive, Peltier, or moving-fluid heaters, with either passive or active cooling contemplated. One of many possible embodiments includes a plurality of resistive heaters in thermal contact with each reaction chamber, preferably also including one or more temperature sensors. Because resistive heaters also exhibit some thermistor effect, i.e., their resistance changes with temperature, the resistive heaters themselves can double as temperature sensors, allowing precise temperature control of each reaction chamber while simplifying the product design. Although the heaters can be controlled in concert with each other, in some embodiments each reaction chamber can have one or more individual heaters in thermal contact therewith, such that the heaters are separately controllable and each reaction chamber can be heated and allowed to cool independently of the other reaction chambers. This allows different assays to be performed simultaneously in each of a plurality of reaction chambers. One particular resistive heater assembly for use with an individual reaction chamber is shown in FIG. 3B. In the embodiment shown in FIG. 3B, any combination of a top sensor heater/sensor 1604, a bottom heater/sensor 1603, a side heater/sensor 1601 and a center heater/sensor 1602 may be used to heat the reaction chamber located above. For ease of comprehension, an outline of the PCR chamber 1703 of certain of the embodiments is overlaid on the heater substrate. In certain embodiments, the heaters in the heater substrate 600 may be contact heaters. Such contact heaters may comprise (for example) a resistive heater (or network thereof), a radiator, a fluidic heat exchanger and a Peltier device. The contact heat source may be configured in the recessed bay 524 to be thermally coupled to one or more distinct locations of the microfluidic cartridge 200 received in the receiving tray 520*a, b* whereby the distinct locations are selectively heated. The contact heat sources may each be configured in the heater substrate 600 to be independently thermally coupled to a different distinct location in a microfluidic cartridge 200 received in the receiving tray 520*a,b* whereby the distinct locations are independently heated. The contact heat sources can advantageously be configured to be in direct physical contact with distinct locations of a microfluidic cartridge 200 received in the receiving tray 520*a,b*. In various embodiments, each contact source heater may be configured to heat a distinct location having an average diameter in 2 dimensions from about 1 millimeter (mm) to about 15 mm (typically about 1 mm to about 10 mm), or a distinct location having a surface area of between about 1 mm about 225 mm (in some embodiments between about 1 mm and about 100 mm, or in some embodiments between about 5 mm and about 50 mm).

The heater substrate 600 may be organized into "lanes" 1605*a, b* paralleling the structure of the lanes 1706*a-c* of the cartridge 200. In some embodiments, the heater substrate 600 may include 24 heater lanes 1605*a*, 1605*b* corresponding to the sample lanes 1706 of cartridge 200. When the microfluidic cartridge 200 is placed in the recessed bay 524 of the receiving tray 520*a,b*, the components of the cartridge 200 may be aligned adjacent to, and above, the corresponding heaters in the heater substrate 600. When the microfluidic cartridge 200 is placed in the recessed bay 524, the heaters may be in physical contact with the respective components. In some embodiments the heaters remain thermally coupled to their respective components, e.g., through one or more intermediate layers or materials, though not in direct physical contact. Further description of lanes may be found e.g., in U.S. Patent Application Publication 2009-0130719, herein incorporated by reference.

In some embodiments, multiple heaters may be configured to simultaneously and uniformly activate to heat their respective adjacent cartridge components of the microfluidic network in the microfluidic cartridge 200. Each heater may be independently controlled by a processor and/or control circuitry used in conjunction with the apparatus described herein. Generally, the heating of microfluidic components (gates, valves, chambers, etc.) in the microfluidic cartridge 200, is controlled by passing currents through suitably configured micro-fabricated heaters. Under control of suitable circuitry, the lanes 1706 of a multi-lane cartridge can then be heated independently, and thereby controlled independently, of one another. Furthermore, as is described in more detail below, the individual heaters 1601-1604 can be heated independently, and thereby controlled independently, of one another. This can lead to a greater energy efficiency and control of the apparatus, because not all heaters are heating at the same time, and a given heater is receiving current for only that fraction of the time when it is required to heat.

The heater substrate 600 may also include one or more heat sensors. In order to reduce the number of sensor or heaters required to control the heaters in a heater lanes 1605*a*, 1605*b*, the heaters may be used to sense temperature as well as heat, and thereby obviate the need to have a separate dedicated sensor for each heater. For example, the impedance and/or resistance of some materials change with the surrounding temperature. Accordingly, the resistance of heater/sensors 1601-1604 may be used as an indication of temperature when the sensors are not being actively heated.

In some embodiments, the heaters in the heater substrate 600 may be designed to have sufficient wattage to allow the heaters to be grouped in series or in parallel to reduce the number of electronically-controllable elements, thereby reducing the burden on the associated electronic circuitry. Heaters that are grouped together in this manner would be operated under synchronized and substantially simultaneous control.

In some embodiments, the reaction chamber heaters on opposite sides of the second stage heaters can be grouped and configured to operate under synchronized control. For example, in some embodiments, the PCR/amplification heaters 1601-1602 can be grouped and configured to operate under synchronized control. Alternative groupings and configurations can be applied to other heater groups of the PCR/amplification heaters 1601-1604. The PCR/amplification heaters 1601-1604 may be configured to operate individually and independently or they can be configured to operate in groups of two (pairs), three (thirds), four, five or six.

In some embodiments, the heating may be controlled by periodically turning the current on and off to a respective heater with varying pulse width modulation (PWM), wherein pulse width modulation refers to the on-time/off-time ratio for the current. The current can be supplied by connecting a micro fabricated heater to a high voltage source (for example, 30V), which can be gated by the PWM signal. In some embodiments, the device may include 48 PWM signal generators. In some embodiments there will be two PWM signal generators associated with each reaction chamber. Operation of a PWM generator may include generating a signal with a chosen, programmable period (the end count) and granularity. For instance, the signal can be 4000 us (micro-seconds) with a granularity of 1 us, in which case the PWM generator can maintain a counter beginning at zero and advancing in increments of 1 us until it reaches 4000 us, when it returns to zero. Thus, the amount of heat produced can be adjusted by adjusting the end count. A high end count corresponds to a greater length of time during which the micro fabricated heater receives current and therefore a greater amount of heat produced.

In various embodiments, the operation of a PWM generator may also include a programmable start count in addition to the aforementioned end count and granularity. In such embodiments, multiple PWM generators can produce signals that can be selectively non-overlapping (e.g., by multiplexing the on-time of the various heaters) such that the current capacity of the high voltage power is not exceeded.

Multiple heaters can be controlled by different PWM signal generators with varying start and end counts. The heaters can be divided into banks, whereby a bank defines a group of heaters of the same start count. Control of heating elements, and cooling elements, if present, in certain embodiments is discussed in further detail below.

Optical Module

Figure 4A:
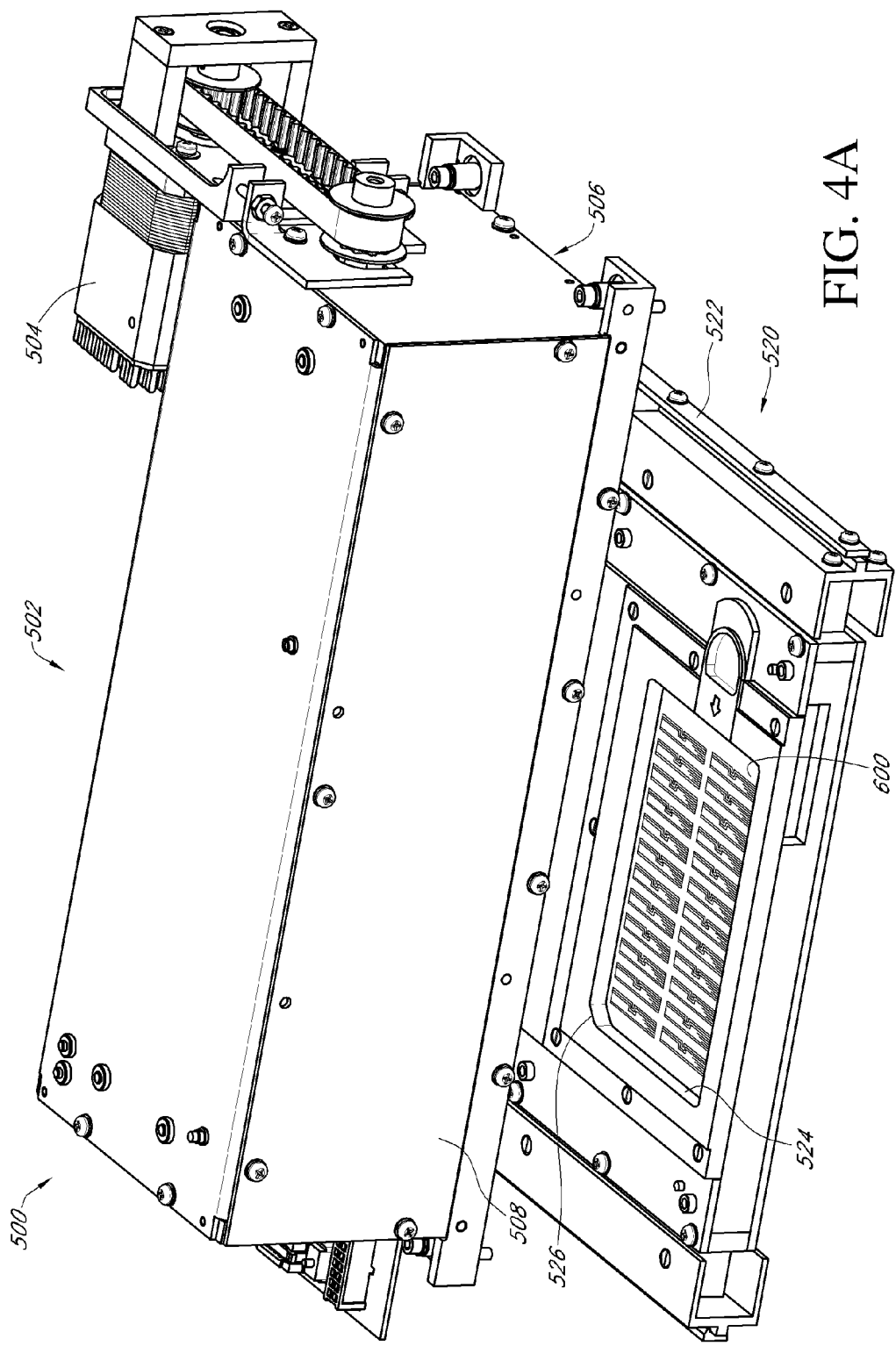
FIG. 4A illustrates an exterior view of the optical module including the detector head of certain of the embodiments described herein.
Figure 4B:
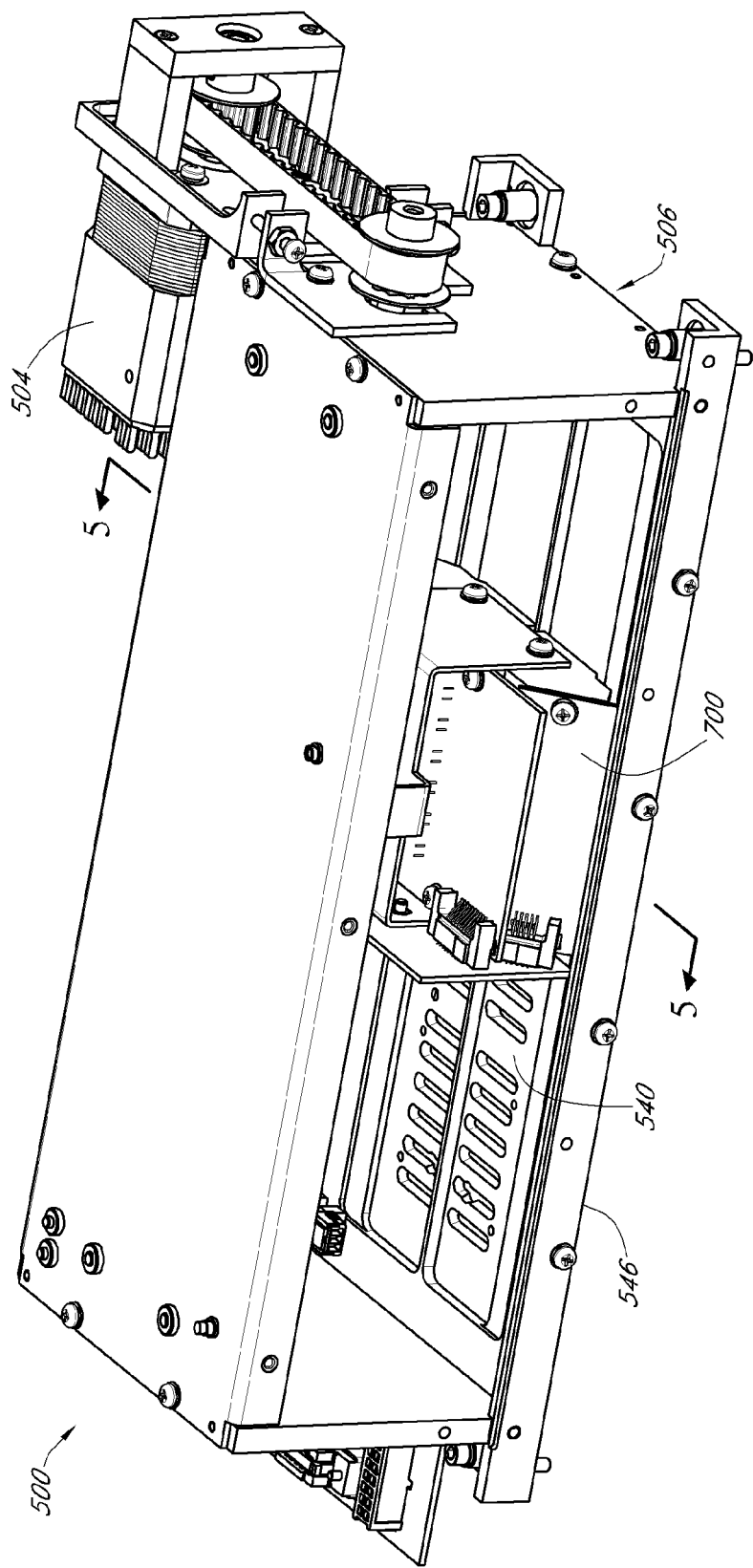
FIG. 4B illustrates a view of the optical module of FIG. 4A with a side cover removed.
Figure 4C:
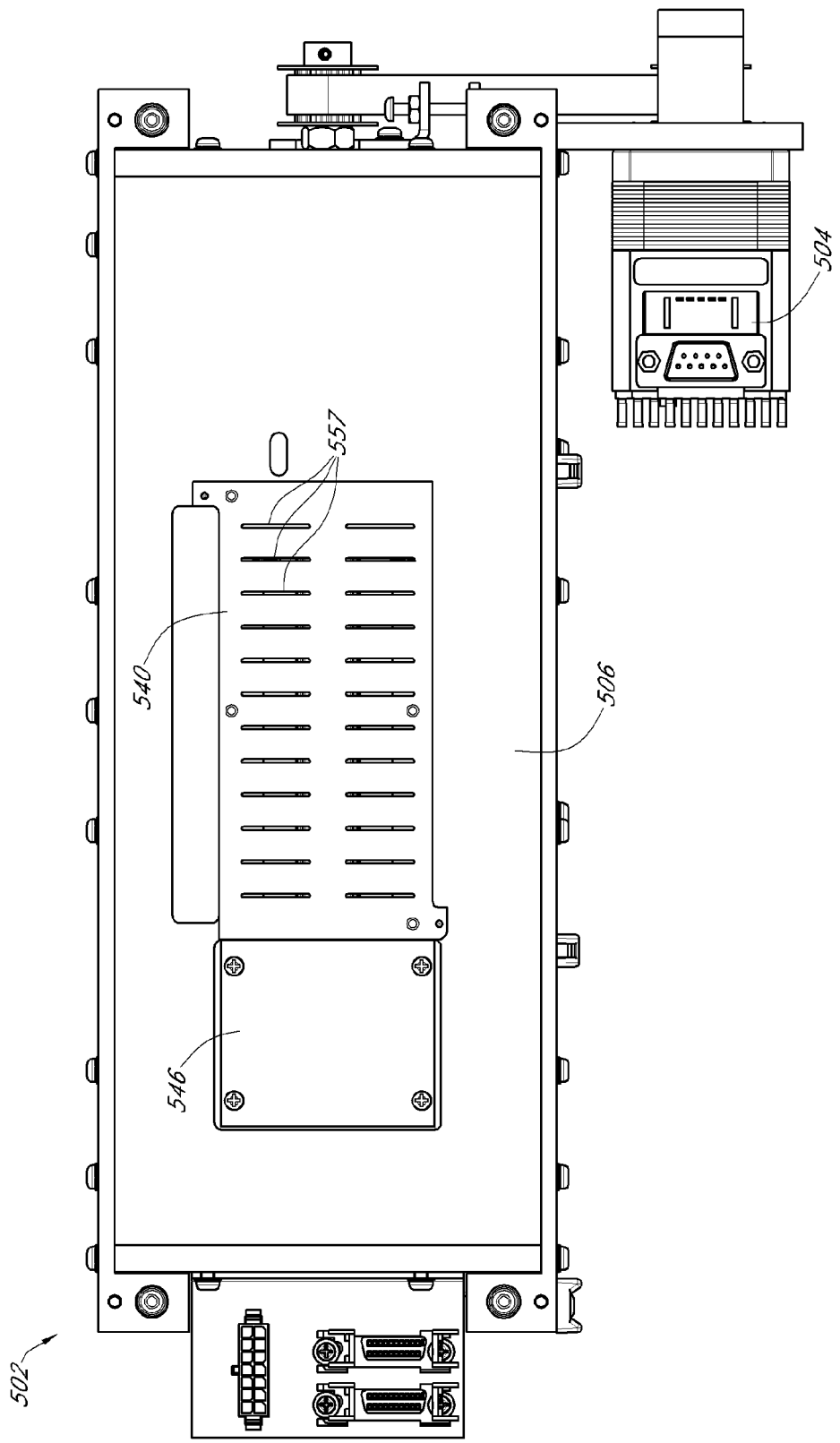
FIG. 4C illustrates a bottom view of the optical module of FIG. 4A.

FIGS. 4A-C illustrate the heater/optical module 500 of the detection apparatus 10 found in certain embodiments. The heater/optical module 500 may comprise an optical module 502 and a receiving tray 520 or a portion of the receiving tray. FIG. 4A shows one embodiment of the enclosed optical module 502 having a motor 504 externally attached thereto for driving movement of detector head 700. The detector head 700 may be housed inside the optical module 502. FIG. 4A illustrates the receiving tray 520 coupled to a bottom side 506 of the optical module 502. The receiving tray 520 may receive a cartridge 200 comprising samples upon which detection is to be performed. After receiving the samples, the receiving tray 520 may be moved (e.g., mechanically or manually) on rails 522 to a position underneath the optical module 502. In some embodiments, described in greater detail below, the receiving tray may comprise an auto-loading device, which automatically aligns the cartridge once positioned beneath the optical module 502. In some embodiments, a recessed bay 524 of the receiving tray 520 may contain a heater substrate 600. In some embodiments, the receiving tray may subsequently be raised to place the cartridge in contact with the optical module 502, such as in contact with an aperture plate 540 at the base of the optical module 502

FIG. 4B illustrates an embodiment of the optical module 502 with a front panel 508 removed to show the interior of the optical module 502. Shown in FIG. 4B is the detector head 700. As described in detail below, movement of the detector head 700 may be driven by the motor 504 to move laterally across the interior of the optical module 502 to provide optical scanning and detection on the cartridge 200 when the cartridge 200 is positioned below the optical module 502 in the receiving tray 520. Shown in FIG. 4B is an aperture plate 540, positioned on the bottom side 506 of the optical module 502.

FIG. 4C provides a bottom plan view of the optical module 502. Shown in FIG. 4C is the aperture plate 540 and a normalizer plate 546 attached to the bottom of the 506 of the optical module 502. The normalizer plate may be used to calibrate the light source-photodetector pairs of the detector head. The normalizer plate 546 preferably comprises a one or more components having known, standardized optical characteristics, and is configured to calibrate, standardize, or confirm proper operation of the detector head 700 and associated circuitry. The normalizer plate 546 may extend into the optical module and the detector head 700 may be positioned over the normalizer plate. In some embodiments, prior to the start of cartridge optical measurements the detector head 700 is calibrated using the known properties of the normalizer plate 546. If the detector head 700 is not working properly, corrective action may be taken, such as including an offset in the measurements or notifying the user of the error. In some embodiments, the normalizer plate may be made of optically-transparent material such as polycarbonate mixed with a highly fluorescent dye, or other standardized chromophore or fluorophore. In one embodiment, the normalizer plate includes a standardized chromophore or fluorophore for each channel or color in the detector head 700.

As shown in FIG. 4C, the aperture plate 540 contains apertures 557. The dimensions of apertures 557 are such that the detector's light sources and photodetectors may have access to (optically excite or view) the contents in cartridge 200's reaction chambers when the detector is moved to a plurality of positions within optical module 502. That is, when a light source-photodetector pair of the detector is located in a position over a particular aperture light may travel from the light source and reach the chamber reactor through the aperture 557. The fluorescing reagents in the reaction chamber may then be visible to the photodetector via the aperture 557.

Detector Head

Figure 5:
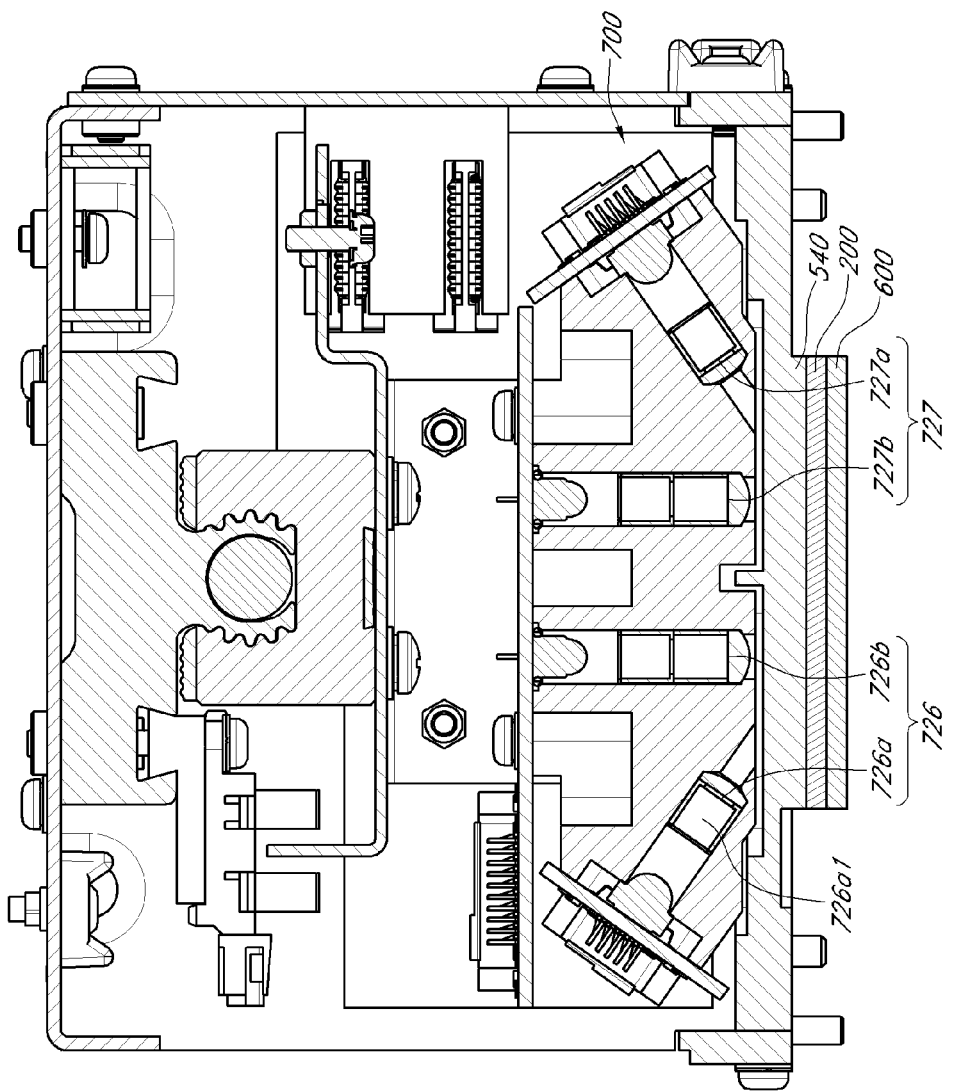
FIG. 5 illustrates a detector head used within the optical module of certain of the embodiments along the line 13 of FIG. 4B.

FIG. 5 shows a cross-section of the detector head 700 taken along line 13 of FIG. 4B. The detector head 700 may be configured to optically excite and/or monitor fluorescence emitted in connection with detection of from one or more polynucleotides present in the reaction chambers 1703. Note that a positive result (presence of a target amplicons) may be indicated by increased fluorescence or decreased fluorescence, depending on assay design. For example, when the assay involves a fluorophore and a quencher, the quencher may quench fluorescence when the target is present, or in other assay designs, when the target is absent. The system may comprise, for example, a plurality of detector pairs, e.g., 3, 4, 5, 6, 7, 8, 9, 10, 11, 12, 13, 14, 15, 16, 17, 18, 19, 20, 21, 22, 23, 24, or more, such as the detector pair 726. Each detector pair 726 can be comprised of a light source 726a, such as a light-emitting diode (LED), and a corresponding light detector 726b, such as a photodiode. The light source 726a may selectively emit light in an absorption band of a fluorescent probe. The light detector 726b may selectively detect light in an emission band of the fluorescent probe, wherein the fluorescent probe corresponds to a polynucleotide probe or a fragment thereof. In certain embodiments the light source 726a may comprise a bandpass-filtered diode that selectively emits light in the absorption band of the fluorescent probe. Light detector 726b may comprise a bandpass filtered photodiode that selectively detects light in the emission band of a fluorescent moiety, e.g., emission from a fluorescent probe. In certain embodiments, a filter 726a1, such as a bandpass filter may be applied to the light source 726a's light. The light from the light source 726a passes through a filter before passing through the sample in the micro-fluidic channel (300 g deep in certain embodiments). In certain embodiments, the optical path-length for the light from the reaction chamber to the light detector 726b may be very small. The incident light from light source 726a generates fluorescence in the reaction chamber. Light from the reaction chamber then travels to the light detector 726b. Certain embodiments seek to mitigate any undesired light from entering the detector and thereby adversely affecting the light signal from the reaction chamber.

In some embodiments, each one of the plurality of detector pairs may be arranged along the length of the detector head 700 in rows. That is, behind the pairs 726 and 727 illustrated in FIG. 5 may be another column of pairs in a similar or same orientation. For the sake of explanation, a collection of cartridges or detector pairs along the length of the cartridge are referred to as a "row" and those along the width as a "column". Thus, the vertical direction in FIGS. 3A and 6 indicates a "column" and the horizontal direction a "row". Certain embodiments contemplate six or more columns of such detector pairs. In these embodiments, there would be 12 detector pairs in total (two rows of six) with two detector pairs per column, permitting 12 separate and simultaneous detections.

Each light source, such as for example light source 726a, may be configured to produce light of a wavelength specific to a specific fluorescent moiety associated with, e.g., a probe, contained in the reaction chambers. Each light detector, such as for example 726b, may be configured to detect the light emitted from the fluorescent probes associated with the light produced by the light emitter in the detector pair. The detector pairs may be configured to independently detect a plurality of fluorescent moieties, e.g., different fluorescent probes, having different fluorescent emission spectra, wherein in each reaction chamber, emission from each fluorescent probe is indicative of the presence or absence of one particular target polynucleotide or a fragment thereof. Although folded light paths can be used, one embodiment utilizes a detector and emitter pair where each is in direct optical contact with the reaction chamber, preferably simultaneously in such contact. Optionally, the detector and emitter of a pair are aligned with the reaction chamber along lines that substantially intersect at an acute angle at the reaction chamber. The angle can be, for example, between about 5 and 70 degrees, preferably between about 8 and 60 degrees, more preferably between about 10 and 50 degrees.

In some embodiments, the detector head includes two rows of photodetector and light source pairs that correspond to two rows of reaction chambers of microfluidic cartridges, when present in the apparatus. For example, the detector head can include a first or top row of six photodetector and light source pairs, and a second, or bottom row of photodetector and light source pairs, that are configured to query first and second rows of reaction chambers within a microfluidic cartridge, respectively.

Figure 6:
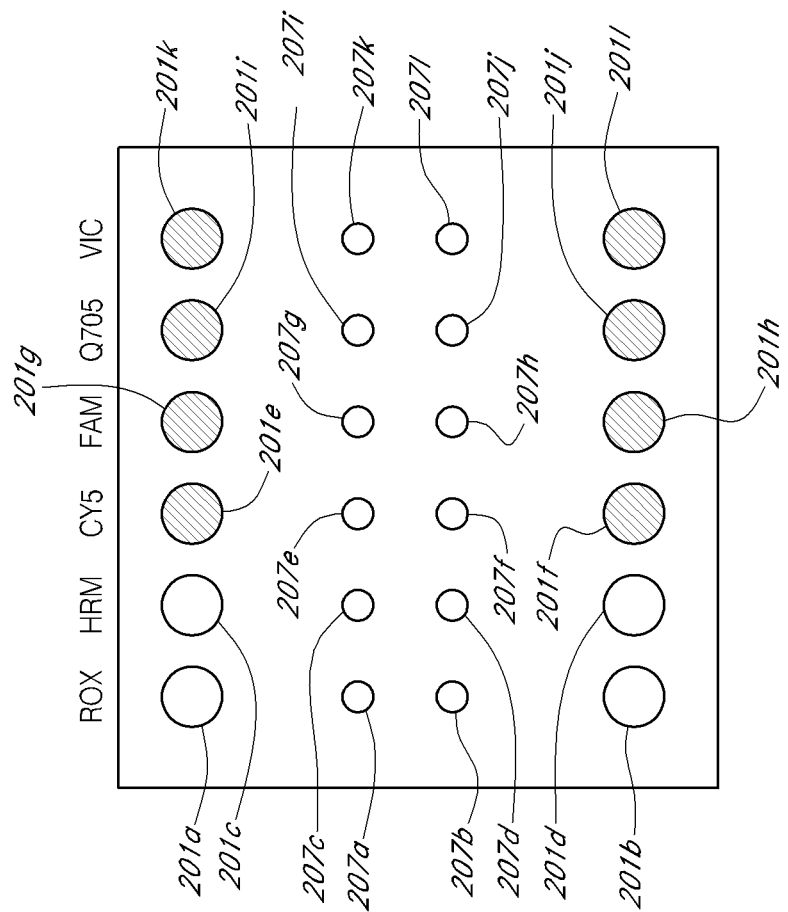
FIG. 6 depicts the layout of the light sources and optical detectors as used in certain of the embodiments of the detector head disclosed herein.

FIG. 6 illustrates one possible photodetector and light source layout implemented in certain embodiments of the detector. The first column comprises ROX light emitters 201a, 201b and corresponding detectors 207a, 207b. The second column comprises HRM light emitters 201c, 201d and corresponding detectors 207c, 207d. The third column comprises CY5 light emitters 201e, 201f and corresponding detectors 207e, 207f. The fourth column comprises FAM light emitters 201g, 201h and corresponding detectors 207g, 207h. The fifth column comprises Q705 light emitters 201i, 201j and corresponding detectors 207i, 207j. The sixth column comprises VIC light emitters 201k, 201l and corresponding detectors 207k, 207l. In some instances, the detectors and emitters are selected with reference to particular fluorophores to be used in an assay. In the embodiment illustrated in FIG. 6, the first or top row detector and light source pairs comprises a plurality of photodetector and light source pairs, e.g. emitters 201a, 201c, 201e, 201g, 201i, and 201k and detectors 207a, 207c, 207e, 207g, 207i, and 207k. The second or bottom row detector and light source pairs comprises a plurality of photodetector and light source pairs, e.g. emitters 201b, 201d, 201f, 201h, 201j, and 201l and detectors 207b, 207d, 207f, 207h, 207j, and 207l. A summary of the properties of exemplary emitters and detectors is shown in Table 1 below.

TABLE 1

| Color (Spec) | Dye (Assay) | Wavelength Name (Ex/Em) | Software | CT# |
|---|---|---|---|---|
| Green | FAM | 470/510 | FAM | 4 |
| Yellow | TET, VIC | 530/555 | VIC | 6 |
| Orange | Texas Red, ROX | 585/610 | Cal Red/ROX | 1 |
| Red | Cy5 | 625/660 | Cy5 | 3 |
| Crimson | Cy5.5 | 680/715 | Cy5.5 | 5 |
| ultraviolet | null | ultraviolet | HRM | 2 |

The exemplary arrangement of photodetectors and light sources depicted in FIG. 6 can inhibit cross-talk between detection columns. That is, the wavelength range for each emitter detector pair may be selected so as to possess a minimal overlap with its neighboring emitter-detector pairs. Thus, for example, where CT# refers to the column of a particular emitter-detector pair in a 6-column detector head, Ex is the excitation wavelength of a fluorophore, and Em is the emission wavelength, it will be apparent that adjacent emission wavelengths are not adjacent to each other in the detector head. That the row HRM's dye is null merely indicates that a variety of dyes, not required for this particular example, may be used. In some embodiments, HRM refers to a "High Resolution Melt" and a corresponding light source for this photodetector may comprise an LED operating in the ultraviolet spectrum. One will recognize that the columns may be arranged in alternative variations and that alternative selections of light emitting sources and detectors may be substituted for those shown.

The light-emitter and photodetector pairs of each column may be calibrated using the normalizer plate. After calibration, the detector head may be moved to a position such that a first column of light-emitter and photodetector pairs is located over a first group of lanes such that each light-emitter and photodetector pair has access to a reaction chamber of the lanes. Detection of the reaction chambers in the first group of lanes will then be performed using the first column of emitters/detectors. Then, the detector head may be moved to a second position such that the first column is over a second group of lanes and the second column is over the first group of lanes. Detection of the reaction chambers in the second group of lanes will then be performed using the first column of emitters/detectors and detection of the reaction chambers in the first group of lanes will then be performed using the second column of emitters/detectors. The process may continue until each column has passed over each lane. Thus, for N columns of detectors and M columns of chambers, the detector will perform detections at least M+N−1 positions. For example, in the embodiments of FIG. 11 there are 6 columns. For a cartridge comprising 12 lanes, the detector would need to move between at least 17 positions (18 if the calibration position is considered).

Figure 7:
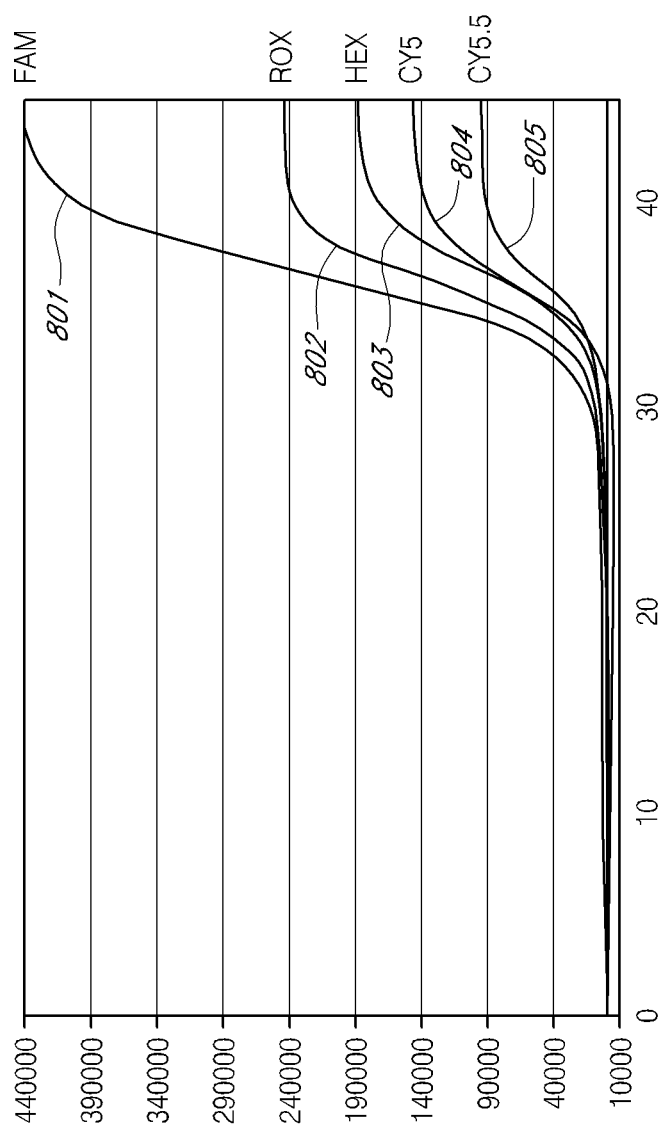
FIG. 7 is a graph of the fluorescence versus time of using real time PCR of target nucleic acids performed in an apparatus of certain embodiments as described herein.

FIG. 7 depicts the final results after operation of certain of the embodiments. Plotted are the detected fluorescent levels for each light emitter-photodetector pair 801-805 over time for a single reaction chamber (or reactor) associated with a single lane. After a sufficient number of iterations (approximately 30 in this example) of the annealing and denaturing protocol, the detectors identify increasing levels of fluorescence within the reactor.

Chamber Plate

Certain of the present embodiments relate to the plating surrounding and including the chamber layer. Particularly, certain embodiments contemplate the manufacture of an aperture layer comprising characteristics that advantageously facilitate consistent results across trials of the heating/detection module, as discussed in further detail below.

Figure 8:
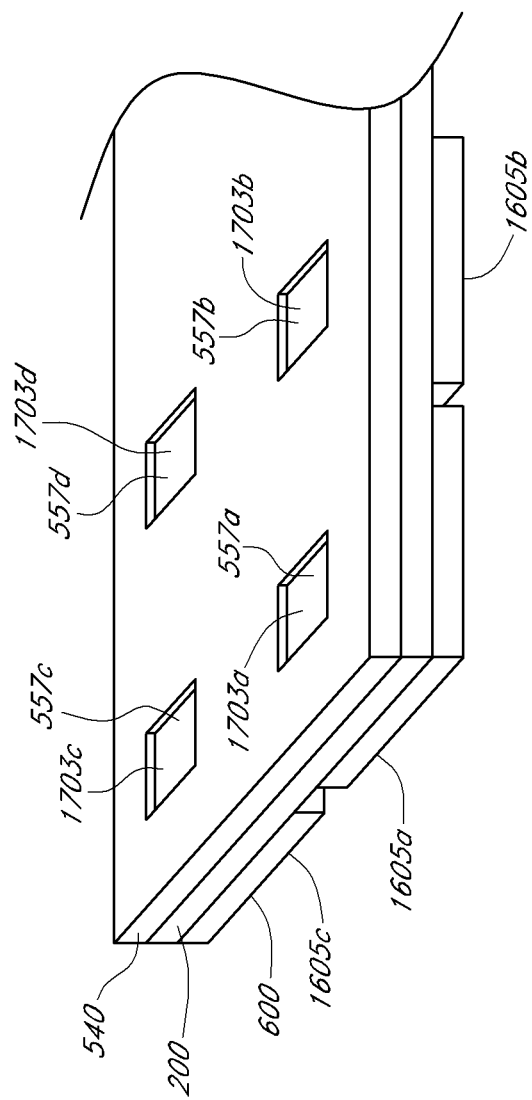
FIG. 8 is an abstract depiction of certain of the chamber, aperture, and heating layers found in certain of the embodiments as described herein.
Figure 9C:
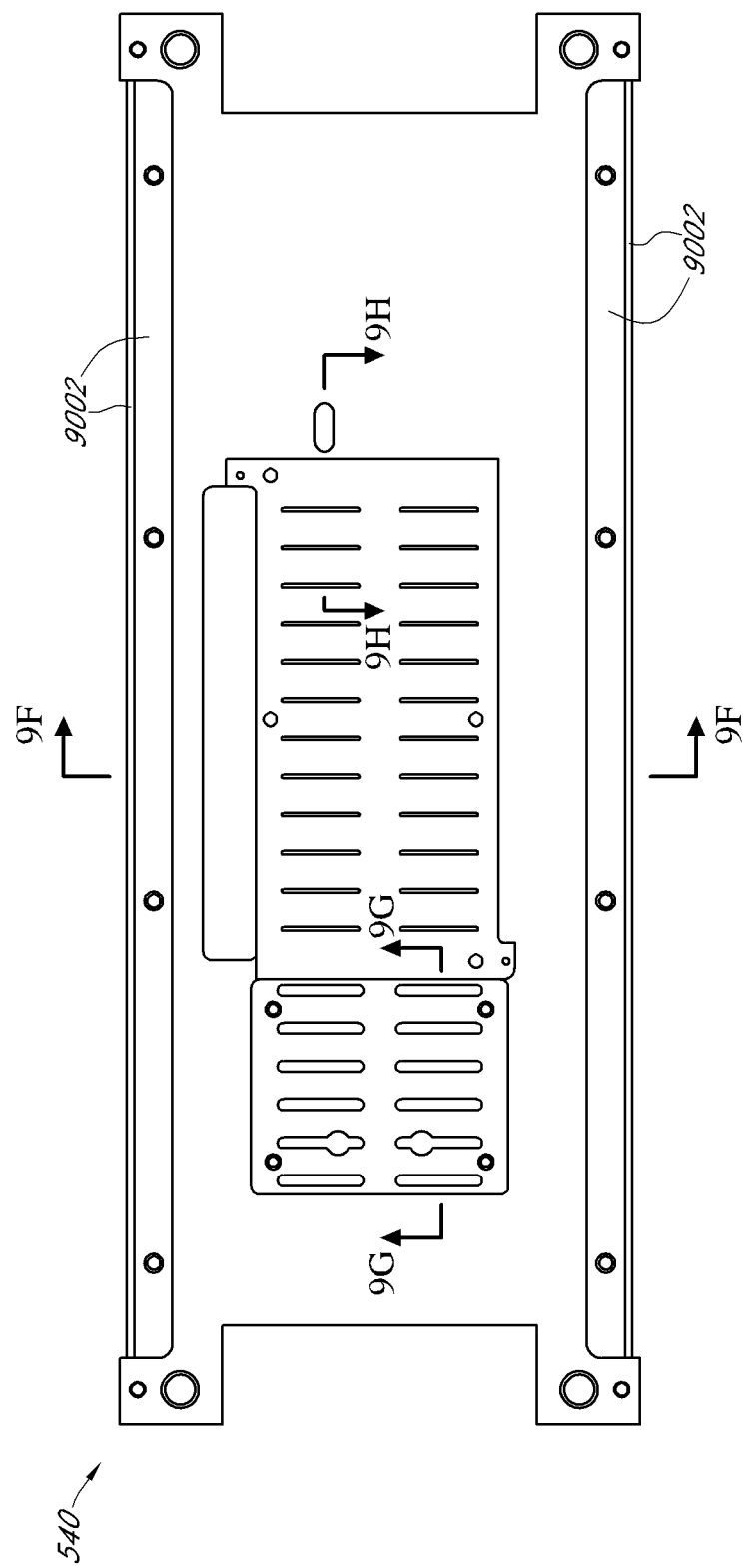
Figure 9E:
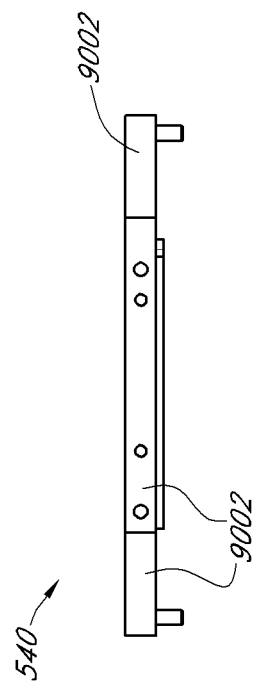
Figure 9D:
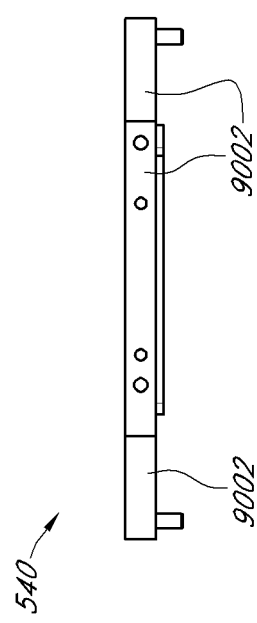
Figure 10A:
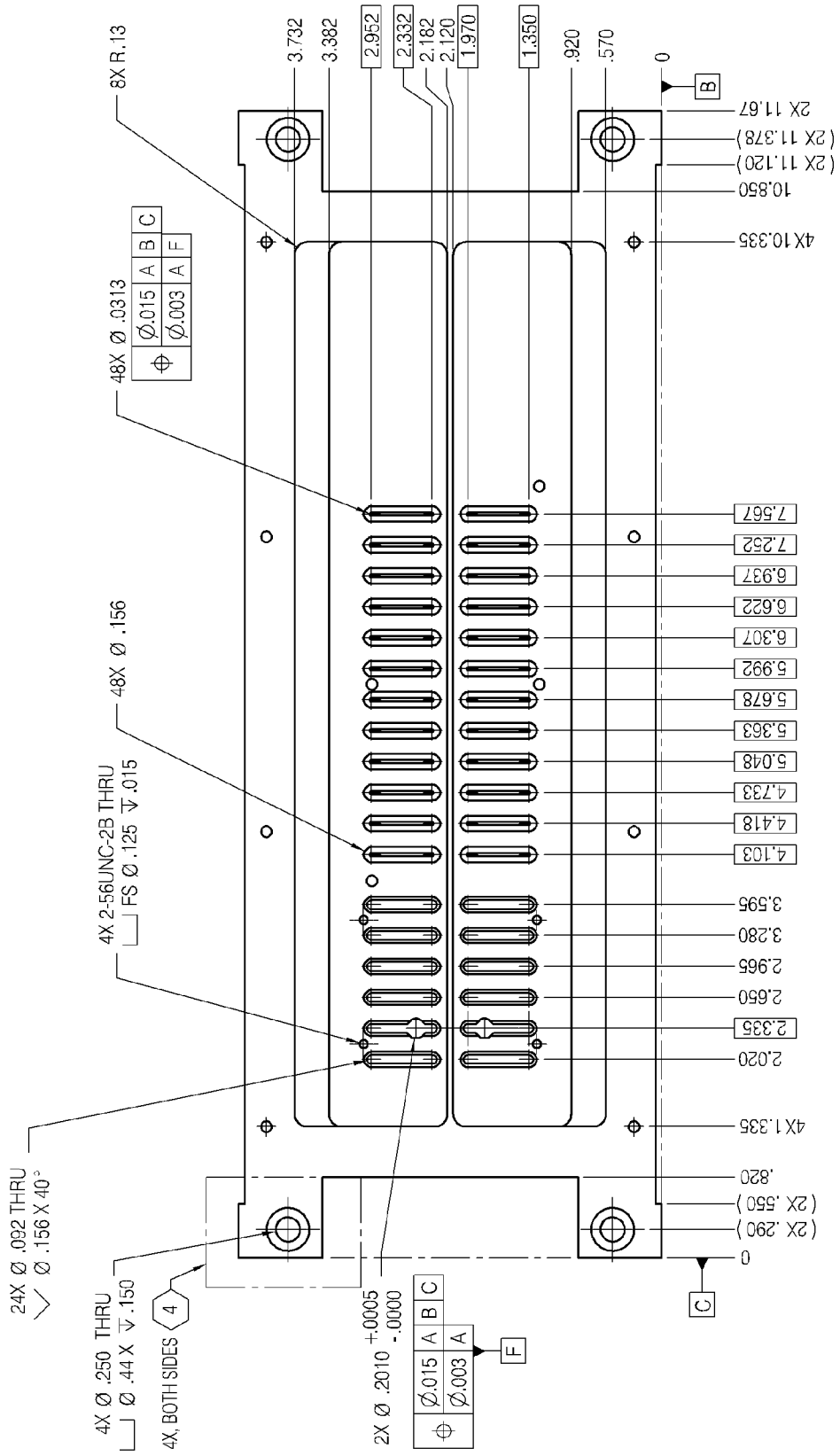
Figure 10B:
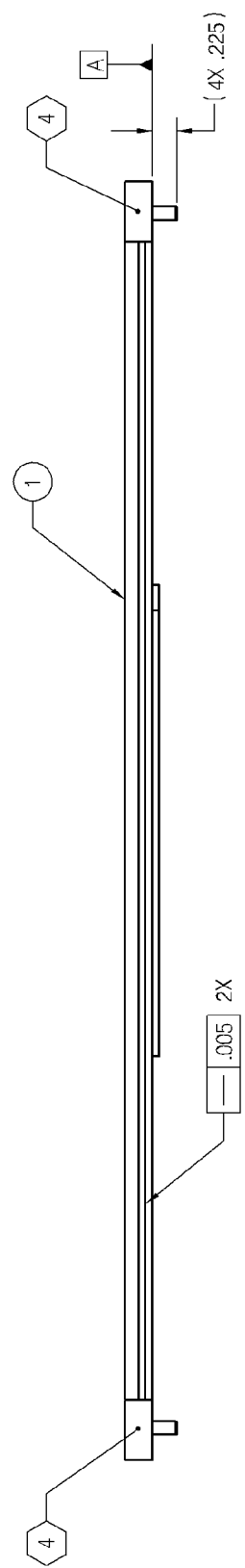
Figure 10C:
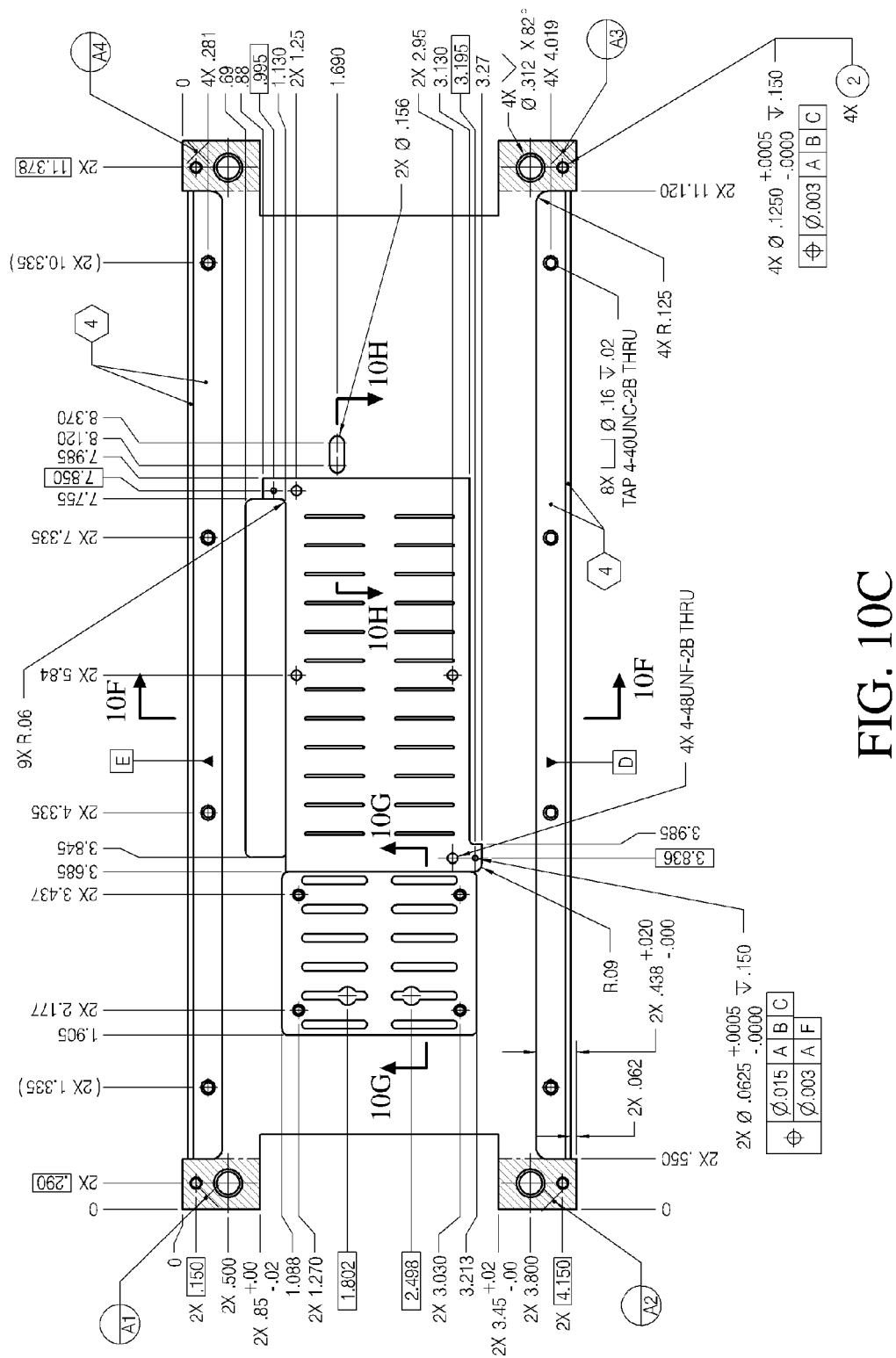
Figure 10E:
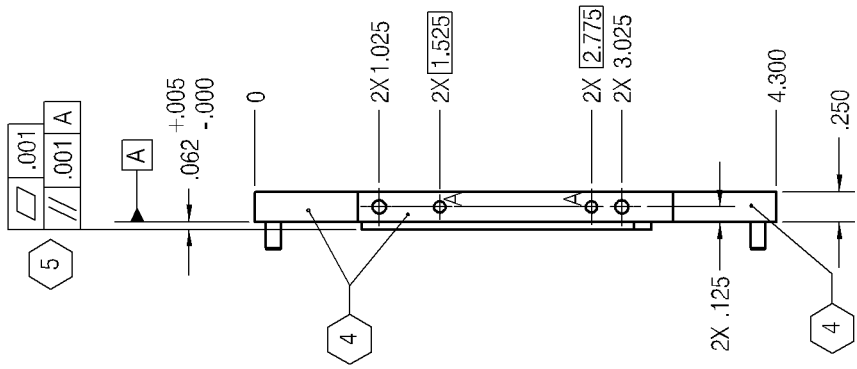
Figure 10D:
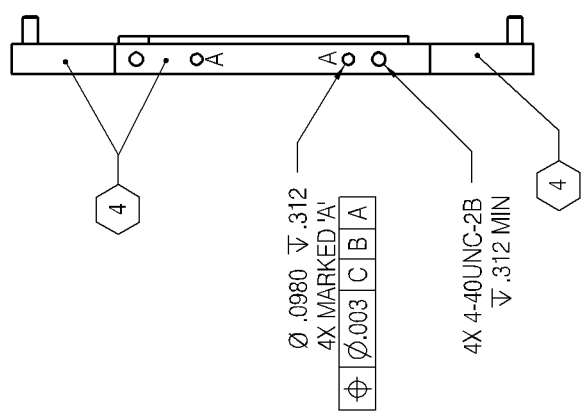

FIG. 8 illustrates the plating arrangement found in certain embodiments of the scanning thermocyler's optical module and the associated receiving tray and cartridge. When the cartridge is brought within proximity of the aperture layer 540 of the optical module 500a, the thermal layer 600, chamber layer 200 (which may comprise a chamber substrate), and aperture layer 540 may be situated as depicted in the embodiment of FIG. 8. As discussed above, the chamber layer 200 may comprise a plurality of reaction chambers 1703a-d, which may be located so as to be thermally controlled separately from one another, or in groups. Thermal layer 600 may comprise a plurality of thermal units 1605a, 1605b, 1605c. FIG. 8 is a simplified, abstract diagram of the above description, and certain features of the microfluidic pathway are not shown. In certain embodiments the thermal units may be both mechanically and thermally disconnected from one another (as illustrated by their physical separation in FIG. 4). However, in other embodiments, the thermal units may be each placed within a same substrate material, but spaced such that they remain thermally disconnected, as discussed above. Thus, it is possible for the thermal units to be thermally separated, but not mechanically separated.

In this manner, each thermal unit may be associated with one or more reaction chambers 1703a-d, separately from the remaining reaction chambers. In agreement with the protocol specified for each reaction chamber, the thermal units may successively heat and/or cool their corresponding chamber appropriately. For example, thermal unit 1605c may cool and/or heat chamber 1703a such that the temperature of chamber 1703a is substantially independent of the cooling and thermal state of the chamber 1703a. While heating may be accomplished by running current through a microfluidic or electronic circuit, cooling may be "passive" in that only convection between the microfluidic chamber and is used to reduce the chamber's temperature. The thermal units 1605a, 1605b, 1605c may be controlled using a closed loop control system.

In some embodiments, aperture plate 540 may be located over the chamber layer 200 and can provide pressure to chamber layer 200 to facilitate heating and cooling of the microfluidic cartridge, e.g., the chamber layer, by thermal layer 600. The aperture plate can include a plurality of apertures 557a-d to facilitate each photodetector's 726b observation of an individual reaction chambers 1703a-d. In the absence of aperture plate 540, and depending on the configuration of the thermal layer 600 and chamber layer 200, chamber layer 200 may "warp" and/or be sufficiently flexible that the thermal communication between chambers and the respective thermal units is inconsistent. Inconsistent heating and cooling can lead to less accurate execution of the protocols and less precise and accurate results. As described above, significant warping may restrict the optical head from lateral movement. Thus, the thickness of the aperture plate must be appropriately selected to facilitate a proper light path between each reaction chamber and the light sources and photodetectors while still ensuring proper heating and cooling of the chamber layer. If the aperture layer is too thick, the distance from the photodetector 726b to the chamber may be too great, undesirably attenuating the fluorescence reading from the reaction chamber. In addition to increasing the distance to the reaction chamber, an aperture layer 540 which is too thick or too heavy will place too much pressure on the reaction chamber, causing convection to be too great. Conversely, if the aperture layer 540 is too thin it may not prevent the chamber layer 200 from bending and warping, and the aperture layer 540 may bend and warp itself. Warping of apertures 557a-d or the chambers 1703a-d may deflect light from the light source 726a and prevent accurate readings by photodetector 726b.

Accordingly, the embodiments described herein provide aperture layers that advantageously avoid the drawbacks described above. In certain embodiments, the aperture layer 540 is made, at least in part, of steel. In these embodiments, steel provides the appropriate strength, density and resistance to deflection desired for operation. Furthermore, the steel may provide low self-fluorescence and is therefore less likely to adversely affect the reading of photodetector 726b. The steel may also be electrochemically treated to diminish its self-fluorescence and thereby be less likely to adversely affect the reading of the photodetector. In certain embodiments, the aperture layer may instead comprise black nickel (Ni), i.e. Ni with a colorant added to it to reduce self-fluorescence. Certain embodiments contemplate combinations of these different materials and electrochemical treatments. In certain embodiments, the aperture layer 540 is made of aluminum and when secured by the adjoining support panels 500, 506, and 546, provide the appropriate strength. The aluminum may be electrochemically plated with an anodic oxide finish, e.g., with a black colorant added to reduce self-fluorescence.

The illumination optics may be designed so that the excitation light falling on the reaction chamber, or reactor, is incident along an area that is similar to the shape of the reactor. As the reactor may be long and narrow, the illumination spot may also be long and narrow, i.e., extended, as well. Thus the shape of apertures 557a-d may be designed with consideration both to the dimensions of the reaction chamber underneath, as well as to the relative positions of the corresponding light emitter and photodetector. The length of the spot may be adjusted by altering a number of factors, including: the diameter of the bore where the photodetector 726b is placed (the tube that holds the filter and lens may have an aperturing effect); the distance of the photodetector 726b from the PCR reactor; and the use of proper lens in photodetector 726b.

Force Member

In certain embodiments, the receiving tray 520 places the chamber layer 200 in proximity to the thermal layer 600 or aperture layer 540, but does not mechanically couple and/or thereby place the layers in contact with one another. In this manner, the chamber layer 200 may be thermally, but not mechanically, coupled to the thermal layer 600. In other embodiments, the receiving tray places the thermal layer 600 in both mechanical and thermal contact with the chamber layer 200 and the chamber layer in mechanical contact with the aperture layer 540. In various embodiments, the apparatus may include one or more force members (not shown) that are configured to apply pressure to the receiving tray 520 in order to thermally couple the heat sources to the microfluidic cartridge 200 positioned in the receiving tray 520. The application of pressure may be important to ensure consistent thermal contact between the heater substrate and the reaction chambers, gates, and valves, etc., in the microfluidic cartridge 200. When the receiving tray 520 is in a closed position, thereby being positioned under the aperture plate 540 of the optical module 502, the force member, such as a motor assembly, below the receiving tray 520 may begin traveling upwards towards the optical module 502, thereby bringing the receiving tray 520 closer to the optical module 502. As the receiving tray 520 travels upwards towards the optical module 502, the cartridge 200 may begin to come in contact with a bottom surface of the aperture plate 540. The cartridge 200 may continue traveling upward until sufficient pressure is received on the cartridge 200. As discussed above, the aperture plate 540 may apply an equal pressure across all points of the top of the cartridge 200 and thus, presses the cartridge 200 against the heater substrate 600 with uniform pressure. As discussed, the aperture layer may be selected to possess properties which facilitate this operation. For example, the material selection of the aperture plate 540 may provide very little deflection of the cartridge 200, when pressed against it.

The application of uniform pressure of the cartridge 200 against the heater substrate 600 may allow for uniform heating for each of the components of the cartridge when desirable. Although uniform pressure and contact may be obtained between the heaters in the heater substrate 600 and the components (valves, gates, chambers, etc.) of the microfluidic networks in the cartridge 200, the heaters are not necessarily activated simultaneously, as discussed above. In certain embodiments, application of even pressure does not necessarily result in equal heating of different components of the cartridge 200. In some embodiments, both the activation of a specific heater in the heater substrate 600 along with the pressure applied by the aperture plate 540 to the cartridge 200 activate a particular component of cartridge 200.

FIGS. 9A-H are diagrams of the dimensions of one possible embodiment of the aperture plate. In this embodiment, a chemical conversion coat may be applied to adjust the reflective properties of the aperture layer. Some portions 9002 may be selected not to receive the chemical conversion coat. The coating may be applied to the surface of plate 540 or deposited throughout its material. In some embodiments, the material of the plate 540 may comprise steel. In other embodiments, the plate 540 may comprise aluminum. In yet other embodiments, the material of the plate 540 may comprise nickel. In some embodiments, the material of the plate can be a combination of two or more materials, including for example, aluminum, nickel, or steel.

In the embodiment shown in FIGS. 9A-H the dimensions of the plate have been selected to meet the constraints regarding chamber pressure and optical path to the detector pairs discussed above. The material thickness of the plate 540 starts out at 0.3125 inches and is machined down to the desired thickness. As indicated, much of the plate comprises a thickness of approximately 0.25 inches. However this thickness may vary, for example, the thickness over the aperture openings 557 may be 0.19 inches. As discussed above, the aperture opening thickness facilitates an unimpeded optical path between the photodetector and light source to the contents of the reaction chamber.

In general the dimensions of the aperture plate 540 are selected such that in combination with the properties of the materials constituting the aperture plate 540, the plate 540 provides sufficient pressure to the underlying chamber plate to facilitate proper heating and cooling as well as sufficient rigidity to prevent warping or deformation of the chamber plate. Such deformation may result in obstructions to the light source and photodetector optical path to the reaction chamber. Simultaneously, the dimensions of the plate should not impose an unfavorable distance from the reaction chamber of the chamber layer to the light-source and photodetector pair through the apertures 557. Neither should the aperture plate's dimensions 540 obstruct the optical path from the light-source and photodetector pair to the contents of the chamber reactor.

In some embodiments the normalizer plate 546 may be attached to the aperture plate by inserting screws at positions 9001 or other fixation means through an aperture. In other embodiments, these positions may facilitate broader calibration techniques via the apertures over the normalizer plates than with regard to the remaining apertures.

FIG. 10 illustrates various dimensions of the perspectives of the aperture plate of FIGS. 9A-H. As discussed above, in this embodiment, a chemical conversion coat may be first applied to prevent the base materials, e.g., aluminum, nickel or steel, from oxidation while also providing enhancing electrical grounding for proper electronics operation. Only surfaces which may be exposed to the optical operation are then selectively coated with black anodization.

Diagnostic Analysis Consistency

Certain of the present embodiments contemplate methods for ensuring consistent diagnostic analyses across trials within the same heater/detector and across different heater/detectors. Particularly, embodiments of a system and process for determining the duration and offsets for a plurality of PCR protocols so as to synchronize detection therebetween are disclosed. Additionally, methods for adjusting the reactor cooling time to ensure more consistent results are discussed.

Figure 11:
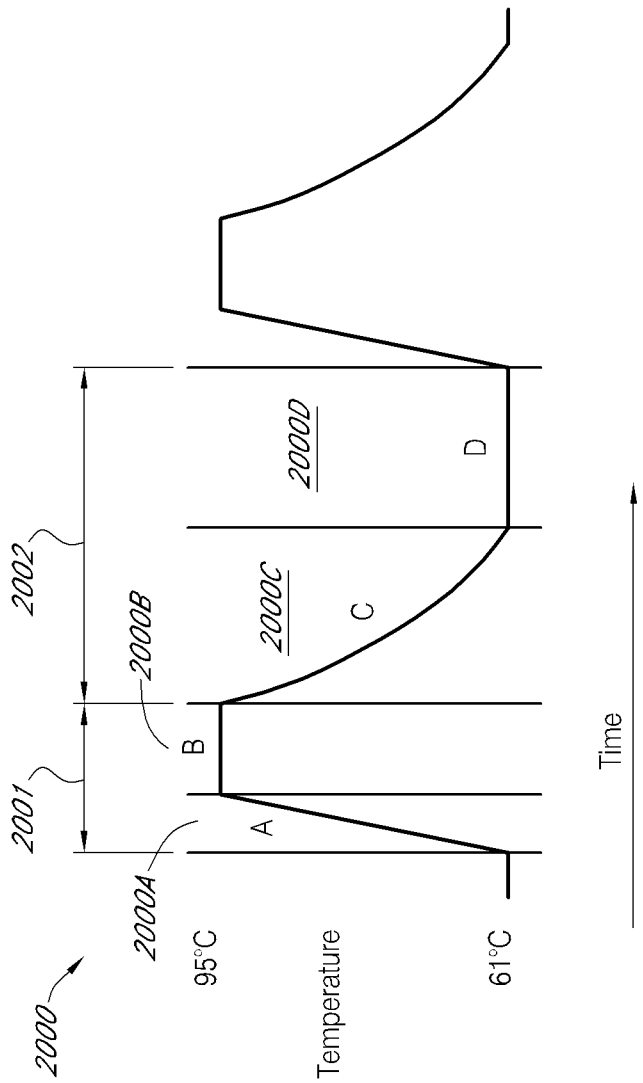
FIG. 11 is plot of a portion of a thermal profile for a possible protocol implemented in certain of the embodiments.

FIG. 11 is a temperature profile for a reaction chamber undergoing a particular protocol 2000. As illustrated above, the system in operation may comprise many different protocols of many different durations operating simultaneously in different reaction chambers. The protocol 2000 involves a plurality of identical heating/cooling cycles, where each cycle comprises denaturing plateaus 2000B and annealing plateaus 2000D where the temperature is maintained constant for a period of time. These cycles may be preceded by a non-periodic cycle of the protocol, such as an incubation period. In certain embodiments, the protocol may be specified as a collection of temperatures and periods of time. That is, the protocol may initially specify only that the chamber is to be held at 95° C. for the duration B and then held at 61° C. for the duration D. Certain embodiments contemplate grouping these segments into "steps" and "substeps" to facilitate user and automated control. For example, the heating and cooling cycle 2000B and D may be referred to as a "step" with the duration B at 95° C. and the duration D at 61° C. referred to as "substeps". In certain embodiments, a user may specify the durations of the substeps. In other embodiments, these durations may be retrieved from a database. Typically, these times are established either from a standard protocol or by user input, sometimes using an established "recipe" of temperatures and plateau times. In addition to these substeps, the protocol's temperature profile will also comprise transitions, such as transition 2000A from 61° C. to 95° C. and transition 2000C from 95° C. to 61° C. The duration of these transitions may be a consequence of the materials and environment about the reaction chamber and the nature of the heating elements employed.

In certain embodiments the thermal trajectory for both heating and cooling may be determined for the entirety of the reaction prior to the start of the run. In some systems, the contour of temperature versus time is monitored and adjusted throughout the reaction in order to minimize transition temperatures, and taking into account the variations in efficiencies of different heating elements. In other words, some systems utilize feedback control loops to drive to a target temperature, wherein the actual contour of the temperature time relationship can vary from cycle to cycle. Such adjustments can result in different overall reaction times, and, more importantly, different overall reaction efficiencies. Accordingly, in some embodiments, the systems and methods described herein advantageously provide systems wherein the contour of the temperature versus time relationship of the complete reaction for each independent reaction chamber (or group of chambers) is predetermined set prior to the start of the run. Not only does this advantageously allow for synchronization of the multiple detection steps across a plurality of different reactors, but it also enables for stricter control over parameters that minimize differences in reaction efficiencies that may arise as a result of different temperature/time contours. In some embodiments, the systems and methods provided herein provide for the report of errors at the end of a reaction if the measured temperature is different from the expected value when a run is completed.

At various points in the protocol temperature profile 2000, the user or recipe may specify that a detection occur. For example, for some protocols a detection may be requested at the end of segment 2000D. Were detections arbitrarily specified in each protocol, the detector head would need to travel between positions in an inefficient manner and may even find it impossible to perform detections at the requested times. That is, were each of a plurality of protocols to be initiated simultaneously and run in parallel simultaneously across each of the reaction chambers in the cartridge, it would be very inefficient for the detector to meet each protocol's detection requests. Particularly, once calibration was complete the detector would need to first travel to positions suitable to perform detections for each light source-detector pair in its array for the first profile. By the time the detector finished, however, each of the remaining protocols would be entering a period when detection is not to be performed. There will therefore be a "dead time" period when the detector cannot perform any detections and must instead simply sit idle waiting for the opportunity to perform the next detection. This "dead time" is inefficient and unnecessarily prolongs the diagnostic process. Furthermore, where successive detections are to be performed, the "dead time" may generate irregular and aperiodic detections of the same chamber, possibly introducing inconsistent readings.

Certain of the present embodiments contemplate automated adjustments to portions of the profile 2000 to facilitate efficient detection across multiple protocols. This may be accomplished by allowing the user to edit, or the system may edit automatically, the length of segment 2000B or 2000D.

It should be understood that so long as at least a minimum plateau time occurs, some minor extension of plateau times can be accommodated in most amplification protocols. This flexibility is utilized to all efficient accommodation of different assays being performed simultaneously, while performing real-time monitoring of amplification by reading the various assays using a scanning detector head.

If detection were to be performed during segment 2000B, for example, the system or the user may extend the duration of segment 2000B as necessary to accommodate detector head movement and to coordinate the reading of a plurality of assays being performed simultaneously. The duration of segments 2000A and 2000C may be calculated using a predetermined standard cooling rate from the preceding temperatures and incorporated into the analysis. Some embodiments do not allow the user to edit these segments and they are instead accounted for by the system internally.

In certain embodiments, the protocol adjustments determined by the system may comprise at least three separate forms. The first adjustment may comprise an "intra-cycle adjustment" wherein plateaus such as 2000B and 2000D of the protocol are extended such that the entire step cycle 2000A-D achieves a desired duration, in some instances an integer multiple of a detection cycle time. This adjustment is described with respect to FIG. 13. Once the intra-cycle adjustment is complete, the system may then perform an "inter-cycle adjustment". An inter-cycle adjustment may ensure that detection events within each cycle occur at integer multiples of a desired duration apart from one another (such as an integer multiple of the detection cycle time) between the cycles. These adjustments are discussed with regard to FIG. 14. The third adjustment may comprise a "starting offset adjustment" which may depend only on the lane used for protocol execution. These adjustments are discussed with respect to FIGS. 15A-C.

Protocol Adjustment Overview

Figure 12:
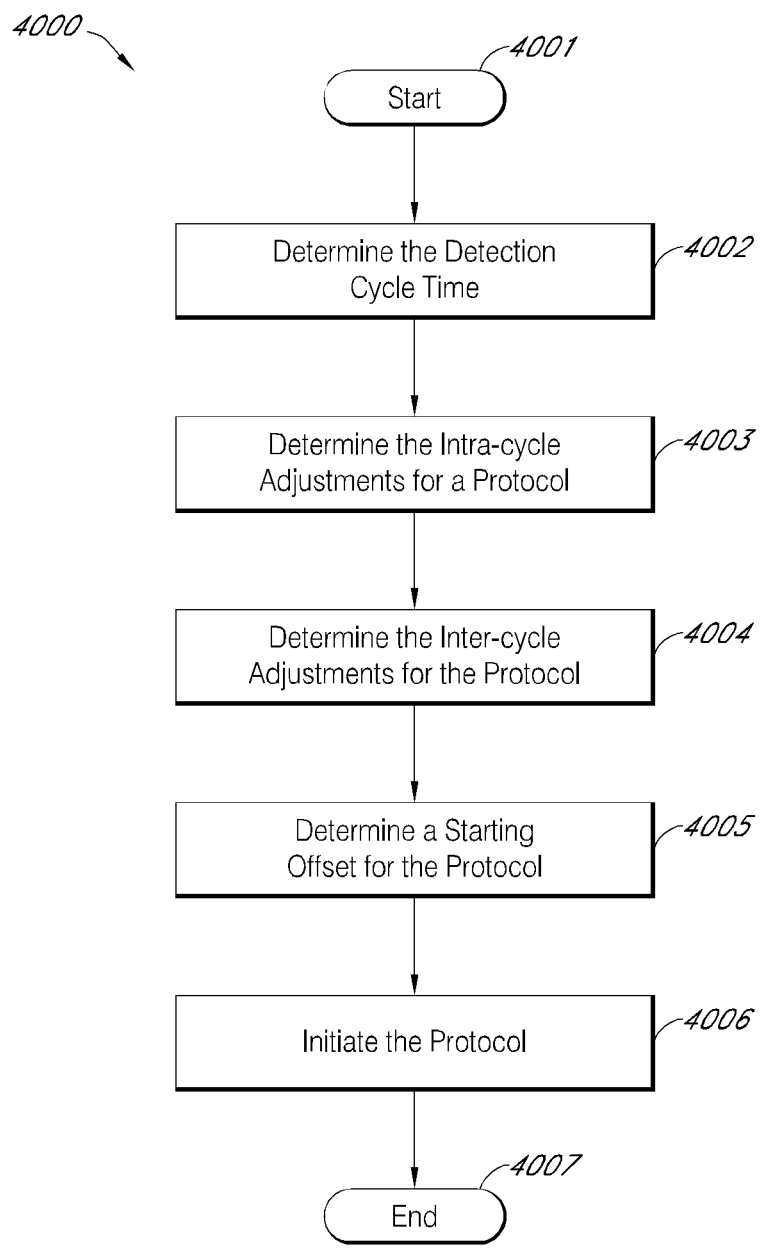
FIG. 12 is a flow diagram depicting a process for determining protocol durations, offsets, and detection times, so as to optimize and regiment detector efficiency.

FIG. 12 depicts a flow diagram of a process 4000 used in certain of the disclosed embodiments to determine an appropriate solution for the detector detection times and protocol profiles. Process 4000 may be implemented in software, hardware, or a firmware combination of the two. For example, the process may be implemented in any of an FPGA, a microcontroller, or software running on a computer processor. Portions of the process may be performed by a general purpose processor, such as a microcontroller, while other portions may be performed by dedicated hardware, software, or firmware systems. The process begins 4001 by determining a detection cycle time (or using a predetermined detection cycle time, e.g., already in memory) for the system 4002. The detection cycle time may comprise the time that is required for the detector to move to each of the detection positions (detection with each of the emitter/detector pairs in a detection head in each of the six columns of FIG. 6), perform all necessary detections, and return to an initial position. Optionally, the user or system may be allowed to make adjustments to the detection procedure so as to modify the detection cycle time. For example, the user may wish to only perform detection using a subset of the detectors. In some embodiments the detection cycle time is approximately 10 seconds, when the embodiment comprises six columns of detector pairs and all six columns are used.

In some embodiments, the process may first determine a plurality of "intra-cycle adjustments" for one or more of the protocols 4003. As discussed below with respect to FIG. 13, the durations for a step or substep may comprise the time to perform a particular step or substep within the protocol. The cycle times may be determined by a combination of user specifications and system identified constraints. In certain embodiments, the system will require the plurality of cycle times to be integer multiples of the detection cycle time. "Intra-cycle adjustments" may be introduced to satisfy this constraint. For example, if the detection cycle time were 12.2 seconds, the cycle times for a protocol step may be 22.4, 33.6, 44.8, or any other N*12.2 duration, where N is an integer greater than 0. In some embodiments, it is only necessary to impose this constraint when a detection is to be performed within the cycle.

Thus, intra-cycle adjustments ensure that the cycle of the protocol is an integer multiple of the detection cycle time. However, a detection may be requested at any point within a cycle. If the detection cycle time is 10 seconds, then the very earliest that a detection may be performed is at 10 seconds after the protocol initiates. Detections may then be performed at integer multiples after that time (20, 30, 40 seconds, etc.).

Thus, a further adjustment, an "inter-cycle" adjustment 4004, may then be determined to ensure that the requested detection occurs at the appropriate time. These "inter-cycle adjustments" may be incorporated into the protocol as additional delays between protocol steps or substeps. Phrased differently, a PCR protocol once subjected to "intra-cycle" adjustments may comprise "valid" cycle steps. The PCR protocol may then be generated by chaining together each of the steps and adding transitions from step to step. The "inter-cycle adjustments" 4004 ensure that the detection times occur at the desired integer multiples of the detection cycle time after the cycles have been chained together.

For example, for a system having a detection cycle time of 10 seconds a protocol may comprise a step having its first detection at 18 seconds into a cycle. The cycle duration (the duration of the entire step) may last for 30 seconds (perhaps after an "intra-cycle" adjustment). Thus, while the cycle time as a whole is properly aligned with the 10 second detection cycle time (3×10=30 seconds) the first detection is itself not properly aligned with the detection (18 second is not a multiple of 10 seconds). The system will add 2 seconds of "inter-cycle" adjustment to the very first detection run so that the first detection occurs 20 seconds after the start of the protocol. This may be done by extending the previous step's final hold temperature for an additional 2 seconds via a "padding adjustment". If there is no previous step, the system would insert a 2 second hold at ambient temperature to the beginning of the first run of the cycle. Thus, if the system begins operation at T0, the first detection will occur at T0+20 seconds, the second detection at T0+50 seconds, and so forth.

Because of the inter and intra-cycle adjustments, the protocol is now in a form such that detections will only be requested at times convenient for the detector head to move to the reaction chamber performing the protocol. Were all protocols performed in reaction chambers located in the first column of the cartridge (and sufficient number of detectors present in the detector head) intra and inter-cycle adjustments alone would suffice to properly modify the protocol for efficient detection (a first column here referring to a column of lanes such as lanes 1706a and 1706b with associated chambers 1703a and 1703b in FIG. 3A). However, because the protocols operate in different columns of the cartridge it is further necessary to offset the protocol's initiation to compensate for the detector head's delay in reaching the chamber location.

Thus "starting adjustment offsets" are added to the protocol based on the location of the chamber in which the protocol is performed. These "starting adjustment offsets" 4005 are described in greater detail with respect to FIGS. 15A-C. In some embodiments, these adjustments are made at run time and rely solely on the location of the lane of execution. For example, no adjustment may be necessary for a protocol running in lanes located in a first column of the chamber, so a protocol run in these lanes' chambers will have a delayed start time of +0 seconds. Each subsequent column of lanes gains a delay of 400 milliseconds for its distance from the first column, due to the time required for the detections (two detections at 100 milliseconds each, performed asynchronously in this embodiment) and the detector motor movement (200 milliseconds). In this example, with a detection cycle time of 10 seconds, the first possible detection for each column of lanes is as follows: column 1 has its first detection at 10 seconds, column 2 has its first detection at 10.4 seconds, column 3 has its first detection at 10.8 seconds, etc. By delaying the start of a properly aligned protocol by the necessary time for a particular lane, the expected alignment can be maintained. While this particular example assumes that the protocol is already aligned (from adjustments 4003 and 4004), the skilled artisan will readily appreciate that other embodiments may determine the offsets anticipating future adjustments.

Although described in the order of steps 4003, 4005, and 4004, one will readily recognize that these steps may be arranged into any other suitable order, and neither need the system perform each step successively. In some embodiments, however, such as that described above, it may be necessary to perform inter-cycle adjustments after performing intra-cycle adjustments, as the inter-cycle adjustment depends on the intra-cycle modification. In contrast, the starting-offset adjustment 4005 may not depend on any previous determination. That is, in some embodiments the starting offset 4005 need be determined only once at run time, whereas the intra-cycle adjustments 4003 and inter-cycle adjustments 4004 may be performed for each cycle step in the protocols.

In some embodiments, once the protocol times have been properly adjusted, the process may then initiate the protocols 4006. In some embodiments a processor may simply place the offsets in a memory location for retrieval by a separate dedicated component of the system which itself initiates each protocol.

Intra-Cycle Adjustment

Figure 13:
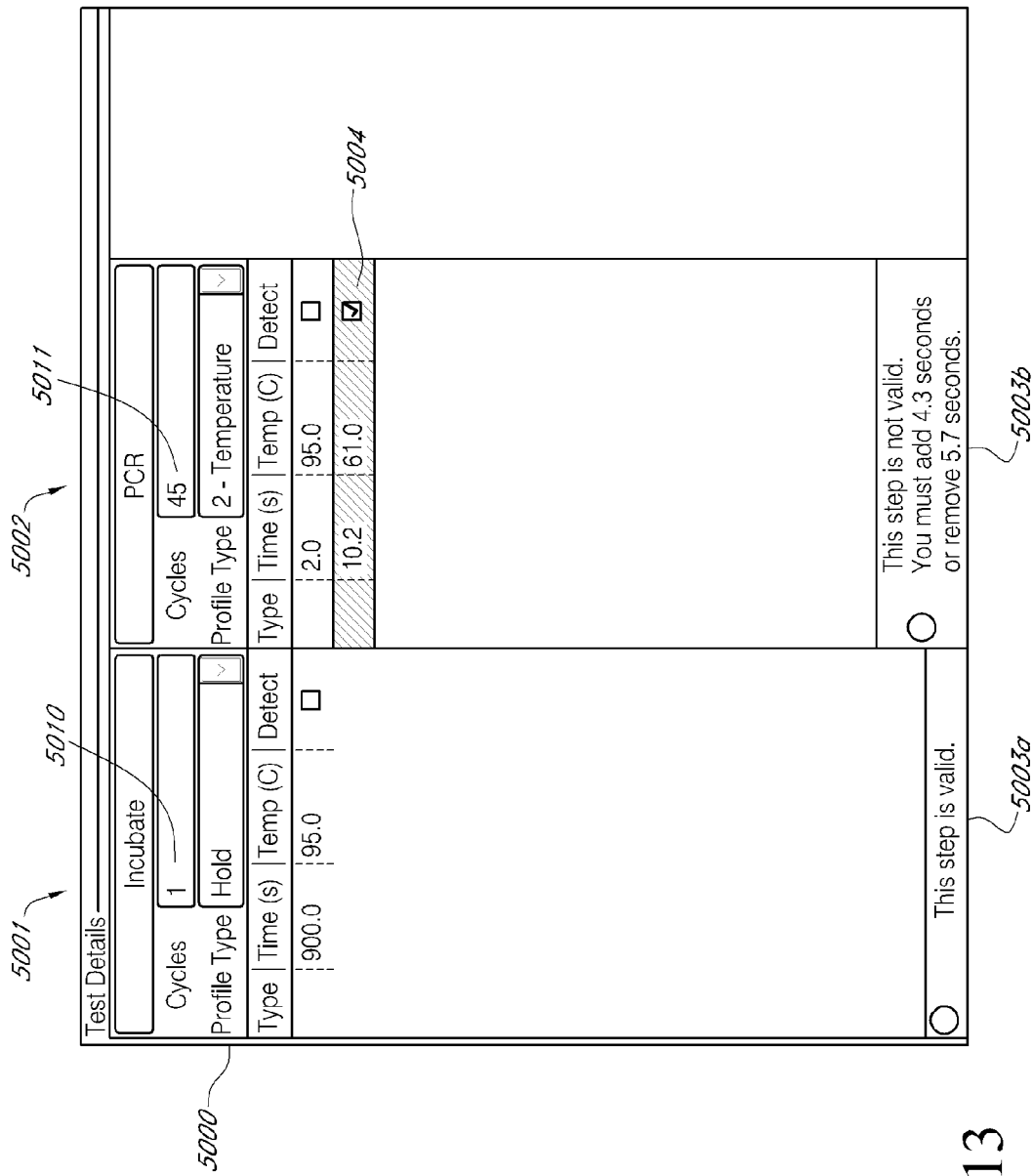
FIG. 13 illustrates a portion of a user interface for selecting durations of certain protocol steps and substeps and determination of the accompanying intra-cycle adjustment.

"Intra-cycle adjustments" comprise adjustments to step or substep intervals, as may have been specified by a user or received from a database, so that the step as a whole is an integer multiple of a predetermined duration. With reference to FIG. 13 in certain embodiments the user may specify certain features of the protocol profile, such as the desired times for a protocol substep, using a user interface, or graphical user interface (GUI). In some embodiments, the system may then validate the user's selection. After calculating segment lengths for each of the substeps, the system software will validate the step cycle time and indicate if any adjustments are necessary. In some embodiments a "valid" step cycle time is a step cycle time that is an integer multiple of the detection cycle time. If a step cycle time is not valid, the user may be prompted to make adjustments for that step 5003b. If no adjustment is necessary, the user may be notified that the step is aligned properly 5003a.

In the example of FIG. 13, the user has required an incubation step 5001 comprising a single substep of 900 seconds. The user has requested that the step 5001 occur only once 5010 and therefore comprises a single step cycle. In this example, the detection cycle comprises 10 seconds.

The user has not specified that any detection is to be performed and accordingly the step is valid, since the step will not require that the detector head's position be adjusted. When no detection is requested the system records the requested time intervals, for future offset considerations, but may not impose any constraint that the time interval be a multiple of the detection time (though the duration may be considered in determining a subsequent inter-cycle adjustment). If, however, in this example the user had requested detection during this step, the step would still be valid if no other delays are incurred, as 900 seconds is a multiple of the 10 seconds detection cycle. In either event, in the illustrated embodiment, the system has determined that this step entry is valid.

In the example illustrated in FIG. 13, the step PCR 5002 comprises two substeps, a first substep where the chamber is to be held at 95° C. and another substep where the chamber is to be held at 61° C. The user has requested that 45 cycles of this step be performed 5011. The user has requested that the first substep last 2 seconds and that the second substep last 10.2 seconds for a total of 12.2 seconds. As discussed above with respect to FIG. 7, the system may have also calculated the transition time from 95° C. to 61° C. and added this duration to the user requests. In this example, heating from 61° C. to 95° C. requires 4.25 seconds and cooling from 95° C. to 61° C. in 7.05 seconds. These values may be stored internally in the system's memory or determined dynamically based on the user inputs. Finally, in some embodiments, when a detection is requested for a substep 5004, as the user has requested here, the system adds an additional delay to the hold time for that substep. In this example, that delay is 2.2 seconds, which accounts for the minimal time required to allow the detector to move and detect with each of six columns of light emitter-photodetector pairs in the detector head. That is, in this example, each color detection requires 200 milliseconds of exposure time and 200 milliseconds to move the motor between columns (5 transitions*200 ms+6 detections*200 ms=2.2 seconds).

Thus, the total duration for the step as a whole is:

4.25(heat)+2.0(denature)+7.05(cool)+10.2(anneal)+ 2.2(detection)=25.7 seconds.

As 25.7 seconds is not a multiple of the 10 second detection time, adjustment will be necessary. As indicated 5003b, the system informs the user that they may either remove 5.7 seconds from the step duration or add an additional 4.3 seconds to achieve a multiple of the detection cycle time (i.e., a multiple of 10 seconds). These "intra-cycle step adjustments" will be incorporated into the protocol after the user's selection.

One will recognize that the system may consider a plurality of other factors not indicated in this example when providing the user with an adjustment range. For example, additional delays to motor movement or incubation preparation may be factored in to the system's analysis.

Inter-Cycle Adjustments

Figure 14:
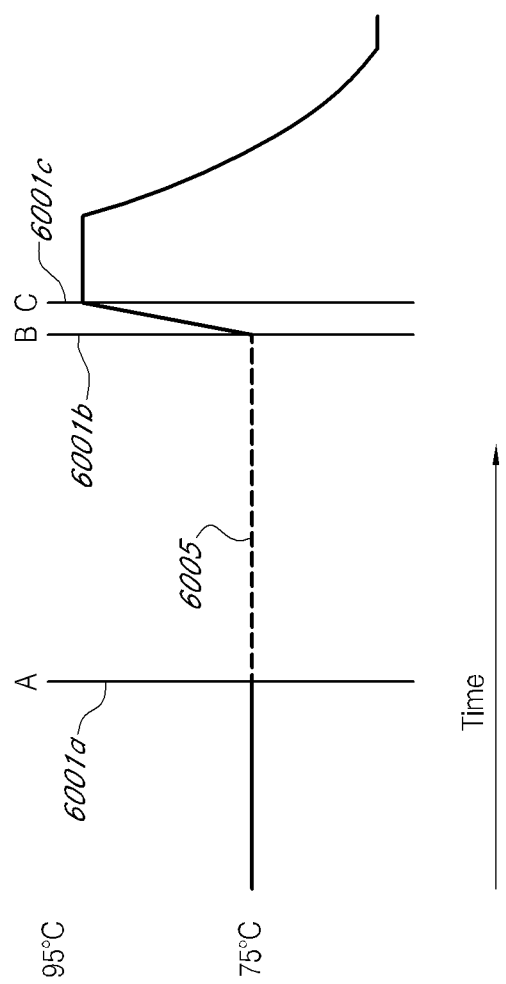
FIG. 14 is a plot of a thermal profile comprising an inter-cycle adjustment.

As mentioned above, "inter-cycle adjustments" comprise adjustments to the first cycle of a substep so as to create a delay between cycle steps. "Inter-cycle adjustments" may depend on the timing of the preceding steps and the end temperature of the immediately preceding step (if one exists). With reference to FIG. 14 the "inter-cycle adjustment" 6005 determined to achieve a proper detection time occurrence, will be described.

In some embodiments the adjustment 6005 is determined by first determining the time required to heat or cool the temperature from the end of the previous step to the first substep temperature of the next step. If any additional time is necessary for alignment, the temperature from the end of the previous step may be maintained for this time. An example of alignment between the end temperature of a hold step at 75° C. to the first substep temperature of 95° C. is shown in FIG. 14. The temperature is ramped at 8° C./s from 75° C. to 95° C. from points 6001b to 6001c, with the remaining time required for alignment spent holding at 75° C. after the end of the previous step, from points 6001a to 6001b. This period may be referred to as an "inter-cycle adjustment". To achieve continuance of detection alignment between steps, it may be necessary to shift (or delay) the start of a step cycle after the end of the previous step by this "inter-cycle adjustment". The time required to heat or cool the temperature from the end of the previous step to the first substep temperature of the next step may then be calculated. If any additional time is necessary for alignment, the temperature from the end of the previous step is maintained for the time of the "inter-cycle adjustment". In some embodiments, the system may factor in these considerations when receiving user input via GUI 5000 and incorporate them into the proposed variance 5003b.

Starting Offset Adjustments

Figure 15A:
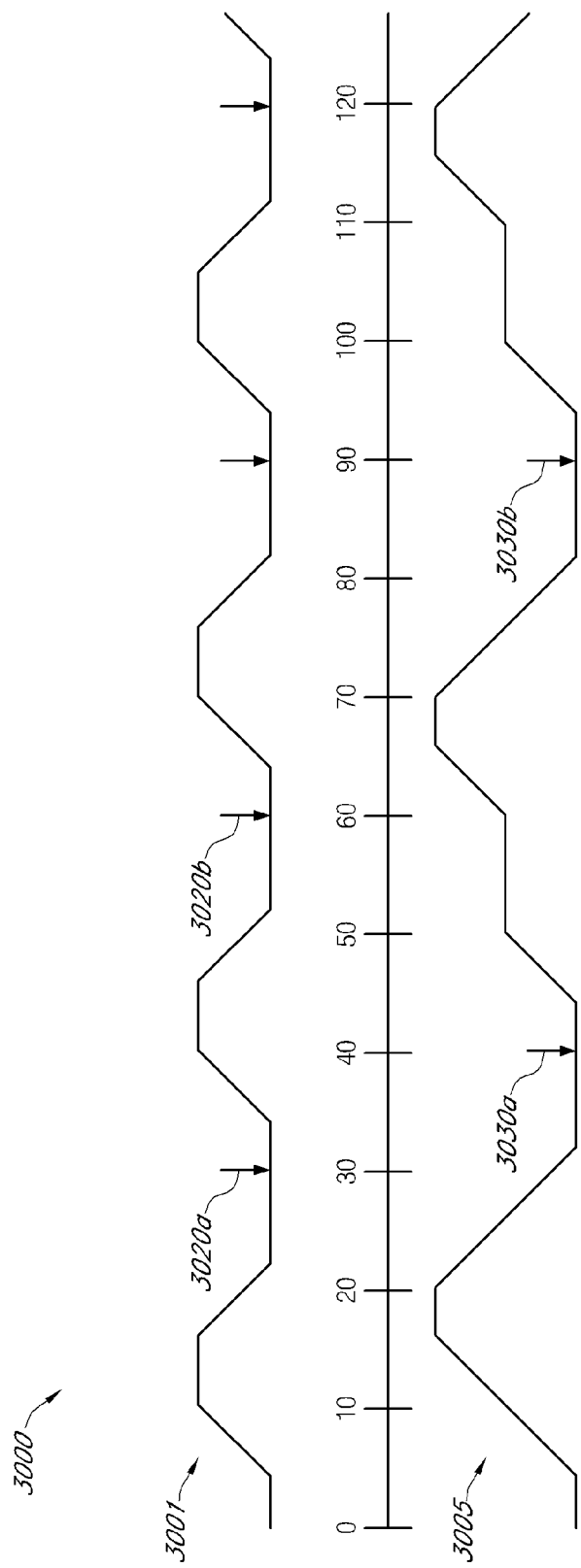
FIGS. 15A-C plot a plurality of thermal profiles for a plurality of protocols implemented in certain of the embodiments.

FIG. 15A illustrates the beginning cycles of two separate protocol profiles 3001 and 3005. In each of these protocols the inter and intra-cycle adjustments may have been performed, but the starting offset has yet to be applied. In this example, profile 3001 includes a step with a cycle time of 30 seconds (the interval from time 0 to time 30). A time for detection 3020a, or a detection request occurs 30 seconds. Note that pursuant to the inter-cycle adjustments discussed above, a small delay may have been included in the protocol 3001 just prior to the first heat ramp for alignment of the first detection 3020a. As discussed above, the inter-cycle and intra-cycle adjustments facilitate detection requests being made at integer multiples of the detection cycle time. Here, for a detection cycle time of 10 seconds, the requests 3020a and 3020b occur at the integer multiples 30 and 60 seconds.

The second protocol 3005 includes a different profile from 3001. The profile 3005 comprises an initialization step lasting from 0 to 30 seconds. The profile 3005 is then followed by a plurality of 50 second cycles, with the first detection at 40 seconds. These cycles represent a 3-Temperature PCR, which includes a denature at a high temperature, the anneal and detection at the low temperature, and then an extension at a middle temperature. As before, the first initialization cycle may include a small inter-cycle delay at the beginning for alignment. One will recognize that his inter-cycle delay may be inserted at a variety of positions about the initialization step to ensure detection alignment.

Figure 15B:
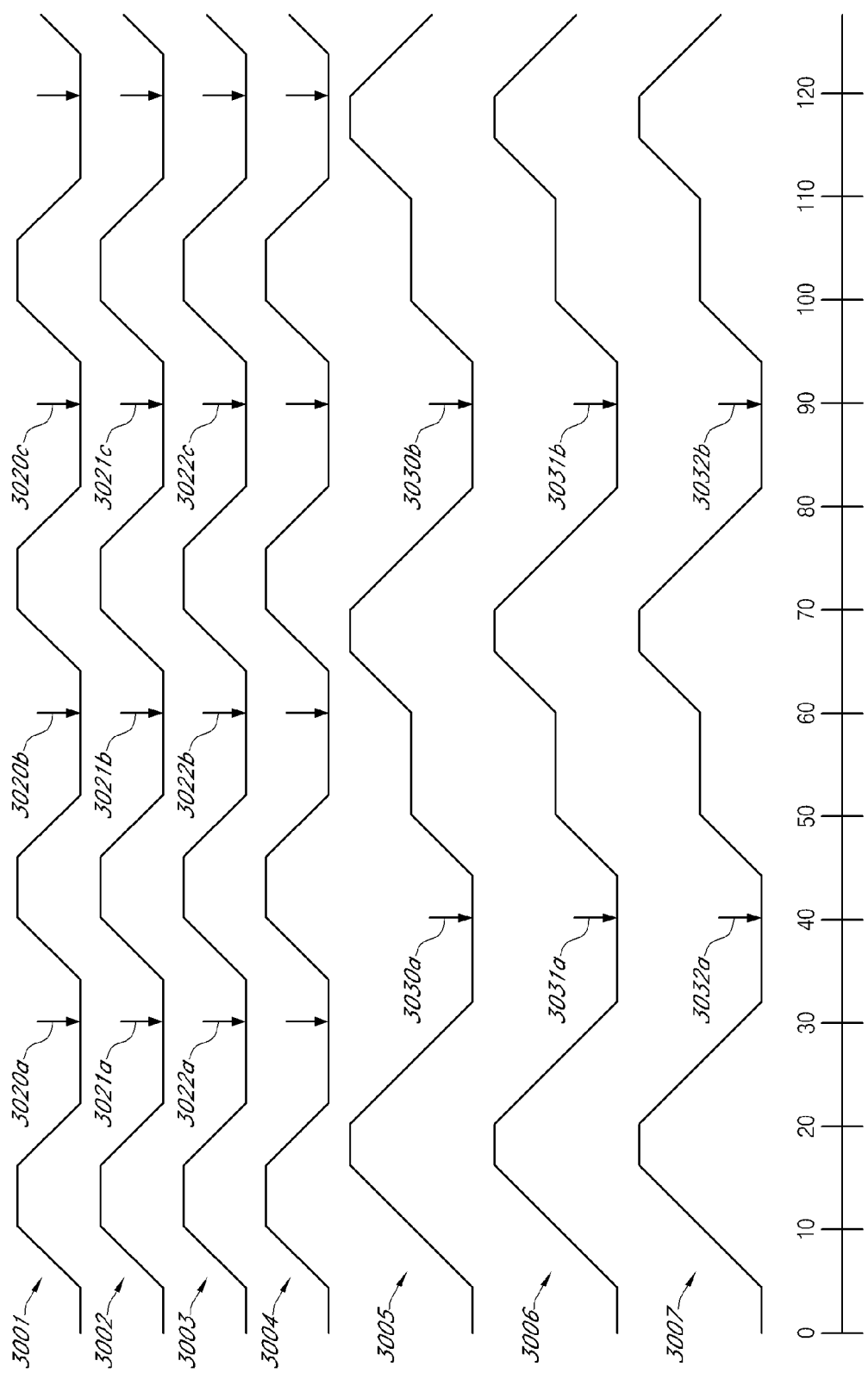

FIG. 15B illustrates multiple instances of the two protocols from FIG. 15A. Were it possible to perform detections across all lanes in all chamber columns simultaneously, the profiles illustrated in FIG. 15B would be suitable. However, due to time delay required for the detector head to scan across a chamber column with each of its columns of detector pairs, it is necessary to offset each of the protocols 3001-3007 based on the location of the chamber in which they are executed. For simplicity, each of the protocols 3001-3007 is presumed to be run in a neighboring column. If protocol 3001 is run in the first chamber column, then protocol 3002 is run in the second, 3003 in the third, 3004 in the fourth, etc.

Figure 15C:
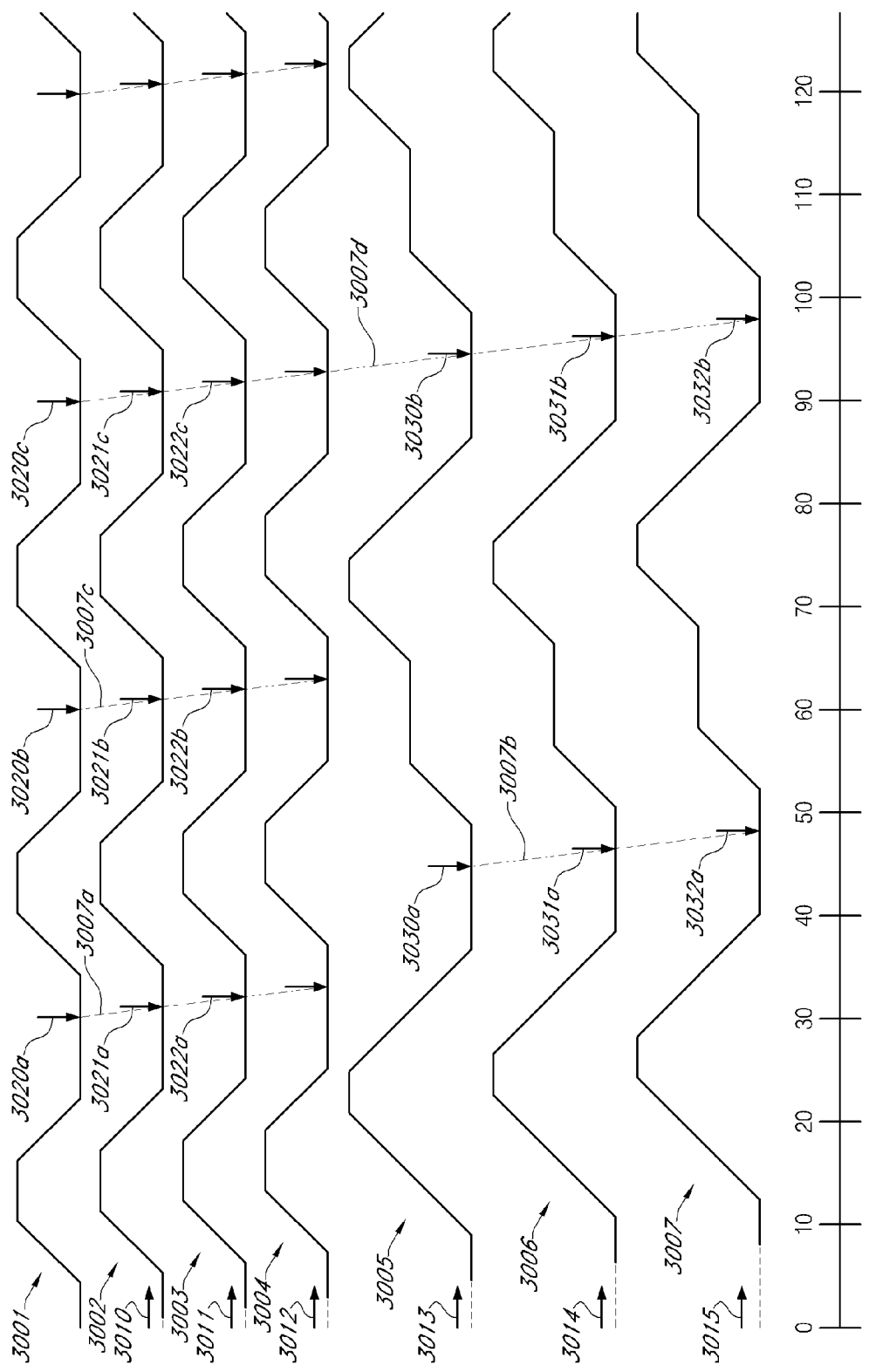

FIG. 15C illustrates the execution of the protocols 3001-3007 with the "starting offset adjustments" 3010-3015 introduced to ensure detection alignment. The starting offsets demonstrate the movement of the detector across the lanes of the cartridge and the synchronization of that movement with the detections required by each of the executing protocols. Thus, protocol 3001 will request detection, using the first detector head column at request 3020*a*. When the detector head moves to align the second detector head column with the chamber of protocol 3001, the first detector head column will be arranged over the chamber of 3002 which, advantageously, is now also requesting a detection 3021*a*. Subsequently, the process continues with the first column of the detector head now reading protocol 3003 at request 3022*a*, the second column reading 3002, and the third reading 3001. One will recognize that the skew illustrated in FIG. 15C is not to scale (in some embodiments the skew may be on the order of ~400 milliseconds), and has been illustrated as shown for only for purposes of explanation.

Thus, with properly selected "starting adjustments" the system can ensure consistent detection times across each of the reactors. As illustrated in FIG. 15C, orderly and efficient detections are made along lines 3007*a-d* when the determined solution is implemented by the detector system. Thus, detection for a particular reactor will occur at the same time from cycle to cycle. The details for one embodiment for determining these solutions will be described in greater detail with regard to FIG. 16.

Active Cooling

Figure 16:
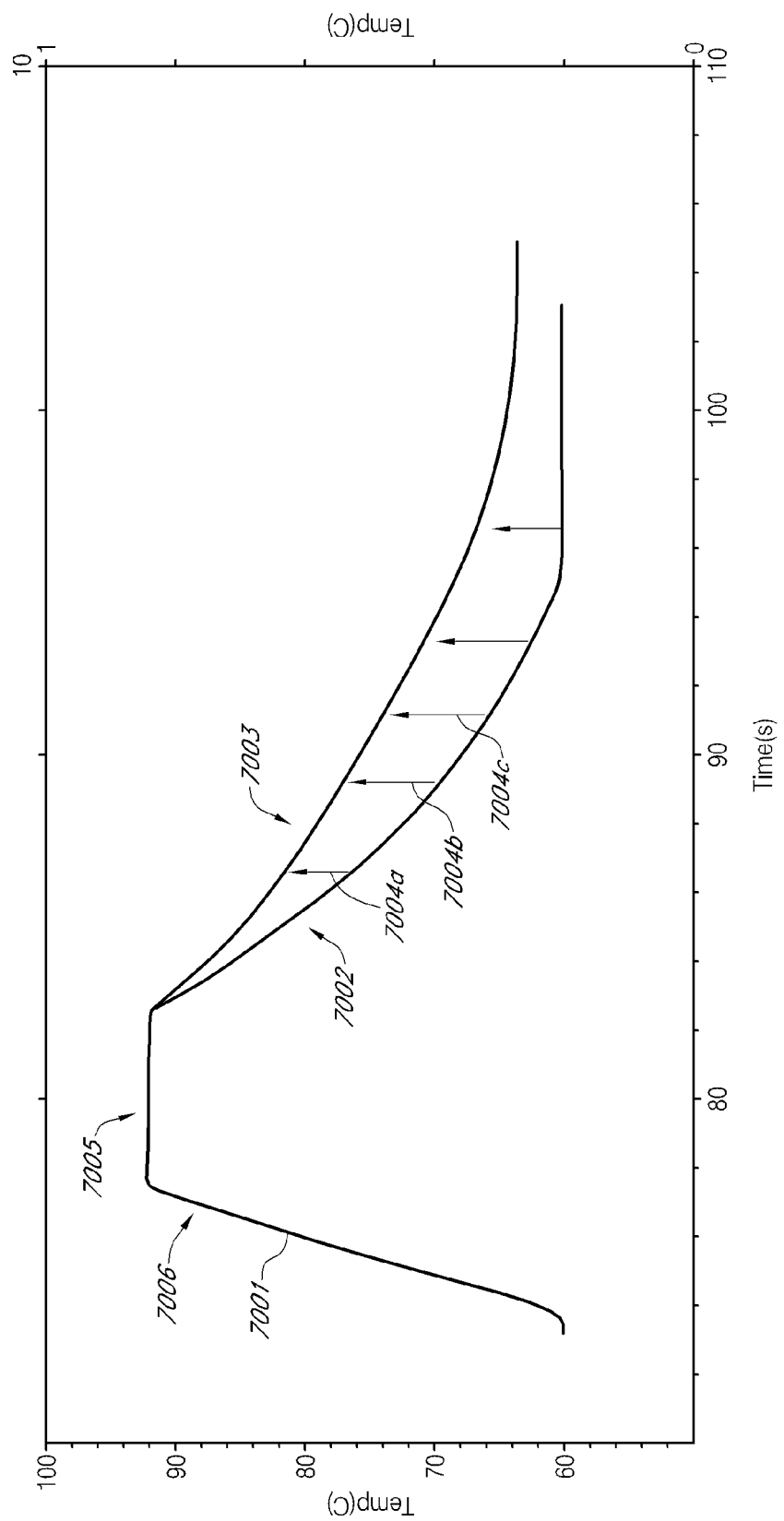
FIG. 16 is plot of a thermal profile under active cooling as implemented in certain of the embodiments.

In certain of the embodiments while heating of the reactor chamber is active, that is, heaters are actively applied to the chamber, cooling of the reactor chamber may passive, where convection alone is used to cool the reactor contents. In order to further provide for consistent diagnostic performance, certain of the embodiments contemplate active participation in the reactor's cooling process to ensure consistent behavior. FIG. 16 illustrates a thermal profile 7001 comprising a cooling component. The profile 7001 comprises a rise time 7006, a plateau 7005, and a cooling period 7002/7003.

The ambient temperature in the location where the heating/detection unit is located may not be the same. That is, a system operating in southern Arizona may not be subjected to the same ambient temperatures as a system operating in northern Alaska. Thus, in the hottest ambient temperature in which the system is expected to be operated, the profile 7001 may have a cooling curve 7003. In a cooler environment, the cooling profile 7002 may instead result. To compensate for the difference, certain embodiments contemplate monitoring the reactor cooling profile via the temperature sensors, possibly those discussed with regard to FIG. 3*b*. When deviations from the maximum profile 7003 are detected, sufficient heating may be applied so that the profile 7002 instead follows the profile 7003. In some embodiments heat may be applied periodically at times 7004*a-c*, whereas the heat may be applied continuously in other embodiments. In this manner, consistent profiles may be achieved regardless of the thermocycler's geographic location or operating ambient temperature.

Certain of these embodiments apply Newton's law of cooling to determine when to apply the heaters:

$$T(t)=T_a+(T(0)-T_a)e^{-rt}$$

Where: T(t) is the temperature at time t, T(0) is the initial temperature, Ta is the ambient temperature parameter, r is the decay constant parameter, and t is time. In some embodiments 50.2 degrees Celsius and 0.098 may be used as the ambient temperature parameter and decay constant parameter, respectively. In this embodiment, the ambient temperature parameter is selected to be higher than any expected ambient operating temperature, thus allowing full control over the cooling cycle by applying at least some small amount of heat during each cooling cycle, regardless of ambient temperature, in order to match the actual cooling to the cooling curve of the maximal profile 7003 in each instance.

As used herein, an "input" can be, for example, data received from a keyboard, rollerball, mouse, voice recognition system or other device capable of transmitting information from a user to a computer. The input device can also be a touch screen associated with the display, in which case the user responds to prompts on the display by touching the screen. The user may enter textual information through the input device such as the keyboard or the touch-screen.

The invention is operational with numerous other general purpose or special purpose computing system environments or configurations. Examples of well-known computing systems, environments, and/or configurations that may be suitable for use with the invention include, but are not limited to, microcontrollers, personal computers, server computers, hand-held or laptop devices, multiprocessor systems, microprocessor-based systems, programmable consumer electronics, network PCs, minicomputers, mainframe computers, distributed computing environments that include any of the above systems or devices.

As used herein, "instructions" refer to computer-implemented steps for processing information in the system. Instructions can be implemented in software, firmware or hardware and include any type of programmed step undertaken by components of the system.

A "microprocessor" or "processor" may be any conventional general purpose single- or multi-core microprocessor such as a Pentium® processor, Intel® Core™, a 8051 processor, a MIPS® processor, or an ALPHA® processor. In addition, the microprocessor may be any conventional special purpose microprocessor such as a digital signal processor or a graphics processor. A "processor" may also refer to, but is not limited to, microcontrollers, field programmable gate arrays (FPGAs), application-specific integrated circuits (ASICs), complex programmable logic devices (CPLDs), programmable logic arrays (PLAs), microprocessors, or other similar processing devices.

The system is comprised of various modules as discussed in detail below. As can be appreciated by one of ordinary skill in the art, each of the modules comprises various sub-routines, procedures, definitional statements and macros. Each of the modules are typically separately compiled and linked into a single executable program. Therefore, the following description of each of the modules is used for convenience to describe the functionality of the preferred system. Thus, the processes that are undergone by each of the modules may be arbitrarily redistributed to one of the other modules, combined together in a single module, or made available in, for example, a shareable dynamic link library.

Certain embodiments of the system may be used in connection with various operating systems such as SNOW LEOPARD®, iOS®, LINUX, UNIX or MICROSOFT WINDOWS®, or any other suitable operating system.

Certain embodiments of the system may be written in any conventional programming language such as assembly, C, C++, BASIC, Pascal, or Java, and run under a conventional operating system, or the like, or any other suitable programming language.

In addition, the modules or instructions may be stored onto one or more programmable storage devices, such as FLASH drives, CD-ROMs, hard disks, and DVDs. One embodiment includes a programmable storage device having instructions stored thereon.

While the above processes and methods are described above as including certain steps and are described in a particular order, it should be recognized that these processes and methods may include additional steps or may omit some of the steps described. Further, each of the steps of the processes does not necessarily need to be performed in the order it is described.

While the above description has shown, described, and pointed out novel features of the invention as applied to various embodiments, it will be understood that various omissions, substitutions, and changes in the form and details of the system or process illustrated may be made by those skilled in the art without departing from the spirit of the invention. As will be recognized, the present invention may be embodied within a form that does not provide all of the features and benefits set forth herein, as some features may be used or practiced separately from others.

The steps of a method or algorithm described in connection with the embodiments disclosed herein may be embodied directly in hardware, in a software module executed by a processor, or in a combination of the two. A software module may reside in RAM memory, flash memory, ROM memory, EPROM memory, EEPROM memory, registers, hard disk, a removable disk, a CD-ROM, or any other form of storage medium known in the art. An exemplary storage medium may be coupled to the processor such the processor can read information from, and write information to, the storage medium. In the alternative, the storage medium may be integral to the processor. The processor and the storage medium may reside in an ASIC. The ASIC may reside in a user terminal. In the alternative, the processor and the storage medium may reside as discrete components in a user terminal.

What is claimed is:

1. A system comprising:
   a plurality of reaction chambers and a plurality of heating elements in thermal communication with the plurality of reaction chambers, each reaction chamber configured for independently performing polynucleotide amplification according to a plurality of amplification protocols;
   a detector head comprising a plurality of photodetector and light source pairs, the detector head being movable such that the detector head can perform a detection with each of the plurality of photodetector and light source pairs at each of the plurality of reaction chambers; and
   a processor configured to:
   (a) determine a detection cycle time, the detection cycle time comprising the amount of time required to perform a detection with the detector head on each of the plurality of reaction chambers with each of the plurality of photodetector and light source pairs;
   (b) configure the detector head and at least one of the plurality of heating elements based on an amplification protocol of the plurality of amplification protocols, the amplification protocol comprising one or more step cycles, each step cycle having a step cycle time, wherein each step cycle includes:
   (i) activating the at least one of the plurality of heating elements to reach a temperature plateau,
   (ii) maintaining the temperature plateau via the at least one of the plurality of heating elements for a first portion of the step cycle time,
   (iii) deactivating the at least one of the plurality of heating elements for a second portion of the step cycle time, and
   (iv) activating the detector head at a detection cycle time during the step cycle time;
   (c) determine the first portion of the step cycle time is not an integer multiple of the detection cycle time;
   (d) modify the amplification protocol to extend a duration of the first portion of the step cycle time during which the at least one of the plurality of heating elements maintains the temperature plateau such that the step cycle time becomes an integer multiple of the detection cycle time; and
   (e) control the detector head and at least one of the plurality of heating elements based at least in part on the modified amplification protocol.

2. The system of claim 1, wherein the processor is configured to extend the duration of the first portion of the step cycle based at least in part on a timing of the request for detection within the step cycle of at least two or more of the plurality of amplification protocols when the two or more of the plurality of amplification protocols are simultaneously run.

3. The system of claim 1, wherein the processor is further configured to extend the duration of the first portion of the step cycle time such that a time for detection within the step cycle occurs at a multiple of the detection cycle time.

4. The system of claim 1, wherein the processor is further configured to determine a starting offset adjustment for activating the at least one of the plurality of heating elements during the step cycle time based on a position of the reaction chamber associated with the amplification protocol.

5. The system of claim 1, wherein the detection cycle time comprises the amount of time required for a detector head to perform a predetermined plurality of detections for a reaction chamber.

6. The system of claim 5, wherein the detection cycle time further comprises a time required for movement of the detector head to each of a plurality of reaction chamber detection positions and movement of the detector head to the start position.

7. The system of claim 1, wherein the amplification protocol comprises a polymerase chain reaction (PCR) protocol.

8. The system of claim 1, wherein the processor is further configured to initiate the modified amplification protocol.

9. The system of claim 1, wherein the processor is further configured to identify an intra-cycle adjustment to lengthen or shorten at least one of the first portion of the step cycle time or the second portion of the step cycle time.

10. The system of claim 1, further comprising determining an inter-cycle adjustment to lengthen or shorten the time between steps of the protocol.

* * * * *